(12) United States Patent
Hwang et al.

(10) Patent No.: US 7,427,677 B2
(45) Date of Patent: Sep. 23, 2008

(54) EXPRESSION OF ZEBRAFISH BONE MORPHOGENETIC PROTEIN 4

(75) Inventors: Sheng-Ping L. Hwang, Taipei (TW); Hsuan Shentu, Fongyuan (TW); Hui-Ju Wen, Shangong Township, Taichung County (TW)

(73) Assignee: Academia Sinica, Taipei (CN)

( * ) Notice: Subject to any disclaimer, the term of this patent is extended or adjusted under 35 U.S.C. 154(b) by 502 days.

(21) Appl. No.: 10/612,594

(22) Filed: Jul. 1, 2003

(65) Prior Publication Data

US 2005/0005317 A1   Jan. 6, 2005

(51) Int. Cl.
  *C07H 21/04* (2006.01)
  *C12N 15/11* (2006.01)
  *A01K 67/027* (2006.01)

(52) U.S. Cl. .................. 536/24.1; 536/23.1; 800/20

(58) Field of Classification Search ................ None
  See application file for complete search history.

(56) References Cited

U.S. PATENT DOCUMENTS

| | | | | |
|---|---|---|---|---|
| 6,071,518 | A * | 6/2000 | Petersen | 424/139.1 |
| 6,083,690 | A | 7/2000 | Harris et al. | 435/6 |
| 6,159,696 | A | 12/2000 | Dijkema et al. | 435/6 |
| 6,379,961 | B1 | 4/2002 | Jessell et al. | 435/377 |
| 6,458,944 | B1 | 10/2002 | Kawai et al. | 536/23.5 |
| 6,475,735 | B1 | 11/2002 | Sugiura | 435/6 |

OTHER PUBLICATIONS

GenBank accession No. AY156927. Direct submission on Sep. 30, 2002 by Shentu, H. and Hwang, S.-P.L.*
Bayer et al. A transgene containing IacZ is expressed in primary sensory neurons in zebrafish. Development 115: 421-426. 1992.*
Alexander, et al., "Screening Mosaic F1 Females for Mutations Affecting Zebrafish Heart Induction and Patterning", *Dev. Genet.*, 22:288-299 (1998).
Amsterdam et al., "The Aequorea Victoria green fluorescent protein can be used as a reporter in live zebrafish embryos", *Dev. Biol.*, 171:123-129 (1995).
Blader et al., "Cleavage of the BMP-4 Antagonist Chordin by Zebrafish Tolloid", *Science*, 278:1937-1940 (1997).
Carvajal et al., "A BAC transgenic analysis of the Mrf4/Myf5 locus reveals interdigitated elements that control activation and maintenance of gene expression during muscle development", *Development*, 128:1857-1868 (2001).
Chen et al., "Left-right pattern of cardiac BMP4 may drive asymmetry of the heart in zebrafish", *Development*, 124:4373-4382 (1997).
Chin et al., "Bone morphogenetic protein-4 expression characterizes inductive boundaries in organs of developing zebrafish", *Dev. Genes. Evol.*, 202:107-114 (1997).
Culp et al., "High-frequency germ-line transmission of plasmid DNA sequences injected into fertilized zebrafish eggs", *Proc. Natl. Acad. Sci. USA*, 88:7953-7957 (1991).
Donovan et al., "Rapid Purification of Bacteriophage λ DNA", *BioTechniques*, 15:602:603 (1993).

Feng et al., "The mouse bone morphogenetic protein-4 gene: analysis of promoter utilization in fetal rat calvarial osteoblasts and regulation by COUP-TFI orphan receptor", *J. Biol. Chem.*, 270:28364-28373 (1995).
Fu et al., "Viral sequences enable efficient and tissue-specific expression of transgenes in Xenopus", *Nature Biotech.*, 16:253:257 (1998).
Gaussin et al., "Endocardial cushion and myocardial defects after cardiac myocyte-specific conditional deletion of the bone morphogenetic protein receptor ALK3", *Proc. Natl. Acad. Sci. USA*, 99:2878-2883 (2002).
Gong, Z. and Hew, C., "Transgenic Fish in Aquaculture and Developmental Biology", *Curr. Topics Dev. Biol.*, 30:177-214 (1995).
Hammerschmidt et al., "Genetic analysis of dorsoventral pattern formation in the zebrafish: requirement of a BMP-like ventralizing activity and its dorsal repressor", *Genes. Dev.*, 10:2452-2461 (1996).
Hogan, B., "Bone morphogenic proteins in development", *Curr. Opin. Genet. Dev.*, 6:432-438 (1996a).
Hogan, B., "Bone morphogenic proteins: multifunctional regulators of vertebrate development", *Curr. Opin. Genet. Dev.*, 10:1580-1594 (1996b).
Hsiao et al., "Enhanced Expression and Stable Transmission of Transgenes Flanked by Inverted Terminal Repeats From Adeno-Associated Virus in Zebrafish", *Dev. Dynam.*, 220:323-336 (2001).
Hu, et al., "Structure and Function of the Developing Zebrafish Heart", *Anatom. Rec.*, 260:148-157 (2000).
Hwang et al., "The Zebrafish BMP4 Gene: Sequence Analysis and Expression Pattern During Embryonic Development", *DNA Cell Biol.*, 16:1003-1011 (1997).
Jones et al., "Involvement of Bone Morphogenetic Protein-4 (BMP-4) and Vgr-1 in morphogenesis and neurogenesis in the mouse", *Development*, 111:531-542 (1991).
Ju et al., "Faithful Expression of Green Fluorescent Protein (GFP) in Transgenic Zebrafish Embryos Under Control of Zebrafish Gene Promoters", *Dev. Genet.*, 12:158-167 (1999).
Marini et al., "Presistence and Replication of Plasmid DNA Microinjected into Early Embryos of *Xenopus laevis*", *Dev. Biol.*, 127:421-434 (1988).
Martinez-Barbera et al., "Cloning and expression of three members of the zebrafish Bmp family: Bmp2a, Bmp2b and Bmp 4", *Gene*, 198:53-59 (1977).

(Continued)

*Primary Examiner*—David Guzo
*Assistant Examiner*—Michele K Joike
(74) *Attorney, Agent, or Firm*—Patterson & Sheridan, L.L.P.

(57) ABSTRACT

Embodiments of the invention generally provide isolated DNA molecules, tissue-specific expression sequences, and promoter and regulatory DNA sequences involved in the regulation of bone morphogenetic protein 4 (BMP4). More specifically, the invention relates to regulation of gene expression in a tissue-specific manner. In one aspect, the invention provides zebrafish BMP4 gene, its structural organization, its promoter, and proximal and distal regulatory regions. In another aspect, the invention provides methods for identifying potential compounds/agents, potential molecular regulators, and the expression pattern for the expression of BMP4 gene.

21 Claims, 9 Drawing Sheets

OTHER PUBLICATIONS

Mowbray et al., "Expression of BMP signalling pathway members in the developing zebrafish inner ear and lateral line", *Mechanisms of Development*, 108:179-184 (2001).

Muller et al., "Intronic enchancers control expression of zebrafish *sonic hedgehog* in floor plate and notochord", *Development*, 126:2103-2116 (1999).

Nikaido et al., "Conservation of BMP signaling in zebrafish mesoderm patterning", *Mechanisms of Development*, 61:75-88 (1997).

Ozkaynak et al., "Osteogenic Protein-2", *J. Biol. Chem*, 267:25220-25227 (1992).

Park et al., "Analysis of Upstream Elements in the *HuC* Promoter Leads to the Establishment of Transgenic Zebrafish with Fluorescent Neurons", *Dev. Bio.*, 227:279-293 (2000).

Schilling et al., "Regulation of Left-Right Asymmetries in the Zebrafish by *Shh* and *BMP4*", *Dev. Bio.*, 210:277-289 (1999).

Schultheiss et al., "A role for bone morphogenetic proteins in the induction of cardiac myogenesis", *Genes & Dev.*, 11:451-462 (1997).

Shafizadeh et al., "Transfenic Zebrafish Expressing Green Fluorescent Protein", *Methods in Molecular Biology*, 183:225-233, 1990.

Stuart et al., "Replication, integration and stable germ-line transmission of foreign sequences injected into early zebrafish embryos", *Development*, 103:403-412 (1988).

Stuart et al., "Stable lines of transgenic zebrafish exhibit reproductible patterns of transgene expression", *Development*, 109:577-584 (1990).

Van den Wijngaard et al., "Genomic Organization of the Human Bone Morphogenetic Protein-4 Gene: Molecular Basis for Multiple Transcripts", *Biochem. And BioPhys. Res. Comm.*, 219:789-794 (1996).

Yelon et al., "Patterning during organogenesis: genetic analysis of cardiac chamber formation", *Cell & Dev. Bio.*, 10:93-98 (1999).

NCBI database, AF056336, 2003.

NCBI database, NM_131342, 2003.

* cited by examiner

MIPGNRMLMVILLCQVLLGESSYASLIPEEGKKASALHLAQS
HELLRDFEATLLHMFGLQRRPRPSHSAVVPQYLLDLY
RLQSGELEEAGAQHVSFDYPERSTSRANTVRGFHHEEHLEE
LQSDGSQETPLRFVFNLSSIPEDELISTAELRVYRQQID
DAFSDPDQTGDHGLHRINIYEVLKAPREGQLITQLLDTRLVRH
NTSKWESFDVSPAVLRWTQEKRSNHGLAVEVVQMKRN
PVQKGRHVRVSRSVHPLPDEEWDQLRPLLVTFGHDGKSHPL
TRRAKRSPKQRGRKRNRNCRRHALYVDFSDVGWNDWIVA
PPGYQAYYCHGECPFPLADHLNSTNHAIVQTLVNSVNTNIPKA
CCVPTELSAISMLYLDETDRVVLKNYQEMVVEGGCGCRR

Fig. 2

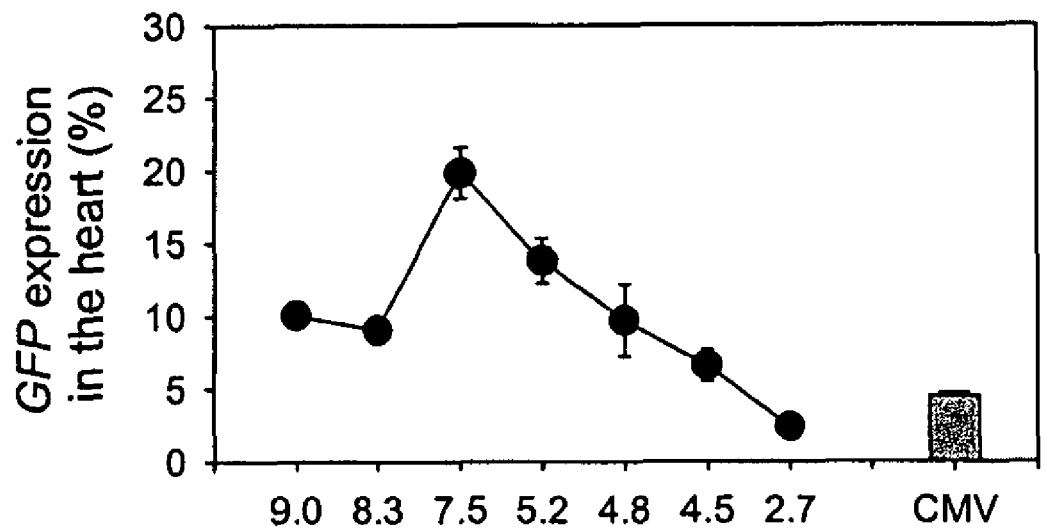
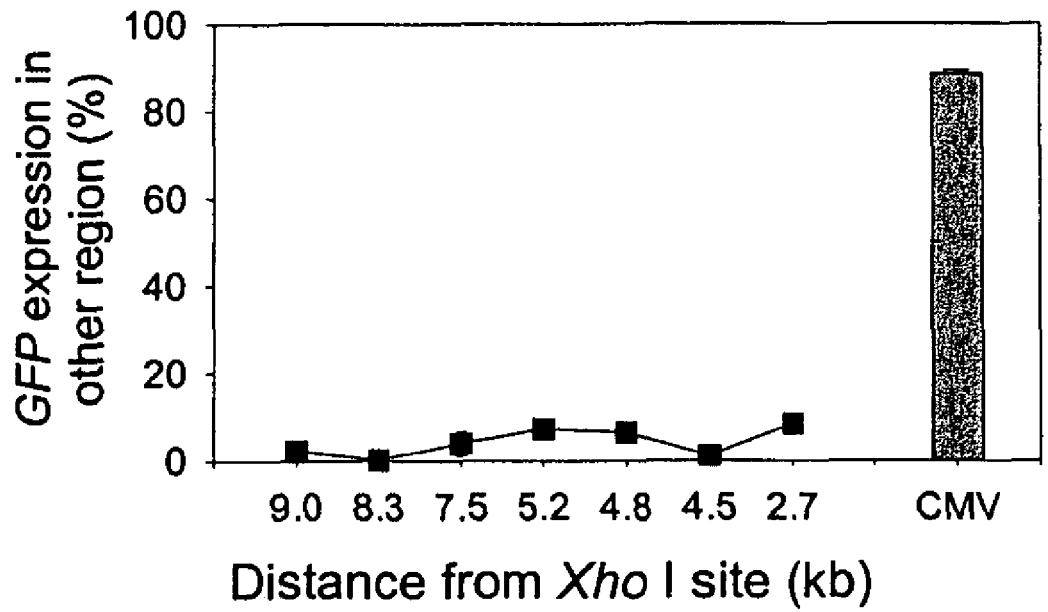
Fig. 7

SEQUENCE LISTING

```
<160> NUMBER OF SEQ ID NOS: 9

<210> SEQ ID NO 1
<211> LENGTH: 9100
<212> TYPE: DNA
<213> ORGANISM: Danio rerio
<300> PUBLICATION INFORMATION:
<308> DATABASE ACCESSION NUMBER: AY156927
<309> DATABASE ENTRY DATE: 2001-12-19

<400> SEQUENCE: 1
accggtggcg aggagcaaca cggccgtctt ctccagtgtg ggcgtcgagg aggacttgaa      60
atcaagtcaa cttaatggta atgagctatg acgcggttcg gcggcaagca atcagaatga     120
agtagtccac cgtttgagag gagttcagag aacgcagacc tgtgaacttt ggttccgacc     180
ccagttgttc ccagcggttt gattattgcg gttgccggat tttcaattat tgaaaatcgc     240
gaccacacgg ggtcccctaa tcacgcgggg cccctaatc acgcggggcc cccccgcgg      300 tggcccgtcc gcgacgccac ttgtgcttgg cattccctta acagtgcagt tcatgtggac     360
agatattttt ttaaacgaag acaggggaaa ctgtttataa aaatacctgt gcacgtgtag     420
acgtggccta aagctgattg tattggcgca ttctcttcat gcttgattca ttttgagtca     480
aaacaagtga ctgtcaattg cggtcgcttc agctcaaaca ctcaagcaga gtattttcat     540
ggtagtcgga ttgctacttg agcgatacgt ggattaattg tctctgtatt ttgtatatct     600
agtgaggtct gaagccgcga gtactgtgtt gtcctgccaa gggcccgtgg ttcacacaca     660
ctgagatgtt agcatattcc aactgcttgg aattccttcc cgccgtccgg agagcacaca     720
ctgtgtttta aaacttgttg ggcccttttca agttttattt gaaagtatgt aattacattc     780
ttgaaaaaat aacaggtctc tggagagatt tatattgagt attaaatgtc aaggtttgaa     840
aagacacggt taacgctcgc tcatccactt aagagcttct cgatggcctg aacagttaag     900 aggggtttaag gatatggatg tgcagtaaaa ataaatacac tgcggaaaaa gaaagaaagg     960
```

```
tagaggagcc ggagcacaaa cacaggtgca ggttggggct tccttaaaag ggctggcgag    1020
cttttttttt ttttttactt atgacttgtt ctgaagtttta gtcaaagcag gtcttgagtt   1080
taaggatcta gctttcatat ctgatggtct gaccctgaaa tctgattgaa gcacaagtct    1140
gatgtaaaaa aattatgctt attaagcatt tattttaata aatgtaattt ggctgttgac    1200
accgagcttt cattagcaaa aggacccatc tagttaaaat acactctcca gccactttat    1260
taggtacacc ttactagtac caggttggat tcccttttgc cttcagaact ggcttaatcc    1320
ttagattcaa caatgtactg gaaatattcc tcagagattt tgctccatgt tgacatgata    1380
gcatcacgca gttgctgcag atttgtcagc tgcacatcca tgatgccaat ctcccgttcc    1440
accacatccc aaagctgctc tattggattg agatctggtg actgtggagg ccatttgagt    1500
acagtgaact catcgtcatg ttcaagaaac cagtctgaga tgattcacgc tttatgaaat    1560
ggtgtgttat tctgctggaa gtagccatca aagatggag acactgtgct cataaaggga    1620
tggacatggt cagcaacaat actcaggtag gctgtgacgt tgacaccatg ctcaattggt    1680
actaatggac ccaaagtgtg tcaagaaaat ctcccccaca ccattacacc accaccacca    1740
gcctaaccca ttgatacaag gcaggatgga ttcatgcttt tatgttgttg aggccaaatt    1800
ctgacccgac catctgaatg tgtcagcaga aatggagact catcagagca ggcaacgttt    1860
ctccaatctt ctattgtcaa attttaaaga gagcctgtgc gaattgtagc cttagttttcc   1920 tgttcttagc tgacagaagt aagtaaagtg aatttatatg ttgcatttat cttgtatggc    1980
catacaacca aagtgcttca caatcatgag aaggggggtg ttcaacacgg catctacttg    2040
gatgttgtga cagcagccat aggacaacag caccagtgcg ctcaccacac accagctata    2100
gatggagtgg agagacagta atagatccaa ttcggtagat ggggatgatt aggaggccat    2160
gatgggtaaa ggctgattta tacttctgcg tcaaacaccg gcgtatacta cggcgctgac    2220
gcatagccct tcgccgtggc cgtcactgac gtgcacctct caaaaaatgt gactacacgt    2280
cgcaacaacg cgtagcgaaa gctctgtgat tggtcggctt ggtagcgctg acgagtcggg    2340
gcgggaccga gagccgtgcg aatggcgcga acccaatgga gcgattgttt acaaatgtgg    2400
agtcccgtga aggagctccg gatggaaagt tttgttttgt tgcacgtccg ccggttgctg    2460
cctcaaaatg agcgagtttg agtcacttgt acatcctgga agtgttcagg aaaagcaaaa    2520
ttgcagcgaa gaaactcgac acagaggaac atttacacct cactgcccac tagcgtttcg    2580
gaagtgttaa tgcagaccga cagagacagc gcgcagaagt ataaatgcac agccacgcac    2640
gttgcatgcc ccgtgggtta cgccggtcac ttgacgcaga agtataaatc tggctttagg    2700
gccgattgag ggaatttggc caggacactg ggttacaact gtactcttta tgagaagtgc    2760
catgggattt ttattgacca cagagagtct cggtttaatg tctcaaaacg gtgcccactg    2820
acagtatagt gtcccccttca ctttactcgg gacattagga ctccacatgt tgagcacccc   2880
ctgctggcct tactaacagc actttcaaca gcaacctagt ttgcccatgt ggtctcccat    2940
ccaggtactg accaggctca gaaacctgct tgttttttttg tactacaagc tgattggacg   3000
tagtaaagta ggcatttatt cagaaagatg gggaaaaggg tttggggaga gttattacaa    3060
cctaatagac tcctgctcac tatttcggtt tgttgtcaaa actgacagct ggaagggcgt    3120 ggctaaaatat gttagccccg ccctgtacct cagacattca cacgaggctg cagcgtcaac   3180
gcttgccaat gaaattagtc cacaatcggc tacagtctta gctggtgtat ttgcatacat    3240
cgacctaatt ggctgacgct tccaaaagtt gagcaagtcc caacttgtgc agtaagcacc    3300
gccactgaag ttgcgccgac gaatccacaa tgcagttcgg caatgcttga catcacccat    3360
```

-continued

```
tcaaactaaa taggaagtgt tgaagttgac gccccgtgtg aatgcggcgt taatctgaga    3420
atttaactga aaacaaacag gaagtgcatt tccagatttc aattttagat tacaaggcca    3480
aacaatttcg ttttttcttaa tggcatgcac agatgaattg ttgaccacaa agctagcaac    3540
gtgagctaag aaaatcaata tggttagttt tgattttgtg tgtactttaa cgtgagattg    3600 ttcccttttat ctatggactt agggcttatt cttttttacag tagttagtgt taattacaag    3660
tatattttga cagtaatttg gatttctctg ctcgatgttt aagtagatta agcgcttttc    3720
cccttaagcg cttttaaaatg tcccaatctt cagtgatgat tgcttgccga gtgtcattgc    3780
atcctctcag attaaaggag cgtttctgaa gtgccggtcc atctcctgat aataaaagct    3840
tttaaaccag tgctgaagtt tccctgtga ccgcagcttc tccacagaga gggtctggac    3900
aatgttgtgg tcggagtgtc ttcaaacact ttcagagctg cctaaaaaaa ggcctgcggt    3960
ccagcacact tcagcatcag ctccgataag tccgtccaca catcttctgc tcagatgcgg    4020
cagaggaaga gagataacac tgtttgtgtc tgagacgcgc atttggacat actgcactga    4080
agatacaagt gtgaagttgg gatacaggcc agaacacaga aaacatccca atgatttctg    4140
attattatca gtgatgatgt ttacatggac accaatactc ggatttaat atgattaaga    4200 caatactctg attaagggtt ctccatgtaa acagattttt gcaacccaag ctcattctgg    4260
aaacgtagcc ccgcggacgg ttctggagac cgcgatttac gtggccggag atacgtaaag    4320
gccgcgtttg tttttttttc gagcgaacac tgcggggcag tgtggtgccg atccacccct    4380
cctcttcgcg ctcgccggcc gacagctcgc ctccgagtgg agggctttcc caacgcaatc    4440
agtttgtccg cctagctcac atcgttgcgt cagcggagcg gaggccccgg aggaggagga    4500
cgacgacgag ccggagccgg ccgcggtgga cgacgaccgg gatcgtgtcc ggggaacggt    4560
gggttccgga aatcaggtaa gacgaaaaac ggaatccgga aaatgagggc cagaacgcgg    4620
cgggatccga aaacgcggtc gaaatcgaag acggggcgtt ttgcttttgt ttttttttt    4680 ttcgatccgg cggctattcg cgtgagaaca gcgctggcgc aaacgccgcg cgctcccgga    4740
tcggcgaaaa caaaaaaatc gctcgaatac gtacctcccg ggacgtaaat cgtggtccgc    4800
agaaaagtcc gcggggctac gtttccacaa tgagcccagg ttggattttt gatgaccgta    4860
atctgactca agtcataatc aaactaaaca gaaatggacc aaagcctcct ttccactgca    4920
cacgacaaac gatgagctgc gaatacgttg aaatatttga acttctgcga ctagatcgta    4980
tgcgacctgc cgaccaggtg tgatgaactt cagtgtgcgc gagatgataa atactgtttt    5040
ttcccgggtt tttttttagac tttttttttat cagaaaaatc gaattattgg tgtccatgta    5100
aacgtagcca ctgactacgc tttcattgac atcagtaatc aaattatttg ccttaatcta    5160
attaggcaat aaatatgatta atgcgttaca tgagctgctt tttgaatgtt cctttcatga    5220
tcccggttta catcttacag cacatatttc gattaacgtc atcgtgctgt ccacgtttcc    5280
tccagagttt tatgcaattt cgggtgtttc gttttttaatt tgtcgacttt aacttctgtt    5340
tgccactttc actttcattt aggaacataa ccccccgtgac aaatgaaata tttggtgcaa    5400
ctatgatctg ctggaagagt attgttttaa tggaatttca tacggcatgc tgaatagaag    5460
aaaaaaaaaa cacttctgta tttaaagggc attttattc attggtatag tggtatcaga    5520
agtagtaaag gtattgtagt attagtagtc agtagtatta gtagtagtag tagtagtcat    5580
cattgttggt gtagtagtat cagtagtaga tgttgtcgat gtagatgttg tagtagcagt    5640
gattgctgta gtaatatcag tagtagtagg ggtagtagat gttgttgttg aagtattagt    5700
tgtagtagac actgtagtag catcagtagt agtagttctt gtagtagtat cactattagt    5760
```

```
agacatagtg gttgtcgctg aagtagcagc agtagtagtt gtaatattaa taactttctg    5820
aagtagtagt tggtgtagca cttgtgattt attaatattt ttgttgtcat ttattattac    5880
tattgtcctt ccttctttttt gctgtcatta ttactatcat acattacttg cattgttgtt    5940
acttcttacc actgactggt ttctttctat ctgttttatt catatctgtg atacttgatt    6000
cacttattga ctgttattgt cccttatgta tgtactataa cctgtccaca aagttacctt    6060
tacacacaca cacacacatg catgcaccta ccagtacctg actattattg tttttgtttc    6120
gttttttgtt gttttttgttg atgtttcttt gtactgatat gatcccaatt tatgtacctt    6180
tttgcatatt ctaataaaaa ataaaaataa ataaaaataa atcatgggct taatgcatca    6240
caaatagcac aaatattaca cacacacaca cacacacaca cacatatata tatatatata    6300
tatatatata tatatatata tatatattgt ggtcatgatt ttcaaaagta ttactttgct    6360
ttgtaaatgt ttattattac attttggtga gtctccctgt acagtttgat agagcacttg    6420
gagcactaga agttgctttg tatgatgtca catataacaa tcggtacaca tgtccacaga    6480 acctttttttt tgccaataaa ctgggtttaa aatatttgtt acaacactct gtgattttga    6540
tgagtttaaa acgttttaaa agcagagcat gtttgtaata aagacagtaa aactgctaaa    6600
aaaggggggg gggggggca ttttaacaaa aaaaggactt tgcggtaagg ctattttact    6660
gtaaaatgga attgcagtag agctctgcaa ttgtaaaaca catttacagg caggttactg    6720
taaaggggca gttgaggtaa attgctagca acagtgctgc cagtaagtta ataaaataca    6780
gtgctgaatt gtggctgcat aaaacatatg ctggaacagt tggcagttca ttccactgtg    6840
gcaaccgctg ataaataaga gactaagctc taggaaaata aattaataaa taaatgttta    6900
tttcagaaca ggattacgcc acaaataaat gtttctctga atgtatgggg gtgaccgtat    6960
gtttggggga gggtaaaccg gctctcagta cccagacagg taaataatat ggtaatgagt    7020
gtgtctgcgt gagcttcttc acacactggg acttaattgt tattataggg gcgggaggtc    7080
aaacggagaa gacgtccagc cctgatgaag gacaataaga ggaaacattc actgatctcc    7140
actgacacaa tgaagattaa tgcgcagagc gaaaagtctt attagaagct gtttccacaa    7200
aagatgatcc agcctatcca gtgttacttg caaaaactag attagttcat gtaagcagat    7260
ttttgatagg ttaaaaagag tcatgaatta tttaatttag tattttagat aaagatagag    7320
tgatttcaga ttatgcttaa agctcatttta ttaagacaat atttggctga gatacaagta    7380
tttggaaatc tgcaatttga gggttcaaaa caaaagtaaa aaatgaaaat actgagaaaa    7440
tctactttga agttgtccaa ataaatttct caacaattac taataataaa aggttcaaca    7500 aaaggggggtt cagtttattc ataacaattt gcttttgtat tattatttgc actccgttat    7560
tattgttcat ttattcgttt gctggaaatt agaactgaat ttagaaatag ttttgaaaca    7620
aatctttgcg cttaacaaac taaactaatt atgtataggc taatagatgt cagtgcgtac    7680
aacaactttc cctattcacg agagtaaaag tagagaatta ggaggctcat tctctcattc    7740
ttgcgctgca gatactctaa ctgtttctc tctagggaag tgttcagttt ttccacttac    7800
aaagtccgcc atgtaaatag caaatgtgca ataaagcaat gcaactggct tttaaaggga    7860
atgggagatg agactctgat tggtttattc tcaaaacaca cctataactc gttcagagaa    7920
taagctcaac cctgttagac catgcgccac agtgcaaagc agattttttcc gtccttaaaa    7980 tagtaaagtg gattctggca tgctcttatt gcttttgcac cctgcgcttt agactttgcg    8040
catggattgt caaaatagag cccgtcgtga tttatattgt gtattgaaaa gtaaaattgc    8100
aaataaaaat aaaaaaaaac atggtttacg gaaattacta aaactggaga tttagtagtt    8160
```

-continued

```
ttcagaaatc gtgatttta attaatattg aagatttcaa aagcaaaaaa aaaactaatt     8220
aaacaaatta tgtgaacaaa acatttaaat aaccttttca tatatcaccc ttttaaaata    8280
tacgactgtt atgagatggc ggcaattttt taatattcag actcattatc tgcattaaaa    8340
agtttagcgg tgattaaaga gatcatcttc aagacaggac tttctgtatg aaattagtac    8400
aaaatctata ctaaaatcaa agagaaacac aagtcacatt ttaatgaata cctcctcgtg    8460
cacagttgag gtaaatgagg ggcaaagaaa agctgttatc atttaacttt gtttacttca    8520
cagtcaattt attggtgaag ggactaattg aatatgccta ttgatggaag gtttgcaaag    8580
aattgtcatg ctcccttgta aaagtatttt gtagtatttt caaaatacaa tattttattt    8640
tgatatactt gtggctgctg tattttgtag tttaatttga taaacttaaa atggaagtat    8700
ttgatatatt tttaatacat tttaatggat ttttgcccat ccctgactgt gtatgtatgc    8760 gcttttaat gtcaacttta taaacgcttt agcaatacat ttgtcatgcc aataaagcag     8820
ttatttaaat tgaaattgag agagagagag agagagagag agagagagag agagagagag    8880
agagagagta tgggaggagg aaaagcggag caaagcagct ccataagggc ggtcacataa    8940
aacctgcctg ccgaactgga tgcgggtcac tcggtgatgt cctcagtcct gttctcgagt    9000
gttctaggag ctacagccac ccgcctttac actggactca ggttttcttc ttctacgtga    9060
tgcggaacta ataacctaag cagtgccttc aaaggttgga                          9100
```

```
<210> SEQ ID NO 2
<211> LENGTH: 1790
<212> TYPE: DNA
<213> ORGANISM: Danio rerio
<220> FEATURE:
<221> NAME/KEY: CDS
<222> LOCATION: (8)..(1210)
<223> OTHER INFORMATION:
<220> FEATURE:
<221> NAME/KEY: misc_feature
<222> LOCATION: (416)..(424)
<223> OTHER INFORMATION: N-linked glycosylation site
<220> FEATURE:
<221> NAME/KEY: misc_feature
<222> LOCATION: (119)..(826)
<223> OTHER INFORMATION: TGFb_propeptide; TGF-beta propeptide; this
      propeptide is known as latentcy associsted peptide (LAP) in
      TGF-beta; LAP is a homodimer which is disulfide linked to TGF-beta
      binding protein;
<220> FEATURE:
<221> NAME/KEY: misc_feature
<222> LOCATION: (617)..(625)
<223> OTHER INFORMATION: N-linked glycosylation site
<220> FEATURE:
<221> NAME/KEY: misc_feature
<222> LOCATION: (914)..(1207)
<223> OTHER INFORMATION: TGF-beta; Transforming growth factor beta like
      domain;
<220> FEATURE:
<221> NAME/KEY: misc_feature
<222> LOCATION: (1031)..(1039)
<223> OTHER INFORMATION: N-linked glycosylation site
<300> PUBLICATION INFORMATION:
<301> AUTHORS: Hwang,S.P., Tsou,M.F., Lin,Y.C. and Liu,C.H.
<302> TITLE: The zebrafish BMP4 gene: sequence analysis and expression
      pattern during embryonic development
<303> JOURNAL: DNA Cell Biol.
<304> VOLUME: 16
<305> ISSUE: 8
<306> PAGES: 1003-1011
<307> DATE: 1997
<308> DATABASE ACCESSION NUMBER: NM_131342
<309> DATABASE ENTRY DATE: 1998-03-30
<300> PUBLICATION INFORMATION:
<308> DATABASE ACCESSION NUMBER: NM_131342
<309> DATABASE ENTRY DATE: 1998-03-30
```

<400> SEQUENCE: 2

```
agacatc atg att cct ggt aat cga atg ctg atg gtc att tta tta tgc        49
        Met Ile Pro Gly Asn Arg Met Leu Met Val Ile Leu Leu Cys
        1               5                   10 caa gtc cta ctg gga gaa agc agc tat gct agt ctg ata ccc gag gaa        97
Gln Val Leu Leu Gly Glu Ser Ser Tyr Ala Ser Leu Ile Pro Glu Glu
15                  20                  25                  30 ggg aag aag aaa gcg tcg gct ctt cac ctg gct cag agt cat gag ctg       145
Gly Lys Lys Lys Ala Ser Ala Leu His Leu Ala Gln Ser His Glu Leu
                35                  40                  45 ctg cgg gac ttt gaa gcc acg ctg ctg cac atg ttt ggc ctg cag agg       193
Leu Arg Asp Phe Glu Ala Thr Leu Leu His Met Phe Gly Leu Gln Arg
            50                  55                  60 cgt ccc aga ccc agc cac agc gcc gtc gta cca cag tat ctg ctc gac       241
Arg Pro Arg Pro Ser His Ser Ala Val Val Pro Gln Tyr Leu Leu Asp
        65                  70                  75 ctc tac cgc ctg cag tcg ggg gag ctg gag gag gca gga gcg cag cac       289
Leu Tyr Arg Leu Gln Ser Gly Glu Leu Glu Glu Ala Gly Ala Gln His
    80                  85                  90 gtc agc ttc gac tat cct gaa aga tcc acc agt cga gcc aac acc gtg       337
Val Ser Phe Asp Tyr Pro Glu Arg Ser Thr Ser Arg Ala Asn Thr Val
95                  100                 105                 110 aga gga ttc cat cat gaa gag cac ctg gag gag ctg cag tca gac ggc       385
Arg Gly Phe His His Glu Glu His Leu Glu Glu Leu Gln Ser Asp Gly
                115                 120                 125 tcc cag gag act cct ctg cga ttt gtt ttt aat ctc agc agc atc cca       433
Ser Gln Glu Thr Pro Leu Arg Phe Val Phe Asn Leu Ser Ser Ile Pro
            130                 135                 140 gag gac gaa ctc ata tcc acc gca gag ctt cgc gtc tac agg caa caa       481
Glu Asp Glu Leu Ile Ser Thr Ala Glu Leu Arg Val Tyr Arg Gln Gln
        145                 150                 155 ata gat gac gcc ttc tca gac cca gat caa aca ggg gac cat ggt ttg       529
Ile Asp Asp Ala Phe Ser Asp Pro Asp Gln Thr Gly Asp His Gly Leu
    160                 165                 170 cat cgg ata aac ata tat gag gtg tta aag gcg cca cgg gaa gga cag       577
His Arg Ile Asn Ile Tyr Glu Val Leu Lys Ala Pro Arg Glu Gly Gln
175                 180                 185                 190 ctc atc acg cag ctc ctg gac aca cgt ttg gtg agg cac aac acc tcc       625
Leu Ile Thr Gln Leu Leu Asp Thr Arg Leu Val Arg His Asn Thr Ser
                195                 200                 205 aaa tgg gaa agt ttc gac gtt agc cct gca gtg ttg cgc tgg acc caa       673
Lys Trp Glu Ser Phe Asp Val Ser Pro Ala Val Leu Arg Trp Thr Gln
            210                 215                 220 gaa aaa cgc tct aat cat ggc ctt gct gtg gag gtt gta caa atg aag       721
Glu Lys Arg Ser Asn His Gly Leu Ala Val Glu Val Val Gln Met Lys
        225                 230                 235 cga aac cca gtt caa aag gga cga cat gtt cgt gta agt cgc tcc gtg       769
Arg Asn Pro Val Gln Lys Gly Arg His Val Arg Val Ser Arg Ser Val
    240                 245                 250 cat cct ctt ccg gat gaa gag tgg gac cag cta cgc ccc ctg ctg gtc       817
His Pro Leu Pro Asp Glu Glu Trp Asp Gln Leu Arg Pro Leu Leu Val
255                 260                 265                 270 aca ttc gga cat gac ggc aaa agt cac ccg ctg act cgg cga gcg aaa       865
Thr Phe Gly His Asp Gly Lys Ser His Pro Leu Thr Arg Arg Ala Lys
                275                 280                 285 cgc agc cct aaa caa aga ggt cga aag cgt aat cgt aac tgc cgg aga       913
Arg Ser Pro Lys Gln Arg Gly Arg Lys Arg Asn Arg Asn Cys Arg Arg
            290                 295                 300
```

```
cat gcg ctg tat gtg gat ttc agt gac gta ggc tgg aac gac tgg att      961
His Ala Leu Tyr Val Asp Phe Ser Asp Val Gly Trp Asn Asp Trp Ile
            305                 310                 315 gtg gca ccg cct gga tat cag gcg tat tac tgt cat gga gag tgt ccc     1009
Val Ala Pro Pro Gly Tyr Gln Ala Tyr Tyr Cys His Gly Glu Cys Pro
320                 325                 330 ttt cca tta gcc gat cat ctc aac tcc acc aat cac gct atc gta cag     1057
Phe Pro Leu Ala Asp His Leu Asn Ser Thr Asn His Ala Ile Val Gln
335                 340                 345                 350 aca ctg gtg aac tcg gtg aac acc aat atc ccc aaa gcc tgc tgc gtg     1105
Thr Leu Val Asn Ser Val Asn Thr Asn Ile Pro Lys Ala Cys Cys Val
            355                 360                 365 ccc act gag ctc agc gca atc tcc atg ctt tac ctg gac gaa acg gac     1153
Pro Thr Glu Leu Ser Ala Ile Ser Met Leu Tyr Leu Asp Glu Thr Asp
        370                 375                 380 agg gtg gtg ctg aaa aac tat cag gag atg gtg gtc gag ggg tgt ggc     1201
Arg Val Val Leu Lys Asn Tyr Gln Glu Met Val Val Glu Gly Cys Gly
            385                 390                 395 tgc cgc taa acggagactc ttaccacaaa acatccaca cgtggacact              1250
Cys Arg
    400 tatttataac ttgtgtttgt catttcttgt ctgatcgatc atatattttg acagaaagta   1310 tatatatata aatatatatt tatatcggtg tagtaaaaaa taaataaaat gaaagtgtcc   1370 ttatttgaat tatataattc agctttccat aatgtatatc agactgtata aggttttttc   1430 tatatggagc cagatcagtc tcaaaaatta tacatttaca aaataaattt catacgctca   1490 caacaaaatt atcatttaca aaatccaatt cgtgaattca aaacacgatt cgtaaataca   1550 caaacacaat tagtaaattc aaaacaaaat taaaaaatgc tcaaattcaa ttcgttaatt   1610 gaaaacacaa tttgtaaata tacaaagcca attcgtaaat tcaaacgct ttttgtaaat   1670 acacaaatcc aattttgtaa agtcaatacg atttgaaaat acacaaatcc aattcgtgaa   1730 ttcaaaacac tattcgtaaa tgcacaaatt caattctaaa ttcaaacgtg attcgtaaat   1790

<210> SEQ ID NO 3
<211> LENGTH: 400
<212> TYPE: PRT
<213> ORGANISM: Danio rerio

<400> SEQUENCE: 3

Met Ile Pro Gly Asn Arg Met Leu Met Val Ile Leu Leu Cys Gln Val
1               5                   10                  15

Leu Leu Gly Glu Ser Ser Tyr Ala Ser Leu Ile Pro Glu Glu Gly Lys
            20                  25                  30

Lys Lys Ala Ser Ala Leu His Leu Ala Gln Ser His Glu Leu Leu Arg
        35                  40                  45

Asp Phe Glu Ala Thr Leu Leu His Met Phe Gly Leu Gln Arg Arg Pro
    50                  55                  60

Arg Pro Ser His Ser Ala Val Val Pro Gln Tyr Leu Leu Asp Leu Tyr
65                  70                  75                  80

Arg Leu Gln Ser Gly Glu Leu Glu Glu Ala Gly Ala Gln His Val Ser
            85                  90                  95

Phe Asp Tyr Pro Glu Arg Ser Thr Ser Arg Ala Asn Thr Val Arg Gly
            100                 105                 110

Phe His His Glu Glu His Leu Glu Glu Leu Gln Ser Asp Gly Ser Gln
        115                 120                 125
```

```
Glu Thr Pro Leu Arg Phe Val Phe Asn Leu Ser Ser Ile Pro Glu Asp
            130                 135                 140

Glu Leu Ile Ser Thr Ala Glu Leu Arg Val Tyr Arg Gln Gln Ile Asp
145                 150                 155                 160

Asp Ala Phe Ser Asp Pro Asp Gln Thr Gly Asp His Gly Leu His Arg
                165                 170                 175

Ile Asn Ile Tyr Glu Val Leu Lys Ala Pro Arg Glu Gly Gln Leu Ile
            180                 185                 190

Thr Gln Leu Leu Asp Thr Arg Leu Val Arg His Asn Thr Ser Lys Trp
            195                 200                 205

Glu Ser Phe Asp Val Ser Pro Ala Val Leu Arg Trp Thr Gln Glu Lys
210                 215                 220

Arg Ser Asn His Gly Leu Ala Val Glu Val Val Gln Met Lys Arg Asn
225                 230                 235                 240

Pro Val Gln Lys Gly Arg His Val Arg Val Ser Arg Ser Val His Pro
                245                 250                 255

Leu Pro Asp Glu Glu Trp Asp Gln Leu Arg Pro Leu Leu Val Thr Phe
            260                 265                 270

Gly His Asp Gly Lys Ser His Pro Leu Thr Arg Arg Ala Lys Arg Ser
            275                 280                 285

Pro Lys Gln Arg Gly Arg Lys Arg Asn Arg Asn Cys Arg Arg His Ala
290                 295                 300

Leu Tyr Val Asp Phe Ser Asp Val Gly Trp Asn Asp Trp Ile Val Ala
305                 310                 315                 320

Pro Pro Gly Tyr Gln Ala Tyr Tyr Cys His Gly Glu Cys Pro Phe Pro
                325                 330                 335

Leu Ala Asp His Leu Asn Ser Thr Asn His Ala Ile Val Gln Thr Leu
            340                 345                 350

Val Asn Ser Val Asn Thr Asn Ile Pro Lys Ala Cys Cys Val Pro Thr
            355                 360                 365

Glu Leu Ser Ala Ile Ser Met Leu Tyr Leu Asp Glu Thr Asp Arg Val
370                 375                 380

Val Leu Lys Asn Tyr Gln Glu Met Val Val Glu Gly Cys Gly Cys Arg
385                 390                 395                 400

<210> SEQ ID NO 4
<211> LENGTH: 13382
<212> TYPE: DNA
<213> ORGANISM: Danio rerio
<220> FEATURE:
<221> NAME/KEY: gene
<222> LOCATION: (2630)..(13382)
<223> OTHER INFORMATION:
<220> FEATURE:
<221> NAME/KEY: mRNA
<222> LOCATION: (2630)..(2985)
<223> OTHER INFORMATION:
<220> FEATURE:
<221> NAME/KEY: mRNA
<222> LOCATION: (11949)..(13382)
<223> OTHER INFORMATION:
<220> FEATURE:
<221> NAME/KEY: CDS
<222> LOCATION: (2637)..(2984)
<223> OTHER INFORMATION:
<220> FEATURE:
<221> NAME/KEY: CDS
<222> LOCATION: (11948)..(12802)
<223> OTHER INFORMATION:
```

```
<220> FEATURE:
<221> NAME/KEY: misc_feature
<222> LOCATION: (12008)..(12016)
<223> OTHER INFORMATION: N-linked glycosylation site
<220> FEATURE:
<221> NAME/KEY: misc_feature
<222> LOCATION: (12209)..(12217)
<223> OTHER INFORMATION: N-linked glycosylation site
<220> FEATURE:
<221> NAME/KEY: misc_feature
<222> LOCATION: (12623)..(12631)
<223> OTHER INFORMATION: N-linked glycosylation site
<300> PUBLICATION INFORMATION:
<301> AUTHORS: Hwang,S.P., Tsou,M.F., Lin,Y.C. and Liu,C.H.
<302> TITLE: The zebrafish BMP4 gene: sequence analysis and expression
      pattern during embryonic development
<303> JOURNAL: DNA Cell Biol.
<304> VOLUME: 16
<305> ISSUE: 8
<306> PAGES: 1003-1011
<307> DATE: 1997
<308> DATABASE ACCESSION NUMBER: AF056336
<309> DATABASE ENTRY DATE: 1998-03-30
<313> RELEVANT RESIDUES: (1)..(13382)
<300> PUBLICATION INFORMATION:
<308> DATABASE ACCESSION NUMBER: AF056336
<309> DATABASE ENTRY DATE: 1998-03-30

<400> SEQUENCE: 4
gatcattaat attaataagt acgctatttt cattcattca ttcatttct tatcggctta      60 gtcccttat taatctgttg tcatttgaac cctttagacc ttttccaatt tttagactga    120
catgagagtg aatcgattat atttctatta tactttggaa atgattctt taaacacgca    180 cactcttttc aatgtgttgt taaaaaacac tacgcaaata cgtccacact atattttctt    240
tagctgtaac taaagaaaag tctaagacta ttttggtgt tttaaatttc atgtttaatt    300
gaacttgtcc cttgctttgt cattacaatt gcttgtctaa acaaaatgg acgtaaggta    360 gattctacca cagttttgtt tgttgttgcg ttctaaagcg tcacatgcat ttcagactgt    420
tttaaattag tttaacacca tgttcgtggc ccattgactt ccattataat aagatttttt    480
gattgcaaag ccataaaatc ttgcattttt tgattgttgg tgattttcc ctgtttggaa    540 aaagtaaaag ttgtaatttt tactgttgat catcagttgg cagccttaac cctttagata    600
ggcctgtgca aaacaagttt ttgtcttttt tacatgttca gtggagtaaa acagcagatt    660
atagtgtgat tgcatataca cacttactat gtttactatg ttctaagagc tgagcatgct    720
taaatgtctc tctataatgg ctcactataa tccaaatagc tcaattcacc ttattcttcg    780
atgacgagca agcgcagcca tttgatttct tttttttttt ggcttgagcc ttcctgtctc    840
attcacttcc attcattttt agatattaaa aactgcttgt tttgctgttt aatgttgcaa    900 actgatatt tcttattatt ttattaaact tggtctggat agtcatgcaa acatttgttt    960
gtagcgcaaa tagttttact gttttctgcc gtttattgtt cctagtcatt tctcccatag   1020
gcgactgaat ctgaagttct aaaacaatca cgaaaaaagg ccatgttgta aggtcaatgt   1080
aaagccagca actaatgatc aaaagcaaaa aaaattaca catttttccca acagggaaaa   1140 ccagcaacag ttaagggcgt actcgcacta tgctatccga actgtgccca ggccaccctg   1200
aatggccgcc ctgcgctgaa tcgggctcag gcacggccgg ccctggccca gttggaagag   1260
atgggcctga gcacggttca cttgggcttt ggtgcggtac gcttgtgtgt gagtgcaaag   1320
ggcgccaaag cccgaaactg aaagcgagac gtgacttta agggactgtt tcatatggat   1380
ttattaatca ttcttactat tcaatgaacg caaactgccg tagattatta aagacgaaaa   1440
cccctcactg catgacagct gcaccttcag cagacctcct cattcctgca gcacgaggac   1500
```

-continued

```
tttatgattt ttaataagcg tcatgggggg gagcatgctc tggcccggtt taaagcaact   1560
gtacatagtg tgagtacagc ctaagaatac acaatactat ggtgtcaagg ctttgcattt   1620
taaaaatgtc attttaatgg aagtcaatgg ggcaaaaaca gcccgaaaca cagcaaaaga   1680
gtagtacatt agctgacagt gcattgagtt tttgaataat ttcaaagcat ttttacaaaa   1740
tatgtgtcaa ataagatttt gtctccaaaa atcacacaat ttgctgaaac acagtgagag   1800
ttgtggccaa attaagactt aaaatcacct caaaaaactc ctgatcagat tgctaaagta   1860
gtgcaggtaa aaatgtggtt gaatgtgttt gaatagtcac gaaaggagaa aaaaatcaca   1920
cagattatga ttaaaatctt catttgaatg cttttcactt gtttgcttac cggcaaaagc   1980
gaaatgtcct cacacagcag atttgaaaga cgccggcgct tcctcgtact gttgcctcag   2040
cctcacttca ccgccactcg ccatgttaaa gtgtagaatg atggtcaagc ccccccaaac   2100
ttatagcaca gtgattggat atttgctcac ggggaggagt ttcctcatct cagctcatgg   2160
acttacaggc acacacataa attatttaaa cgcaaaggag agaaaaccgc aattcacaag   2220
cgcgtattga accatggagg tcgtacccta cctttttttc attataaata tatatatata   2280
tatatatata tatatacata cacatataca tatatatata tttatattta aatatatata   2340
tatatttatt tatttatttta tttatttata atgaaaaaaa taggagacaa ttttttaaata   2400 ggaaaagaaa aagaaaaaga aaattaattc actgtttaaa cctggtaacc tggttgcttt   2460
taatgtataa atccaaaagg tctgtctctc tgttttttaaa atttgaatct gtctcctctg   2520
cttgtatcta cggatatgtt ctacactgtt tctttgtatt tgtattgaag ctaatgcctc   2580
aaagtcatcc ttgctttttt gtttcccatg ttttcggcct gtccaccaga gacatc atg   2639
                                                                Met
                                                                 1 att cct ggt aat cga atg ctg atg gtc att tta tta tgc caa gtc cta    2687
Ile Pro Gly Asn Arg Met Leu Met Val Ile Leu Leu Cys Gln Val Leu
        5                  10                  15 ctg gga gaa agc agc tat gct agt ctg ata ccc gag gaa ggg aag aag    2735
Leu Gly Glu Ser Ser Tyr Ala Ser Leu Ile Pro Glu Glu Gly Lys Lys
     20                  25                  30 aaa gcg tcg gct ctt cac ctg gct cag agt cat gag ctg ctg cgg gac    2783
Lys Ala Ser Ala Leu His Leu Ala Gln Ser His Glu Leu Leu Arg Asp
 35                  40                  45 ttt gaa gcc acg ctg ctg cac atg ttt ggc ctg cag agg cgt ccc aga    2831
Phe Glu Ala Thr Leu Leu His Met Phe Gly Leu Gln Arg Arg Pro Arg
 50                  55                  60                  65 ccc agc cac agc gcc gtc gta cca cag tat ctg ctc gac ctc tac cgc    2879
Pro Ser His Ser Ala Val Val Pro Gln Tyr Leu Leu Asp Leu Tyr Arg
         70                  75                  80 ctg cag tcg ggg gag ctg gag gag gca gga gcg cag cac gtc agc ttc    2927
Leu Gln Ser Gly Glu Leu Glu Glu Ala Gly Ala Gln His Val Ser Phe
             85                  90                  95 gac tat cct gaa aga tcc acc agt cga gcc aac acc gtg aga gga ttc    2975
Asp Tyr Pro Glu Arg Ser Thr Ser Arg Ala Asn Thr Val Arg Gly Phe
            100                 105                 110 cat cat gaa ggtcagacaa tcaaacacca catcaaagt gcatttgtca              3024
His His Glu
    115 ttcttgcttt aagggggtttg ttcactcgaa aatgaaaatt ctgttattaa ttattgacac   3084 ttatgtcatt tcaattccac gagaccttt gattcatttt ttgtaactag aatttatcca   3144 ttcagacctt aattttgagt tcttaatgag ttctctgttc ttaaaggtgc tctgaagttt   3204 gacacacagt ggttaaacta ggtatagact gatttcacgt ggccgccatt ttcaaaagcg   3264
```

-continued

```
aaatcgaggc tgcggtggga agaaaaccgg aagtatcatt gggagttaca taggaatgtt  3324
gtgtaactgg ctatatatct tatcagcgaa gagaaagtga cacaaattta tcatttcttt  3384
accttccggg tgacctgaag gtccgttctg aatgaatggt gaatgtaaaa agggatatca  3444
gagctcattt tcagctaaat taagggaaat ggcactagtt agctaacgtt ttctttccca  3504
aacacacgtt ttagatgccg tttatcaaac tcgagttaat aaactgattc tttcactatg  3564
ttagacttgt cacgatactg aattaaaaga aaaaccggca atttcgcgct aacatttaag  3624
gcactgttga tggcttttctt aaaacagtgc tgatttgcca ttgtggtcac gtgtttaaca  3684
gaaatgattg tgattggccg agaaggtcat cagttcaccc accgctgtat actgagctcg  3744
actgatcttg acggctgctt cgcggtccag tccgtgtatc tgtgtttgta ctgggtgaag  3804
agcggtaaac tgagtgcaaa ccaaacagat acatggagac ggaagcgcga agcggtgaag  3864
atcagtcgtg tcgagacacc cgcttagcag cgcttccatg ttagcgggga aatagccggg  3924
tttaaaactg cagtgtttta tcactcaccg ggttacatag actgaagcag gaaagcgtcc  3984
tcacagtgtt taactgatgc catgagctga agcctgggac acttatgccg agttcagact  4044
gcatgatttt caaactagtc gtgtcacaga tgttttcaca ctgcatgact atctgggcta  4104
gcgtttcgtc gctgctttgt ttacactgca agatggttgg cgacatggcc attcacattg  4164
catgacttta ctataggaag aatcgccgac aacttcgtcc aaactacgtc tcacagccaa  4224
aaacatgtag tatatctttt aactacataa tgagaaagaa gcctttaatg gggtagaaca  4284
tgtacatgtt tgctcacctg ggtttgacgg gaattagcca tttctcctca acgttgataa  4344
taaactaatt tctttctgta tgaaacgtca acagacacg gttgctcctg agtcctgtca  4404
aacctccact agttttttcct ccatttcgtg ggtccaaata aaccgaaaaa gagcgtatac  4464
acacacacac acgcgcacac aagggaaagc tgctctctca ttggctgtag gcgatcgctg  4524
atgttatttt cagtcaaaac tcaatacaca cggcatgatt tgaatcgccg acagctccag  4584
atattcagca cgccaaatat ctcacaggca tcggcgactc atcggcgatt ctctcagatc  4644
gcgtctttga tcgttcatac tgtgtgattg tcactcacgt gcacgagcag cgatttgcct  4704
gtgatgcctg tgcctgaaca tttgtcggcg atttctcaaa acctgtcggc gagccaaaat  4764
cggggctaaa atcacgcagt ctgaactagg cattaagcgc atcactgaga ttgtgatctt  4824
gtttgatgct aaattgcttt taattgttta aaataaactt actgaataat attaaagtga  4884
tggttactcc attttctgca ttttgaaatc tcggcaacag ctggaggttt atagtacacg  4944
gcatgttact gcaatgttta cagtgttcgt cctatacttc cgggtttctt cccaccgcag  5004
cctcgctttg gttctttaaa atggcagccg cgtgaaataa gcgtactgca cacctggttt  5064
aaaaccattt cgcaggtcag agttcaccaa gcttgaacag caacctgcaa aactcgacgc  5124
atgactctgc atttccggtc tgacgcattc ccgtgcgtat gaatagaagt ctatgggagg  5184
aaaagcccag tgtgaccgca gcttaatgct gtgttcacac cagtcgaagc atcaagcgcg  5244
agtgatttac atttaagtc aatgcaaacg cgcgaataga catcctgcgg tgcaaattaa  5304
gcgctttgca tgtttgacgt gcttaaaaaa aatcgtaact aatgcggaca ttctcactgt  5364
gtgaaccaat caggagcttg ctcttgttgg ggcctgattt tcacgtagcg cctgttgtta  5424
gggtcccggg ggaaatcctt tagccgaaac cgacaacagt tcatcaaact gggctcggct  5484
gagtcagaag caccgctgaa agcctccatc atccaggttc agtttctgaa ggagtttatg  5544
agcttacaga gctgggtgca cctctgaaag gatctagtag actctgacac agccctaaac  5604
atattgacgc tgtatttcag ctttaattaa gcacacaaac actgttattt tcttactaaa  5664
```

```
atttatgtta gccatttagc aacgaagcta gagtcgaatc gaatgaagcg gatttgacgt    5724
gcgaatgaac cagggcttaa tgcgcgaata aatcgagtaa actcaaatct tcaggctgct    5784
atttgcgcgc gatttatcca cgcgtttctc atctggtgtg aacacagcat aaggtaaata    5844
agaaaataaa agctaagggg catgatagaa ggaatatttt catgttggag tttttgtcca    5904
aacaaacacc tgaagattat attcagaaca tcagaaaact gacaatgatc aggtcaggta    5964 caccctcacgt gctttactca gtgttaaatg ctaataatgt gagtttaaac gctattttac    6024
atgacattta tagccatata ctgaaagcag cagcagatag ctcacctaag atcttgaaaa    6084
taaaccgtct gaaattgaac tttagagctg tgactgtaac acacatcagt tcagcatcta    6144
cgtttaatca tgttaaagag gtttaatgtg tattcattag attataaacc ttactatgtc    6204
gttggagtgc agtgagtgca ctattctgtg ctttctgaat ggctgtattt acatttctgt    6264
cgggtttcgt ctggcgcaaa cagccaaatt gcttatcccg tattgtgttg ttaggacgcg    6324
gggttacaat gtagcctgct cccctaatgt ttacattcaa aatatttata ttatttgcta    6384
tttaataacc tcctcatgtg gaactctgaa tctgcttctc atttaagagt gctactgtcc    6444
accagaggtc gcatttcagt cgctgatgca taccttgaga gccttcctga ctgaatgaat    6504
gaaacatgcg gtttagttat atttaaaact aaattcagtc atttaatcgg aataatttag    6564
actgataaca atttaataag cgacttctat agcattatta tgctgcgtaa gaggcaagta    6624
tctgcatcta aagttgaatt agataataca ttcatttaca taacaattaa agtggcaaaa    6684
tttaatagga ttcaattcaa atgtaaccct ctgatcacaa gggtgattga caaaatgata    6744
gttggatttt agaaaatgcc agcaggtggc agcaagtaat tatattacta aacgaataat    6804
ttatttaggc cgattcattt gaatcaagga tttgttcagt aagttttgcc actgagtaaa    6864
ctgaatcgtg aatgacataa gatctatatt actgatatat aacattactc tgcatattga    6924
atttatggct gttgtatata tatattatgc ctacacagaa gtcaggtctg ctggtcacta    6984
aagtcagaat tataagcccc cctgaattat tagcaccct  gtttatttt tccccaatta    7044 ttgtttaaag gagagaagat ttttccaaca cattttaac acacaattgt tttaataact    7104
gggagaggca gtggcgcagt aggtagtgct gtcgcctcac aacaaaaagg tcgccgggtc    7164
actggttcga accttggctc agttggcgtt tctgtgtgga gtttgcatgt tctccctgcc    7224
ttcgcatggg tttcctccgg ctgctctggt ttcccccaca tactggctgg aagagtatcc    7284
gctgcgtaaa aacttgctgg ataagttggc ggttcattct gctgtggcga ccccagatta    7344
ataaatggac taagccaaca agaaaaggaa tgaatgagtt ttaatagctc atttctaata    7404
actgatttat tttctctttg ccatgatgac agtaaataat atttgactcg atatttttca    7464
agacacttct atacagctta aagtgacatt taaagactta agtaggttaa ttaggttaac    7524
taggcaggta ttaggcaagt tattgtataa cgatggtttg ttctgtagac tatcgaaaaa    7584
ttacatagct taaaggggct aataatattg accttaaaat tgtctttaaa aaatgaataa    7644 ctgctttat tctagccgaa ataaaacaaa tgataatttc tcctgaagaa aaaatattat    7704
cagacatact gtgaaaatgt ccttgctctg ttaaacatca tttgggaaat atttaaaaag    7764
gaaaagggag gctaataatt aactgtacaa atgaattcgc tccatggtgt gaaatgtgac    7824
agtttcacca tgtattatga gagctggtca gcaaataaaa acagatgaca tgctaagatg    7884
cctaagtatg atataaaata acattttaag gcaagcacag gttgccgaat tcatgcctag    7944
acgaaagtcc attaaatgag ataatgcaca aactgagaaa cagctgatga cggcatgggt    8004
tgatgtttgg tggacacaga actaattttta tagctgttta ttaatttcgg ctttatcaca    8064
```

```
tttttatctt gtgtgtgaaa actaaatgta acgaaaacaa aagtaaacat ttatttatgt    8124
tcgtttgttg ttgatgtttt accgttcgtt agtttttctg tatttagcga tcaaaaccga    8184
gaaaaccaat tatacgcatg tacatgaacc gtgaatctat tttgacgtac gaatgttggg    8244
atatttgtga taatacataa acaggacaga aatactgaag gagaaagtag attttagcag    8304
tgctctcgat gagatttaga gagcttttc aaaagccttc atactttgtc atgtggatct     8364
tgttgaggga ctttcctcaa catgcaatta ttttaatgct actctacaga tttctaaata    8424
aactcgtgct gccagccgtg tggtctctgg tcagacagat ttcccagaag gcttcagaaa    8484
aatacacgtt cagtcctaaa gtgacccaag accgtcggca tggttaaaca gtttattctg    8544
gagattttac ttgttgtaag ctttgtgttt aaatcattga gagttgagat tgaaatatga    8604
acaaagaaga aaaagtgaga agtccactga aacaaaagca agttctgtaa ctagaattga    8664
tagcttagat tatttttaaa tgctctgttt tatgttatta tatactgata ttatattcac    8724
tgtttggctt gagcttgaat ttaaagatgc agtatgtaag tttgacacct agtggtttaa    8784
ctaggtattg cactcctgaa tcaatacaca ttttcactcg gctccttctc tgatgagtcc    8844
acgctagagc aggttgccag attgaggttg agtgtgccag actatcgagc ctaaaggctg    8904
atttaaactg ttttctaaca aaaaaagaaa cggcacacaa tagtaggaat attttccatt    8964
ctaaaaggag tttttgacct aaccaacacc tggtgtttct attttagaaa cagcttctat    9024
ttctcacagg tgaacaacta tcacctcagg tacacctcat gtgctttatt cagagttaaa    9084
tgctaattat aggagtttga atgcaatttt acacaacatt tattgccata ctactgaaaa    9144
cagcagcaga tagttagatc tagaaaacta aataaaccat ttggaattaa actttagaac    9204
tgtgacattt cacaaccata tcataaccaa cacatacagt tgaagtcaga attattagcc    9264
cccttcgaat ttttttcttc gttttttaaat attgtccaaa tgatgtttaa cagagcaagg    9324
aaatgttcac agtatgtctg ataatatttt tccttctaga gaaagtctta tttagtttat    9384
ttcggctaga ataaaagtag ttttttgattt ttttaacacc attttaggga caaaatggtt    9444
agccccttta agctatattt ttctcgatag tctacagaac aaaccatcat tatacaataa    9504
cttgtctaat taccctaacc tgtctagtta acctaattaa cctagttaag cctttaaatg    9564
tcactttaag ctgtatagaa gtgtcttgaa aaatataaag taaatatttg tttacagtca    9624
tcgtggtaaa gataaaatta atccgttatt agaaatgagt tattaaaaat attatgttta    9684
gaaatgtgtt gaagaaatc tgctctccat taaacagaaa ttggggaaaa aataaataag    9744
aggtctaata attcaagggg gctaataatt ctgactttaa ctgtataaga tttagcatgt    9804
acttttaaaa atgtaaagag gtttaatatg tattaattag attataaacc ttatcatttc    9864
gttggagtgc agtgagtgca ctattctgtg cttctgaatg gctgtaaatt tctgttgtgt    9924
ttcgtctggt gtaaacagca ctgcaaatct catcgtgtag catgttttag gagacggggt    9984
tacaatgtaa actgctcgcc ttatgtttac catcgtaatg tatagattat ttgctaatta   10044
attaccacct catgtggaac tctgaatctg cttctcattt cggaggatgt ttttgtccac   10104
cagaggtctt attttggtca tgttcgaata cttttagagc cttcctctac tgaatgaaaa   10164
aaaaacaaca acgctgtttt ccattaaggc aacccaggtt gctgaaatat aataagctta   10224
actgccatta aactgccata tttctttcaa atgactattt tattacctaa aaactttctt   10284
atgtgtttcg ttgagcatca tctgttgttt ttggctccta tagtaaagta cggtaaaatc   10344
ctacagaagc aaacatatgc agtttgatgc agatgcttat atattttag ccaaagtgta    10404 atatgtcatt ctgatagctt cttacgaact tattaaaagt gtaactactt ggataaaata   10464
```

```
aatattaatc atccgtctgt atctccagta gcatttctta gtaggaggaa attagatgac    10524
taaacctctg taccttcaaa acataatgag agcacataaa ccgtcctcaa aagattagaa    10584
attttatcaa ggcttggggg agatcattta accgctgagg aactgtgaat gtaaaggttc    10644
tggaaataaa ccctcctcag aagcctttgc tttagtttaa caaatttcca tttgcattat    10704
ttaacattaa tacctttaa agggacagtt cacccaaaac tgaaaattct gtcttcattt     10764
actcacccta tatttgtcac aaaacttctt gtttaacaca aaagtcgata ttttgactta    10824
agttgaaaac cggtagctat tgactttcat agtatttgtt tttccgacta tcgaagttaa    10884
aggcaactgg cttccaacat tcttaaagaa atagtccacc caaaattgat aactcccaca    10944
agatttactc tcactcatgt agttttaaac atatattagt ttctcttttc tgttgaacac    11004
aaaagaggag atgttgaaaa atgctggttg gtgggatctt ccatagcagg aacaaaatga    11064
ctgggtacaa ccaaccagga ttcatcagaa tatcttctgt tgtgtttaac agacggatgt    11124
agctccaata ggttttttaaa gtaaagagag cgcaaatgat gacagagatt acattatctt   11184
cttttaggat caacagtagt taccttgaaa cctttaaggt gagcgaacag tgattttcaa    11244
atgtttgggt gaactatccc tttaatccat aggtctcaaa ctcaattcta ggacggccgc    11304
agttctgcct agttttgctc caaacctaat caaacatagt tgttccaaca aatcaaggcg    11364
ttcaagacta ctagagacta ttaaacaggt atgagttgga agtggttgaa gctaaacgat    11424
gcagagctgt ggccctccag gaattgagtt taagaccact gctttaaact ctaaagcaga    11484
ggtgaccaaa cttagtcctg gagggtcgat gtcctggaga gtttagctcc aaccctaatc    11544
aagcacacct gaacaagcta atcaagctct tgctagatat actagaacag gggtcacaaa    11604
tctcgttcct ggaggtccgg tgccttgcag ggtttagctc caacttgcct cagtgtttca    11664
agtataccta gtaagacctt gattagcttg ttcaggtgtg tttgatttgg gttggagcta    11724
aaatctgcag acaccggcc ctccaggaac aagtttggtg atcccaatac tagaagcttc     11784
ccggcaggtg tgttgaagca agtcggaact aaactctgca ggacactggc cctccaagat    11844
taagtttggg cacccctgct ctcaactatc aatgagacaa caggtttcta agatgtaaag    11904
aagcagtttc tgattttgac tggtgtgttt ttgtcctcct cta gag cac ctg gag     11959
                                              Glu His Leu Glu
                                                          120 gag ctg cag tca gac ggc tcc cag gag act cct ctg cga ttt gtt ttt      12007
Glu Leu Gln Ser Asp Gly Ser Gln Glu Thr Pro Leu Arg Phe Val Phe
             125                 130                 135 aat ctc agc agc atc cca gag gac gaa ctc ata tcc acc gca gag ctg      12055
Asn Leu Ser Ser Ile Pro Glu Asp Glu Leu Ile Ser Thr Ala Glu Leu
         140                 145                 150 cgc gtc tac agg caa caa ata gat gac gcc ttc tca gac cca gat caa      12103
Arg Val Tyr Arg Gln Gln Ile Asp Asp Ala Phe Ser Asp Pro Asp Gln
     155                 160                 165 aca ggg gac cat ggt ttg cat cgg ata aac ata tat gag gtg tta aag      12151
Thr Gly Asp His Gly Leu His Arg Ile Asn Ile Tyr Glu Val Leu Lys
 170                 175                 180 gcg cca cgg gaa gga cag ctc atc acg cag ctc ctg gac aca cgt ttg      12199
Ala Pro Arg Glu Gly Gln Leu Ile Thr Gln Leu Leu Asp Thr Arg Leu
185                 190                 195                 200 gtg agg cac aac acc tcc aaa tgg gaa agt ttc gac gtt agc cct gca      12247
Val Arg His Asn Thr Ser Lys Trp Glu Ser Phe Asp Val Ser Pro Ala
                 205                 210                 215 gtg ttg cgc tgg acc caa gaa aaa cgc tct aat cat ggc ctt gct gtg      12295
Val Leu Arg Trp Thr Gln Glu Lys Arg Ser Asn His Gly Leu Ala Val
             220                 225                 230
```

```
                                                        -continued
gag gtt gta caa atg aag cga aac cca gtt caa aag gga cga cat gtt    12343
Glu Val Val Gln Met Lys Arg Asn Pro Val Gln Lys Gly Arg His Val
            235                 240                 245 cgt gta agt cgc tcc gtg cat cct ctt ccg gat gaa gag tgg gac cag    12391
Arg Val Ser Arg Ser Val His Pro Leu Pro Asp Glu Glu Trp Asp Gln
    250                 255                 260 cta cgc ccc ctg ctg gtc aca ttc gga cat gac ggc aaa agt cac ccg    12439
Leu Arg Pro Leu Leu Val Thr Phe Gly His Asp Gly Lys Ser His Pro
265                 270                 275                 280 ctg act cgg cga gcg aaa cgc agc cct aaa caa aga ggt cga aag cgt    12487
Leu Thr Arg Arg Ala Lys Arg Ser Pro Lys Gln Arg Gly Arg Lys Arg
                285                 290                 295 aat cgt aac tgc cgg aga cat gcg ctg tat gtg gat ttc agt gac gta    12535
Asn Arg Asn Cys Arg Arg His Ala Leu Tyr Val Asp Phe Ser Asp Val
            300                 305                 310 ggc tgg aac gac tgg att gtg gca ccg cct gga tat cag gcg tat tac    12583
Gly Trp Asn Asp Trp Ile Val Ala Pro Pro Gly Tyr Gln Ala Tyr Tyr
        315                 320                 325 tgt cat gga gag tgt ccc ttt cca tta gcc gat cat ctc aac tcc acc    12631
Cys His Gly Glu Cys Pro Phe Pro Leu Ala Asp His Leu Asn Ser Thr
    330                 335                 340 aat cac gct atc gta cag aca ctg gtg aac tcg gtg aac acc aat atc    12679
Asn His Ala Ile Val Gln Thr Leu Val Asn Ser Val Asn Thr Asn Ile
345                 350                 355                 360 ccc aaa gcc tgc tgc gtg ccc act gag ctc agc gca atc tcc atg ctt    12727
Pro Lys Ala Cys Cys Val Pro Thr Glu Leu Ser Ala Ile Ser Met Leu
                365                 370                 375 tac ctg gac gaa acg gac agg gtg gtg ctg aaa aac tat cag gag atg    12775
Tyr Leu Asp Glu Thr Asp Arg Val Val Leu Lys Asn Tyr Gln Glu Met
            380                 385                 390 gtg gtc gag ggg tgt ggc tgc cgc taa acggagactc ttaccacaaa          12822
Val Val Glu Gly Cys Gly Cys Arg
        395                 400 aacatccaca cgtggacact tatttataac ttgtgtttgt catttcttgt ctgatcgatc  12882
atatattttg acagaaagta tatatatata aatatatatt tatatcggtg tagtaaaaaa  12942
taaataaaat gaaagtgtcc ttatttgaat tatataattc agctttccat aatgtatatc  13002
agactgtata aggttttttc tatatggagc cagatcagtc tcaaaaatta tacatttaca  13062
aaataaattt catacgctca caacaaaatt atcatttaca aaatccaatt cgtgaattca  13122
aaacacgatt cgtaaataca caaacacaat tagtaaattc aaaacaaaat taaaaaatgc  13182
tcaaattcaa ttcgttaatt gaaaacacaa tttgtaaata tacaaagcca attcgtaaat  13242
tcaaaacgct ttttgtaaat acacaaatcc aatttgtaa agtcaatacg atttgaaaat   13302
acacaaatcc aattcgtgaa ttcaaaacac tattcgtaaa tgcacaaatt caattctaaa  13362
ttcaaacgtg attcgtaaat                                              13382

<210> SEQ ID NO 5
<211> LENGTH: 116
<212> TYPE: PRT
<213> ORGANISM: Danio rerio

<400> SEQUENCE: 5

Met Ile Pro Gly Asn Arg Met Leu Met Val Ile Leu Leu Cys Gln Val
1               5                   10                  15

Leu Leu Gly Glu Ser Ser Tyr Ala Ser Leu Ile Pro Glu Glu Gly Lys
            20                  25                  30
```

```
Lys Lys Ala Ser Ala Leu His Leu Ala Gln Ser His Glu Leu Leu Arg
        35                  40                  45

Asp Phe Glu Ala Thr Leu Leu His Met Phe Gly Leu Gln Arg Arg Pro
 50                  55                  60

Arg Pro Ser His Ser Ala Val Val Pro Gln Tyr Leu Leu Asp Leu Tyr
 65                  70                  75                  80

Arg Leu Gln Ser Gly Glu Leu Glu Ala Gly Ala Gln His Val Ser
                 85                  90                  95

Phe Asp Tyr Pro Glu Arg Ser Thr Ser Arg Ala Asn Thr Val Arg Gly
             100                 105                 110

Phe His His Glu
         115

<210> SEQ ID NO 6
<211> LENGTH: 284
<212> TYPE: PRT
<213> ORGANISM: Danio rerio

<400> SEQUENCE: 6

Glu His Leu Glu Glu Leu Gln Ser Asp Gly Ser Gln Glu Thr Pro Leu
 1               5                  10                  15

Arg Phe Val Phe Asn Leu Ser Ser Ile Pro Glu Asp Glu Leu Ile Ser
             20                  25                  30

Thr Ala Glu Leu Arg Val Tyr Arg Gln Gln Ile Asp Asp Ala Phe Ser
         35                  40                  45

Asp Pro Asp Gln Thr Gly Asp His Gly Leu His Arg Ile Asn Ile Tyr
 50                  55                  60

Glu Val Leu Lys Ala Pro Arg Glu Gly Gln Leu Ile Thr Gln Leu Leu
 65                  70                  75                  80

Asp Thr Arg Leu Val Arg His Asn Thr Ser Lys Trp Glu Ser Phe Asp
                 85                  90                  95

Val Ser Pro Ala Val Leu Arg Trp Thr Gln Glu Lys Arg Ser Asn His
             100                 105                 110

Gly Leu Ala Val Glu Val Gln Met Lys Arg Asn Pro Val Gln Lys
         115                 120                 125

Gly Arg His Val Arg Val Ser Arg Ser Val His Pro Leu Pro Asp Glu
130                 135                 140

Glu Trp Asp Gln Leu Arg Pro Leu Leu Val Thr Phe Gly His Asp Gly
145                 150                 155                 160

Lys Ser His Pro Leu Thr Arg Arg Ala Lys Arg Ser Pro Lys Gln Arg
                 165                 170                 175

Gly Arg Lys Arg Asn Arg Asn Cys Arg Arg His Ala Leu Tyr Val Asp
             180                 185                 190

Phe Ser Asp Val Gly Trp Asn Asp Trp Ile Val Ala Pro Pro Gly Tyr
         195                 200                 205

Gln Ala Tyr Tyr Cys His Gly Glu Cys Pro Phe Pro Leu Ala Asp His
     210                 215                 220

Leu Asn Ser Thr Asn His Ala Ile Val Gln Thr Leu Val Asn Ser Val
225                 230                 235                 240

Asn Thr Asn Ile Pro Lys Ala Cys Cys Val Pro Thr Glu Leu Ser Ala
                 245                 250                 255

Ile Ser Met Leu Tyr Leu Asp Glu Thr Asp Arg Val Val Leu Lys Asn
             260                 265                 270

Tyr Gln Glu Met Val Val Glu Gly Cys Gly Cys Arg
         275                 280
```

<210> SEQ ID NO 7
<211> LENGTH: 3487
<212> TYPE: DNA
<213> ORGANISM: Danio rerio

<400> SEQUENCE: 7

| | | | | | |
|---|---|---|---|---|---|
| tgaccatcag | cattcgatta | ccaggaatca | tgatgtctct | ggtggacagg | ccgaaaacat | 60 |
| gggaaacaaa | aaagcaagga | tgactttgag | gcattagctt | caatacaaat | acaatgaaac | 120 |
| agtgtagaac | atatctgtag | atacaagcag | aggagacaga | tacaaatttt | aaaaacagag | 180 |
| agacagacct | tttggattta | tacattaaaa | gcaaccaggt | taccaggttt | aaacattgaa | 240 |
| ttaattttct | ttcctttttc | ttttcctatt | taaaaatttt | ctcctatttt | tttcattata | 300 |
| aataaaatata | tatatatata | tatatatata | tatttatata | tatatatata | tatttataat | 360 |
| gaaaaaaagg | tagggtacga | cctccacggt | tcaatacgcg | cttgtgaatt | gcggttttct | 420 |
| ctcctttgcg | tttaaataat | ttgtgtgtgc | ctgtaagtcc | atgagctgag | atgaggaaac | 480 |
| tcctccccgt | gagcaaatat | ccaattactg | tgctataagt | ttgggggggc | ttgaccatca | 540 |
| ttccacactt | taacatggcg | agtggcggtg | aagtgaggct | gaggcaacag | tacgaggaag | 600 |
| cgccggcgaa | gtgaggcaac | agtacgagaa | agcgccggcg | tctttcaaat | ctgcagtgtg | 660 |
| aggacatttc | gcttttgcag | gtaagcaaac | aagtgaaaag | cattcaaatg | aagattttaa | 720 |
| tcataatctg | tgtgagtttt | ttctcctttc | gtgactattc | aaacacattc | acccacattt | 780 |
| ttacctgcac | tactttagca | atctgatcag | gagttttttg | aggtgatttt | aagtcttaat | 840 |
| ttggccacaa | ctctcactgt | gtttcagcaa | attgtgtgat | ttttggagac | aaatcttatt | 900 |
| ttgacacata | ttttgtgaaa | atgctttaaa | attattcaaa | aacttaatac | actgtcagct | 960 |
| aatgtactac | tcttttgctg | tgttggggcc | gttttaccc | cattgacttc | cattaaaatg | 1020 |
| acatttttaa | aatgcaaagc | cttgacacca | tagtattgtg | tattcttagg | ctgtactcat | 1080 |
| actatgtaca | gttgctttaa | accgggccag | agcatgctcc | ccccccccat | gacgcttatt | 1140 |
| aaaaatcata | aagtcctcgt | gctgcaggaa | ttaggaggtc | tgctgaaggt | gcagctgtca | 1200 |
| tgcagtgagg | ggttttcgtc | tttaataaac | tacggcagtt | tgcgttcatt | gaatagtaag | 1260 |
| aatgattaat | aaatccatat | gaaacagccc | cttaagtcac | gactcgcttt | cagtttcagg | 1320 |
| ctttggcgcc | ctttgcactc | acacacaagc | gtaccgcacc | aaagcccaag | tgaaccgcgc | 1380 |
| tcaggcacac | ctcttccaac | tgggccaggg | ccggccgtgc | ctgagcccga | ttcagcgcag | 1440 |
| ggcggccatt | cagggcggcc | tgggcacagt | tcggatagca | tagtgcgagt | acgcccttaa | 1500 |
| ttgttgctgg | ttttccctgt | taagaaaatg | tgtaattttt | ttttgctttt | gatcattagt | 1560 |
| tgctggcttt | tatattgacc | ttattctaaa | atgcggaagt | gcgcctttt | cgcgattgtt | 1620 |
| ttagaacttc | agattcaatc | gcctatggga | gaaatgacta | ggaataataa | acggcagaaa | 1680 |
| acggtaaaac | tacttgcgct | acaaataaat | gtttacatga | ctatccagac | caagtttaat | 1740 |
| aaaataataa | gaaaatatca | gtttgcaaca | ttaaacagca | aaacaagcag | ttttttaacat | 1800 |
| ctaaaaatta | atggaagtga | atgagacagg | aaggctcaag | ccaaaaaaaa | aaaaaatcaa | 1860 |
| atggctgcgc | ttgctcgtca | tcagagaata | aggggaattg | agctatttgg | attatagtga | 1920 |
| gccattatat | agagacattt | aagcatgctc | agctcttaga | acataataaa | catagtaagt | 1980 |
| gtgtatatgc | acgcacacta | taatctgctg | ttttactcca | ctgaacatgt | aaaaaagaca | 2040 |
| gaaacttgtt | ttgcacaggc | ctatctaaag | ggttaaggct | gccaactgat | gatcaacagt | 2100 |
| aaaaattaca | acttttactt | tttccaaaca | gggaaaaatc | accaacaatc | aaaaaatgca | 2160 |

-continued

```
cgattttatg gctttgcaat caaaaaatct tattataatg gaagtcaatg ggccacgaac      2220
atggtgttaa actaatttaa aacagtctga aatgcatgtg atgctttaga acgcaacaac      2280
aaacaaaact gtggtagaat ctaccttacg tccatttttg tttagacaag caattgtaat      2340
gacaaagcaa gggacaagtt caattaaaca tgaaatttaa aacaccaaaa atagtcttag      2400
actttctttt agttacagct aaagaaaata tagtgtggac gtatttgcgt agtgttttt       2460 aacaacacat tgaaagagt gtgcgtgttt aaagaatcat tttccaaagt ataatagaaa       2520
tataatcgat tcactctcat gtcagtctaa aaattggaaa aggtctaaag ggttcaaatg      2580
acaacagatt aataaagggg actaagccga taagaaaatt aatgaatgaa tgaaaatagc      2640
gtacttatta atattaatga tcataatttc tgaattgaag cgtaattatg acaacaaaaa      2700
aaagtagttt tcacattatt tgtccatgtt ttagctattg taattgggtg tatgttttaa      2760
aataggatat gaaataaaaa ataaatacaa caattgtcat tttaagtcag cttttcattt      2820
aacctacaga ccaaacacaa acctaaagtt tcacagtcag acaagaaaac tctagacttt      2880
ttctgttttc catatcaatg ttttttgttga ataaatcatg cttttgtaac cccgtcagtt     2940
ccaagctggg attaaaccgg cgaccttccg catgggagtc ggttgctcta ccaagaaggc      3000
taaagaccat ggcctctagc attggtcgct agagcacctt tagaggtcag aggagtgagg     3060
tttacttgca gagcacacac tagctggcct ccgttacact cacccctcta aacctcactc      3120
ccatccgggt cacggcacca atgtaacccc tccggtctta cacaacccaa cccgctccga      3180
gctggtatca aaccggcgac cttccgcatg ggagtcgttt gctctaccaa ggaggctaaa      3240
gaccatggcc tctagcgttt gtcgcaagag cagctttaga ggtcagagga gtgaagttta      3300
cctgcacttt tccaatatat tatttttaat attgtgctgt ttgacaataa cagcagtctt      3360
cagttttcaa atgcaatgta aaagctggct tctgattggc ctgtttatta gtgaaaatca      3420
actacgcctt ttaattggct ccaaatattt actgctccat aatgcgactg gaacgggata      3480
ggagtgg                                                                3487
```

<210> SEQ ID NO 8
<211> LENGTH: 6111
<212> TYPE: DNA
<213> ORGANISM: Danio rerio
<220> FEATURE:
<221> NAME/KEY: misc_feature
<222> LOCATION: (2358)..(2382)
<223> OTHER INFORMATION: secondary structure unable to sequence; no
    sequence information available
<220> FEATURE:
<221> NAME/KEY: misc_feature
<222> LOCATION: (2392)..(2392)
<223> OTHER INFORMATION: ssequence information not sure;

<400> SEQUENCE: 8

```
gtgccttcaa aggttggact tttgtttatg tgaggcgaac tcctttgaga cccgttttac        60
cgtcttcata tccaagaaca ccgtgcgcat ctcttccaat ggtgagtcct attcaaaata       120
acagcattca tctggcgata ctttccatag agtcacagca agaagtgatc gaagacctat       180
atttatatag catatataga tacagtgact aaatggaagt catttacgcc ctttttattct      240 ctccggtgac ttaaaattgg ggcaaagtga gttttgcatt cgcacattca aacttttaacc      300 ttaatataat ttcagaaaca tatcatttcc aaataataaa cagggaaatc atattagcag       360
ccaaattatt atcaaagtaa acattgttca gttaaataaa tagtgttacg gttgcgttta      420
agtcttgtat atgattttag accgattaaa gtagcgtggt aagcattatg gagcttgtca      480
```

```
gacaagttac cactgttcaa aaatgaacga atgtgcgaat ataaaaccaa ctttacctca    540
aattacatga acgccccat tataatcatt aaacctacct tcacgtctga ttattaaaag     600
ctacatcaat tatatgagca ctcctgtttg taaacaaatg gtactgtgcg tgttaaaatg    660
actgatttta gtttgtttat agtgttttgg tagtttagaa gcagcggcgc gctcaaacac    720
ctgaccgcgc gcgcgcgcaa ccagccggct ggatgagcgc gtccacatct gcacacaaat    780
atagcagtgt ggcattgatt caaattaaat aagtgcgtgt tgtggtttct aaaaccacat    840
tagtggggtt tttattgttg tacgcatcct aaatcacgat ggtagaagta tagtattcat    900
atattacatt attttacgac acagcgttgc tcaaagggct gaacacactc ctggtcaaac    960
aacacataag taacgtaata cacaaaaaca actccctcaa caaacaatga gggagttttta  1020 gaatctacaa ccgaattcta aatgttctga aaccggattc attccaagta aactggcctt   1080
agtaaacaat tcacactgct agctcaagaa ggccatactg aaaaaacatt aataatatgc   1140
atatttgtat ctaaattcca gttaaaatat aaataaacat tacttgatag tcagtgatca   1200
ctatcagttt ataaaccaac atcctgttgt tataattttt agtcaaatat tgtcattctt   1260
agtccaagct agcattaaaa atagaggtta agttggcttt atattcacat tcgttcagtg   1320
acaactccct atattgttta ccacggcact ttaaatattc tgtctaaaat aacctgcaag   1380
tgtgacttga aaattaacgc tgtttatttt actgtgaaca gtgttgtact ttgatagtca   1440
ttggctgcta atatgatttc gctatttaga gtttgcaaat aatacttttg tgaaattata   1500
ttattaaagg ggaaagtcta aatgtgcgaa tataaaacca actttacctc aatgcattaa   1560
aaaagggttt tagtcagaaa ctgaaccagt gcatttgacc tcgctcatgt tttgaatgtc   1620
tatgagtcgt aattagtctt aaatgagttg tagtgaagag tgatggccct cagtcaagcg   1680
taagaacacg actgaaaatc ttttacgagg tacattatgg cataaggggg acacaacctc   1740
acgagccatt tggcagggat atttagattc agctcaaaga ggtggaaagc aaaaagtgaa   1800
gaaataagat actgtcgaaa tagcatgtca tgccaaatac ttcttcgaaa ataaacactg   1860
ttgcaagagc tgaagccggt ccactggtgg ttacaagtcg acacatgctg ttgtctaaag   1920 cagggggtctt gatgcamaag taaaggctgt cggtggatat caataccaac aaaattcatg  1980
ttaattggtt aaaacaagga caaatagctg tttaaggtta cattttgaca gcacactgcc   2040
ttttcttatc acagtttatt atggaaagga caaaaacaca atcagatgga aactttactt   2100 gtgttttttac ttagtaattt ctttgaatgc aatacttttg tttatcgttt tgcaatggag  2160
actggmgaac aaccagtaat aaacaacaca tttggtggat taaagggat agttcactcg    2220 aaaatgtaaa tttactcact attttctcac cccctgctga aaaaaaacag cttaaaccag   2280
cctaggctgg ttggctggtt ttagctgkys rmcmrgsykg ktttwrrrgg gttttggscm   2340
attycmrgsy kgkttccnnn nnnnnnnnnn nnnnnnnnnn nnaacccaac cnccctaggc   2400
tggtttaagc tggatttttt agcagggcct caagtggttc cagacttgaa tgagcttct    2460 tcttctgaaa agaagatatt tagaggaaag ctgaaagccc atagtcattg aattccatag   2520
taggaaaaac aaataccttg gatatcgatg attaaagggt ttccaacatt tttaaaagca   2580
tcttcatttg tcttcaacag tggaaagaaa ctctcaaagt aaagagtgag taaatgatga   2640
cacaaatgat tatttttttg agtgaactgc cccttgaata taacagctca atcaattagt   2700
cacacttcag catctcattt tccaatcgaa cacaatgctg cttgtgtgtc tccagatttg   2760
atttgtgaat aaaacccgac agaggttaaa tcctaacatt ggcagccctg cactgtctgt   2820
tcctctgcta acttacaccc ccatatacccc tgtccacaca catctgaagg accatgtgca   2880
```

```
taacctcatc tcattaacgg ggctaaggta gagcaaagtt gaacgctgtg agatttacat    2940
gactgcgcca aattaaagga ccataaaacc cagcctctgc taaaaagcac atgcgttgct    3000
ctgagtcttc aaacagggat tctgtaaata tttagggcag tatctgtagg cttttaaaca    3060
agagtaggtg gtctgaagaa ccaattgttt gtgctttgct gcatggtttc tggcatggcc    3120
gatcaaagtc ttttgagtta cgctcatttt tatggtttgc tctcgactta atgagctgtt    3180
tgcgttgttg ttaaactgca gacgttagga atctaaaagc ccccggcctc cggttaaaca    3240
ccaatttctg gtggtatata atacacataa gtacaactag catgagaaat gatgctttat    3300
tttgaagaca gactgtgaaa ctttaggttt gtgaaacttt rggtttgtgt ttggtctgaa    3360
ggttaaaatg aaagctgact taaaatgaca atagttgtat ttattttttt atttcatatc    3420
ctattttaaa acatacaccc aattaaaata gctaaaacat agacaaataa tgtgaaaact    3480
acttattttt ttgtcataat tacgtttata ttcagaaatt atgatcatta atattaataa    3540
gtacgctatt tttattcatt cattttctta tcggcttagt cccttttatta atctgtatta    3600 ataaatctgt attagtctgt taatgagctg tttgcgttgt tgttaaattg cagacgttag    3660
gaatctaaaa accaccggcc ttcggttaaa caccgatttt tggtggtata taatacatat    3720
aagtacaact agcatgagaa atgacgcttt attttaaaag acagaatggg atagaggaga    3780
gatagagggg ataaataaca ctcatgacca cacacacaca cgcacacaca cggtgttctt    3840
gttaaaatgc atcattcctg ttgtaatgct tggacttgct ccagaagaac cagagtccaa    3900
gaaatgacaa agtgcatgcg ttgctatgct cagctattga gttcagctgt ggattcaacg    3960
atgacgttgt tttctgagat tgagcacttg tgattgttat taggccacac aaattattca    4020
gtttgttaaa attattcaat tgaggatgtc tctcctgatt ttggcacaaa tgttacgggt    4080
cgacaaaagc gagacggtgc cgcttgtatg cacgaattag ggttttaaag actgtttaaa    4140
gaggggacca tcaataaaat aggcagctcc tttgtggacc aacgaacctc tatttgtatg    4200
taaattgtaa tggttgtcct tgaggtgtt gacacctggt agtctgctaa agataatggg    4260
tgcatcccaa atcgcatact tgtgcactac tctatgccac tttgtagtat aaatagtaca    4320
cttcctgaca aaagtcctgt cgcctatcta agtaggaaca acgaataata agttgacttc    4380
tagttgatta tttggtatca gaagtggcgt atatgaaagg taaaggcctc tagatgacgc    4440
ttatttgagc acaataaaat atgatcatac cttgattatt aatgatttga ttaggacagt    4500
aagatctgac tctgctcaga ctaaagtctc atcactgaac agaaataatg tccagtatag    4560
aataaaaagt cctgctgcag tggagacaga atgaatattg tgtctgactt catcatgagc    4620
ttggaggact gcatccatac atctctgaca tgactcaaat cactgattaa taaagtcatc    4680
tggaatggca agaaagcgt tcagcaggac tcccagagct catcaagact cttttgtgtta    4740 atcttcaacg cctcctcctt catctttgcc cagacatgct caataatgct catgtctggt    4800
gactgggctg gccaatcctt ctttgctttc aggggatttg atgtggaggc tgaagtatga    4860
gaaggagcgc tatcctgctg gagaattggt cctctcctgt ggtttgtaat gtaatgggca    4920
acacaacagg ctgttgatgt ttttgatgac actttaattg acattctccc tttgtatgtg    4980
tcatcgaagg gggaaagccc cgcccatttg tgccaatctc tccattatta gcagaaacag    5040
ccctgagtaa gaagcagctg tccactatta gagtttcgat tctgctattt tcgtgacacg    5100
ttagtgtttg tggctccacc ctctttgaa aagcatctca tttgaattta agtcattaa    5160 aatgccacaa tttgcatcaa aacttaaaag gctcagtttc aaaggtgtat taaacaatat    5220
ttataaggta ttttgcgctg aaacttcaca cacacactct agggacatca aagacttatt    5280
```

-continued

```
ttgcatgttg taaaaagggg tgtaataggt ccccttttaag ttgaacactt catgtactat      5340
tgctgaggat ggattactta aattattta gattgtgcaa gcaaaaattc tcctacacaa       5400
gtgattatgt gactcataag tacaatagtg tttttttca ctaatttggc aaccgttaaa       5460
cattgcctgg gaaatggctg gcatttctgt ttttctgtga tctatttggg atgatattaa      5520
gtgaagtttc ataaactaat tttgagagga gcacgtgatg tgattaagca ctactggctg      5580
ctcatctgta atcagtaata ayccaatcag cgggacccat agtttactrt aaatggatca      5640
tttttatcct gctgctctat cttcgttttg gaagaatccc cccttccacc ccatctcctc      5700
cttttcctcc ctttctaaag ggagagttct cgagacctaa ctgatctcgg atctcctgat      5760
atgcttattg accaagcggg aaccctgggc tcaaatatct ccgagctcag ggttctctcc      5820
cgggacagca tgccaaacct gctataaatg ctaagcatat ctaagtggga actcttgaaa      5880
ctctacatgg tttagtgtat attgtgtcat tcgggatgta actaatgtgt tgcgcaagca      5940 gcatttagt cgctatttt actcctgttt tgccaacatg aaacagtttt actactatgt       6000
ttgctgtaat gagatgttaa gctgcaaata taccgttgtc tttcaggaaa aggatctccc      6060
cgcgattctc aaacagcctg ccaggaccac gtaacattcg cttgaggagc t               6111

<210> SEQ ID NO 9
<211> LENGTH: 19528
<212> TYPE: DNA
<213> ORGANISM: Danio rerio

<400> SEQUENCE: 9
ggcgcgcctg cggacctcga agagtattgc ttcattcatt gccacggcga gttgaaaggt        60
gcactccatc ccggttttgca attttcactc gggcagcatc gctatccggt gaccgctgtt      120
ggcagcgtgg cggaagacaa ccttcgcgaa ctgggtcatg tcaccctgcg cttcgatggt       180
ttaaacgaag cggaatttcc gggcactgtc catgtggcag gccctgtccc cgacgatatc       240
gcgccgggat cggttttgaa gtttgaatct gttaaggagt aaaaaatgaa tcaggttgcc       300
gttgtcatcg gtggtgggca aaccttaggc gcgttcctgt gccacggtct ggctgccgag       360
gggtatcgcg tcgcggttgt cgatattcag agcgacaaag ccgcaaatgt ggcacaagaa       420
attaacgccg aatatggtga agtatggcg tacggttttg gtgctgacgc cactagcgag       480
caaagcgttc tggcgctctc tcgtggggta gatgaaatct ttggtcgcgt ggatttgctg       540
gtctacagcg ccggaatagc aaaagcagcc tttatcagcg acttccagct cggcgatttt       600
gaccgttcgc tacaggtgaa tctggtgggt tatttcctgt gtgcgcgtga attttcgcgt       660
ttgatgatcc gcgacgggat tcaggggcgc attattcaga tcaactcgaa atccggcaaa       720
gtgggcagca acacaactc tggctacagc gcagcgaaat ttggtggcgt cgggctgact       780
caatcactgg cgctggatct ggcggagtac ggcattacgg tgcattcact gatgctcggt       840
aacctgctga aatcgccgat gttccagtca ctgttgccac aatacgcgac caagctgggg       900
actgagagat cccctcataa tttccccaaa gcgtaaccat gtgtgaataa attttgagct       960
agtagggttg cagccacgag taagtcttcc cttgttattg tgtagccaga atgccgcaaa      1020
acttccatgc ctaagcgaac tgttgagagt acgtttcgat ttctgactgt gttagcctgg      1080
aagtgcttgt cccaaccttg tttctgagca tgaacgcccg caagccaaca tgttagttga      1140
agcatcaggg cgattagcag catgatatca aaacgctctg agctgctcgt tcggctatgg      1200
cgtaggccta gtccgtaggc aggacttttc aagtctcgga aggtttcttc aatctgcatt      1260
cgcttcgaat agatattaac aagttgtttg ggtgttcgaa tttcaacagg taagttagtt      1320
```

```
gctagaatcc atggctcctt tgccgacgct gagtagattt taggtgacgg gtggtgacaa    1380
tgagtccgtg tcgagcgctg attttttcgg cctttagagc gagatttata caatagaatt    1440
tggcatgaga ttggattgct tttagtcagc ctcttatagc ctaaagtctt tgagtgacta    1500
gatgacatat catgtaagtt gctgataggt ttccagtttt ccgctcctag gtctgcatat    1560
tgtactttc  ctcttactcg acttaaccag taccaaccca gcttctcaac ggatttatac    1620
catggcactt taaagccagc atcactgaca atgagcggtg tggtgttact cggtagaatg    1680
ctcgcaaggt cggctagaaa ttggtcatga gctttctttg aacattgctc tgaaagcggg    1740
aacgctttct cataaagagt aacagaacga ccgtgtagtg cgactgaagc tcgcaatacc    1800
ataagtcgtt tttgctcacg aatatcagac cagtcaacaa gtacaatggg catcgtattg    1860
cccgaacaga taaagctagc atgccaacgg tatacagcga gtcgctcttt gtggaggtga    1920
cgattaccta acaatcggtc gattcgtttg atgttatgtt ttgttctcgc tttggttggc    1980
aggttacggc caagttcggt aagagtgaga gttttacagt caagtaatgc gtggcaagcc    2040
aacgttaagc tgttgagtcg ttttaagtgt aattcggggc agaattggta aagagagtcg    2100
tgtaaaatat cgagttcgca catcttgttg tctgattatt gattttttcgc gaaaccattt    2160
gatcatatga caagatgtgt atccaccta  acttaatgat ttttaccaaa atcattaggg    2220
gattcatcag agctgggtat caaaccggat caagtcgagc agtattacat cgacaaagta    2280
ccgctcaaac gcggctgcga ttatcaagat gtgctgaata tgctgctgtt ctacgccagt    2340
cctaaggcgt cgtactgcac cggacagtcg atcaatgtca ccggcggtca ggtgatgttc    2400
tgatcaacag cggagatcca ttaaggatct ccgtgagact atagaatgcc tgatgcgcta    2460
cgctcatcag gcatacagga cttccgccac tacattaagg aaaagttatg gtatccgcac    2520
tcatcaccgt cgccgttatc gcctggtgtg cgcaactggc cttaggcggc tggcaaattt    2580
ctcgttttaa ccgtgccttc gacacactat gccagcaagg gcgggttggc gtgggccgtt    2640
ccagcgggcg ctttaaaccg cgggtcgtgg tcgccatcgc gctggacgat cagcagcgca    2700
tcgtcgacac cttgtttatg aaaggactga ccgtcttcgc ccgaccgcaa aaaattcccg    2760
caattaccgg tatgcatgcg ggtgatttac agcccgatgt gatctttccc catgatccac    2820
tatcacagaa tgctctatca ttggcgctta aactgaaacg tggataattt cgttgtgaat    2880
gttacttgct tgcgaagtta tcattttgaa acctaaatca ggtaatcacg cccatgaaac    2940
ctcgtcagcg tcaggccgcc attctggagt atctgcaaaa gcagggtaaa tgctcggttg    3000
aagaattggc gcaatacttt gacaccacag gcacaaccat tcgcaaagat ctggtcattc    3060
tggaacatgc cggaaccgtc attcgtactt atggcggagt ggtgttgaat aaagaggaat    3120
ccgatccgcc tatcgatcat aaaaacactt catcaacacc cacaagaaag agctgattgc    3180
agaagctgcc gttagtttta tccatgatgg cgattcgatc attcttgatg ctggcagtac    3240
cgttttgcag atggttcccc tgctctcgcg ctttaataac atcacggtga tgaccaacag    3300
cctgcatatc gtcaatgcgc tatccgaact ggataacgaa caaactatcc tgatgccagg    3360
cggaacgttt cgcaaaaaat cggcctcatt tcacgggcaa ctgcagagga atgccttcga    3420
gcatttcacc ttcgataaat tgtttatggg caccgacggc atcgatctca atgcgggcgt    3480
aaccaccttt aacgaggttt ataccgtcag taaggcaatg tgcaatgccg cgcgcgaagc    3540
tgattttgat ggcggactca tcaaagtttg gccgtaaaag ccccaacgta gtttgcagtc    3600
ttgaaagcgt cgataagctg attaccgacg caggtatcga tccggcgttt cgtcaggcgc    3660
tggaagagaa agggatcgat gtgatcataa ccggagagag caatgagtga agcactactg    3720
```

```
aacgcgggac gtcagacgtt aatgctggag ttgcaggaag caagccgttt accggaacgt   3780
ctgggcgatg attttgttcg cgccgccaat atcatcctgc actgtgaagg caaagtggtg   3840
gtttcgggaa ttggcaaatc gggccacatt ggtaagaaaa tcgccgcaac gcttgccagt   3900
accggcactc cggcttttt tgtccatccg gcagaagcgc tgcacggcga tctggggatg   3960
atcgaaagcc gcgatgtgat gctgtttatc tcttactccg gtggcgcgaa ggaactggat   4020
ctgattattc cgcgtctgga agataaatct atcgcgctgc tggcgatgac cggcaaaccg   4080
acgtcaccgc tgggcctggc ggcaaaagcg gtgctggata tctccgtaga acgcgaagcc   4140
tgcccgatgc accttgcgcc gacctccagc accgtcaata ccctgatgat gggtgacgcg   4200
ctggcgatgg cggtcatgca ggcgcgcgga tttaatgaag aagattttgc ccgctcccac   4260
ccagccgggg cactgggcgc tcgcttgctg aataaagtgc atcatctgat gcgccgtgac   4320
gatgccatcc cacaggtggc gttaaccgcc agcgtgatgg atgcgatgct ggaactcagc   4380
cgcaccggtc tggggctggt ggcggtatgt gacgctcaac aacaggtaca aggcgtcttt   4440
accgacggcg atttacgtcg ctggctggtt ggcggcggcg cactcaccac gccagtcaat   4500
gaagcgatga cggtcggcgg caccacgttg caatcgcaaa gtcgcgccat cgacgccaaa   4560
gagatcctga tgaagcgcaa aatcactgcc gcaccggtgg tggatgaaaa cggcaaactc   4620
accggcgcaa taaacctgca ggatttctat caggcccgga ttatttaatc cttcaatccc   4680
agacgtttcg ccagccgatg caggttggcg acgtcggttt ccagcatccg cgcgcaggca   4740
gcccagttgt gatgattttg tgccagtgcc tgacgaatag tttcacgctg gaacgcttct   4800
gtcgcttcac gcaggttttg cttaacaacg ggcaccgccg ccacttctgg cgtcggcaac   4860
gtcacctcag gaaaagcaaa atgttgcgcc tcaagaatca cttcatcgcc gctgcgggtg   4920
gctctcgcca gaactaccgc ccgatgaata gcatgttcca gttcgcgcac gtttcccgga   4980
aaactgtagt gttgcagtaa atttcgcgct ccggcactta ataccacgcg ggagagcccc   5040
tgccgcaaac gacactgctc gcagaaatac cccgccagca gaatgacatc atcgccccgc   5100
tcacgcagcg gcggcaccga aagtggaaac acgctcaggc gatgaaacaa atcggcgcgg   5160
aatcgccctg ccagcacctc ttcgcgtaaa tcgcggttag tcgccgccag cacgcgcaca   5220
tcgacccgca acaacggtc atcgccaacg cgctgaatat cgccatactg caacaccctc   5280
agcagcttgg cctgcaatgc caacgacaac tcgccgatct catccagaaa cagcgtgccg   5340
ttatccgcca tttcaaactt cccgctgcga ttactgatag cgccagtaaa cgctcctttc   5400
acatgcccga acaactcact ttccgccaca ctttccggca gtgcagcaca gttgagatag   5460
accagcggat tcaccgcccg tggcgaggct tcatgaatcg ctttcgccac cagctcctta   5520
ccggttccag tctcaccgct gatcaggacg ttgagatcgg acgccgccac aatctcaatc   5580
tcttttttca gttgcgtcat gccaggggac aagccaatca tctgcgtctg tttcaccgct   5640
tcaaacggcg tggcatcgcc tggcagcata ttctggcttt ccagttgttc aatcagcaac   5700
gcattgctta acgctcccgc cgccagcgca gcaatcagcc gtagctcttc gtcgctgaaa   5760
acatcgaact gatcgggctg catcccgtcg agcgtcagtg cgccgatcag gttttgcccg   5820
gcaaacaatg gcagaccaac gcaggcgtga accttcagac tctcctgccc aggaatcaaa   5880
ccgtcatagg gatcgggcaa ttcgctgtct gcgggaaagc gcaccacatc cccggcgcgg   5940
gcaatcgctt ccagccgtgg atgcccttcc agcgcaaagc gtctaccgag tacatccttt   6000
gccagaccgt cgatggcaag cggaataaac tgccgcgaat cgtaacgtag caacgcagac   6060
gcatcgcact ccagcacctg acgtagcgtg gtgatcaggc gctgaaaacg atcctggtga   6120
```

```
ccaatcccac gctgcaattc gatggcgata ttcgccagca catcaacgga aaaactcatc    6180
tttgcctcac tgtcaatttg actatagata ttgtcatatc gaccatttga ttgatagtca    6240
ttttgactac tcattaatgg gcataatttt atttatagag taaaaacaat cagataaaaa    6300
actggcacgc aatctgcaat tagcaagaca tcttttttaga acacgctgaa taaattgagg   6360
ttgctatgtc tattgtggtg aaaaataaca ttcattgggt tggtcaacgt gactgggaag    6420
tgcgtgattt tcacggcacg aatataaaa cgctgcgcgg cagcagctac aatagctacc     6480
tcatccgcga agaaaaaaac gtgctgatcg acaccgtcga ccataaattc agccgcgaat    6540
ttgtgcagaa cctgcgtaat gaaatcgatc tggcggatat cgattacatc gtgattaacc    6600
atgcagaaga ggaccacgct ggggcgctga ccgaactgat ggcacaaatt cccgatacgc    6660
cgatctactg tacagccaac gctatcgact cgataaatgg tcatcaccat catccggagt    6720
ggaattttaa tgtggtgaaa actggcgaca cgctggatat cggcaacggc aaacagctca    6780
tttttgtcga aacaccaatg ctgcactggc cggacagcat gatgacttac ctgacaggcg    6840
acgcggtgct gttcagtaac gatgcttttcg gtcaacacta ctgcgacgag catctgttca    6900
acgatgaagt ggatcagacg gagcttttcg agcagtgcca gcgttactac gccaatatcc    6960
tgacgccgtt cagccgcctg gtaacaccga aaattaccga gatcctgggc tttaacttac    7020
cagtcgatat gatagccact tcccacggcg tggtatggcg cgataacccg acgcaaattg    7080
tcgagctgta cctgaaatgg gcggctgatt atcaggaaga cagaatcacc attttctacg    7140
acaccatgtc gaataacacc cgcatgatgg ctgacgctat cgcccagggg attgcggaaa    7200
ccgacccacg cgtggcggtg aaaatttta acgtcgcccg aagcgataaa aacgaaatcc      7260
tgactaatgt cttccgctca aaaggcgtgc tggtcggcac ttcgacgatg aataacgtga    7320
tgatgccgaa aatcgccggg ctggtggagg agatgactgg tttacgcttc cgtaacaaac    7380
gcgccagtgc tttcggctct cacggctgga gcggcggtgc ggtggatcgt ctttccacgc    7440
gcctgcagga tgcgggtttc gaaatgtcgc ttagcctgaa agcgaaatgg cgaccagacc    7500
aggacgctct gaagttatgc cgtgaacacg gtcgcgaaat cgcccgtcag tgggcgctcg    7560
cgccgctgcc gcagagcacg gtgaatacgg tagttaaaga agaaacctct gccaccacga    7620
cggctgacct cggcccacgg atgcagtgca gcgtctgcca gtggatttac gatccggcaa    7680
aaggcgagcc aatgcaggac gttgcgccag gaacgccgtg gagtgaagtc ccggataact    7740
tcctctgccc ggaatgctcc ctcggcaaag acgtctttga agaactggca tcggaggcaa    7800
aatgagtaac ggcattgtga tcatcggttc gggcttcgcc gcccgccaac tggtgaaaaa    7860
tattcgcaaa caggacgcca ctattccatt aaccctgatt gccgcgacga gcatggatga    7920
gtacaacaaa cctgacctca gccatgttat cagtcagggg caacgtgccg atgaccttac    7980
ccgccagacg gcgggtgaat tgccgagca gtttaatctg cacctgtttc cacaaacctg     8040
ggtgacggat atcgatgccg aagcccgtgt ggtgaaaagc cagaataatc agtggcaata    8100
cgacaagcta gtactggcaa ccggtgccag tgcctttgtc ccgcctgtgc ctgggcgtga    8160
gttaatgcta acgttaaata gtcagcaaga gtatcgcgcc tgtgaaacgc aactgcggga    8220
tgcccgacgc gtgttgattg ttggcggtgg tttgattggt agcgaactgg cgatggattt    8280
ttgtcgtgca ggcaaagcgg tcacgctaat cgacaacgct gccagtattc tggcgtcgtt    8340
aatgccaccg gaagtaagca gccgcttgca gcatcggttg acggagatgg gcgttcatct    8400
gctgttgaaa tctcagttac aggggctgga aaaacggat tctggcattc aggcaacgct     8460
ggaccgccag cgcaatatcg aagtggatgc ggtaattgcc gccaccggac tgcgcccgga    8520
```

```
aaccgccctg gcacgacgcg ccgggctgac gattaatcgc ggcgtttgcg tcgatagtta   8580
tctgcaaacc agtaataccg atatttacgc gctgggcgat tgcgcggaaa ttaacggtca   8640
ggtattgccg ttcctccagc cgattcaact tagcgcgatg gtgctggcaa aaaatcttct   8700
cggcaataac acgccgctga aactcccggc gatgctggtg aaaatcaaaa cgccggaatt   8760
accgctgcat ctggcaggcg aaacccagcg tcaggattta cgctggcaaa ttaataccga   8820
acgccaggga atggtggcgc gcggcgttga cgatgctgac cagcttcgcg cctttgtggt   8880
cagtgaggat cggatgaaag aggcatttgg attgktgaaa acattgccga tgtaggtggg   8940
ctactgtgcc taaaatgtcg gatgcgacgc tggcgcgtct tatccgacct acggggacgc   9000
atgtgtaggc cggataaggc gtttacgccg catccggcaa tggtgtccaa atgcaacacg   9060
ttttatccgt tctggacttc acccgctaac caacgcgccg cagcaataac cccctgcccc   9120
agagacaaac cgccatcacc cgccggtaaa ctctgtggaa agagcaatgt gaaatcagcg   9180
agataatgcg ccagacgtgc acgcagcaaa cggttatgaa taaccccgcc gctaaatacc   9240
agcgtagtga taccacgcat cgtggcctgc tcacgcatca acgcggcaaa accctgcgcc   9300
agcgcatcat gaaacgccca cgcgcgttga ttaaccggtg cctgccagtt cagccactgc   9360
tgccagaaag tggcgagatc cagttgattg tccacccgcg gcattgtcac cggatgcgtc   9420
actccgtggc atgaggctgc gagcgcctcc agagcacaag ccgcttcacc ttcataactt   9480
aacgtggctg gcgcacagcc cagtgccgcc gccactgcat cgaaaaaacg cccacacgat   9540
gacgccagcg gcgcgttaat tccacgctca atggcccgcg ccagcacgct ccagttttgc   9600
tgttgcacac ttgctgtttc agagtaattc tgccactccg gcacaaagcg caggcactgc   9660
gccagcaggt ttcgccacgg ctgcttcgct gccaaatcgc cacccggaag cgccactgca   9720
ggcaagccgc ccaggtgctc acattcgcga tagttcaccc gcaggcactc gccgccccac   9780
aaagcgccgt tctcccccat accgataccg tcgagcgtca aagcaatgac atcaccgcca   9840
tccagcggcc actgatgctc tgccagacac gccgctgcat gggcatgatg atgcagtacc   9900
gtttgcgtcg gcagattcat ttcacgcgcc cactggctgg agacatagcc cggatgcgcg   9960
tcatgcacaa cgtattgcgg ggtaaaatcg tagatgtttt gcatcaggcg taacgcttcg  10020
cgccactgca tctggatgcc atcgtcactt aaatcgccca gatgctgact caacaccgct  10080
tgttcaccgc gcaccaggca gaaggtattt ttcagatccg cgccgagaca cagcacaggc  10140
ggaacatttt taaagcccgg aggcaaagcc agcgcatccg gcacataccc ccgcgaacgg  10200
cgcagcattt cgccgctttc gcgcaccacc gaatcatcca tccgctgcac gatgtcgcgg  10260
ttatgtatca agaatccgtc ggcaatgccc tgcaaatccg ccagcgcctg ttcgttgctg  10320
atagctggtg gtttaccgct caggttgccg gaggtcatca ccagcgggca ttgcagttcc  10380
tgtaacagca aatgctggag cgggttcgca ggcaacatta ccccgacttc gttaaggtca  10440
ggggcgatat catcacaaag ctcaggaacg tatttttttat ccaccagcac aatcggcgcg  10500
gcgggcgtgg taagcaactg gcgcgcagcg tctggtaaac cgtcagccac tggcaacatg  10560
accgccagcg gtttcgccgg gcgatgtttg cgcgcccgaa gtgtcgccac cgcgttactg  10620
ttacgtgcat cgcaggcaag atgaaatccg ccaatccctt tgatggcgac aattttgccc  10680 attttttaact gtgcgatagc tgcctgtaat gccgcctctt gttccgcatg ttcaccatga  10740
cttacccatt caagatgcgg gccacactcc gggcaggcca ccggctgggc gtggaagcga  10800
cgatcgagcg ggtcacggta ctctttgtca caggccggac atagcggaaa cgccgccatc  10860
acggtaaacg ggcggtcgta aggcatggcg cgaataatgg tgaaacgcgg gccgcagtgg  10920
```

```
gtacagttga taaacggata acgataacgc cgttcgcctg gggtattcat ttcggcaagg   10980
caagcagggc aagtagcggc atcgggaaca atttgcgtat tcatggtgcc gcctgtgctc   11040
tggcgtatag tgaactcggt gggcagttgt gaccagataa acggctcacg ctcgacgcta   11100
tcaatacgcg ccagcggcgg gcagtgctga tacaattgaa caagaaacgt ttccgggtct   11160
tcccgcagcc ggacttctac gccatcgccg tcattacaga catcgccgtg aagatttaat   11220
tgctgtgcca gctgccagac aaacggacga aaaccgacgc cctgcacttt gccacgaata   11280
cgcagttgga caccgcaaga tgtgtttttt gccattgagt tattcccgcc atcatgaatt   11340
gcgtaacccg ccctgccgga cacgacagcg tcgcatccgg cagtcacagg tcggcgatac   11400
cgcccgctcc gtattctacg aatatttccg ggaattcctt tgatgccaga acagttctgt   11460
aagattttta gaacatcagc gccgtacggc ggcgttttc tgcgctcagt tgttcaagtt   11520
tattacgatc gacacaaatc agcgcatgag tcgggcaagc cgccatacac gccgggccgt   11580
cttcacgatg gttgcacagg tcgcatttat tggcttcggc tttgtcagcc cgtacattca   11640
gacccgcgcc gctgttgcgg atcaccggac gtaccaccac ttccatcgca ccatacgggc   11700
aagccacaac gcaggttttg caaccaatgc aacgttcctg catcacatga acaaacccctt   11760 tatcacggct gatagcacca ttcgggcaga cgttagcgca cggtgcatct tcacactgac   11820
ggcaaactgt cgccgtggaa atgttcacac ctttaatgac atggatacgc ggtaaaaaag   11880
tttccggggt cagcgatgca cagtcctgat tttcctgatg agaaaccacg cacgctactt   11940
cacaggtacg gcaaccaata catttactcg cgtcagcaat gatgaaacgg ttcatcaaat   12000
tctccagcaa tgacagttaa tgcgccgata cattcacaaa tcatgccagt ttttaattta   12060
ctgttattta aggaaattaa tttctgtaat gcaggaaaaa cgatgtcatc gacactagtg   12120
acgatgacat gtgatgacaa tgtttatcgc gaaggagcaa tgagtgagtc gcggcggatc   12180
agttttccgc tgaaggtttt cggcggtgag aaatccccgc catcgagcat aaaaatcagc   12240
cgtccaataa tttcctgaat catctcagtc accggaattt ttacgctgga gagcgccgga   12300
acggtgtagg gggcaatagc gatatcatcg aatccgataa ctgacacctg ctctggcacc   12360
gctacgccgc gctcgtgtaa cgctttcatc gcacctatcg ccatatcgtc gttactggca   12420
actaacgcgc taaatttagc cccacgttcg agcaacattt ctacccccttc ggccccgctg   12480 gcaggcgtcc atttaccgtt agcgataagt ttttcattga gcgcaatacc atgctgcgcc   12540
agcgcgtctt tatacccggc aagacgttca atgctggtgg gggaatccat cgagccggta   12600
aggaaagcaa tctcctgatg cccggcgttt atcaactctg ccacggcgtt aaaactggtc   12660
tgtttatgat cgcaccagac gctatggctg ctgttttttgc gcaggcggcg attaagcacc   12720
attatcggct gactgtgcgc gtcaatgatg tcatcgatct catccacgct taaaaaacgc   12780
gggtaaatca tgatcgcgtc gcagcgcaga tccagcagat actgaatcgc ctggcgctct   12840
tcttctgcgc tgtgttacc atctgccaat agcaactgcc gcccttttctc ttccgccatt   12900 cgcgcggcat gaaagagtaa ttcactaaaa taaatgccgt ggtaaagcgt gttggtcact   12960
accagcccca gcgtctgagt actcttcgcc gacagattgc gcgccagcaa gtttggacgg   13020
taaccgctct cttctaccgc ctgaaacacg cgatctttag tctcctggct gacgtagcca   13080
ttacctgaaa gcacgcggga aacggtcgct tttgaaaccc cggcgcgctt cgccacttcc   13140
agcatcgtcg tcatcatttt catccctta cacgcaatca acgcagtgta ctgcaccgtt   13200
tgccgattgt ccttgcacaa tcggcgggaa aaatattcag gtgaccggtt tcacaaatat   13260
aaaaaatgaa caattcactc tcttgcttat ttagtgacaa ctattcatga ttttgtgaaa   13320
```

```
ccggtttctt aattccgttt cagcatcggc attttttccgt cacgtcgact gataacaact   13380
acatctaccc tactgataac aggataaaat ccgatggcca aaaattatgc ggcgctggca   13440
cgctcggtga tagcggcact gggcggcgtt gataacatct cggcggtcac gcactgtatg   13500
acgcggttgc gctttgttat caaagatgat gcacttatcg acagcccgac gttaaaaacc   13560
atccccggcg tgctcggcgt ggtacgtagt gacaaccagt gtcaggtgat tatcggcaat   13620
accgtttcac aagcctttca ggaagtcgtc agcctgctgc cggagatat gcagcccgca   13680
cagcccgtgg gtaaacccaa actcacgcta cgtcgcattg gtgcggggat cctcgatgcg   13740
ctgatcggca ccatgtcacc gctgatcccg gcgattatcg gcggatcgat ggtcaaactg   13800
ctggcaatga tcctcgaggt ttttaattt ttcactttcg tcaattggtg aagttttttc   13860
ctcaccgctg tcgccactgg cttgcatgat tagagatctg tagtgtcagg gttctaccac   13920
tctggtcttg taaattcttg ttttggtggc agagctcgga cactacccat gtctggtcct   13980
gtctctgtgt gcgcgcgccg tcgtgggtgt acgcagagtg tgcgcgctcc tgcttgctgc   14040
ggtcctcaga cacgtgcgct cttgtactcg tgtttgtgtt ttcgtctgtc tgcagcgtgg   14100
tgtttcattc ccagcgtctc agtcttgttg gtttcggttt tggtcggcgc tgggatgaag   14160
catgcacgct gcatgtgtca gcgcacggtg agtgttttca ttcatcgtgt gctcatgtct   14220
tgcatctctt atcaaagcac gtggctctgt gtttacattg tggtcacgtg cttttgttgt   14280
gtgcttcagt gttgcttgtt atgaacacgt ggttaatgag cttttttaat tggctgcgtg   14340
ttctagtctc gttttatgtg agcgcatggc ttgtgttgtc tctctgtgtc atgcgctctt   14400
ccgtgtattg tcttgtccca cccaccttgt tatcctgttt gtaattatta ttttcacctg   14460
tcggcctgtc tgttcattgg tttgtctttc ctatttattc tcctagtgtg ctctgttctg   14520
tgctggtccg ttgttgattg ttctcttccc tgttgtatga ggactgctga tttctgttct   14580
acaccagtgg tttaaagtag tgtcttgcca agttccagat cttgtctagt tgagtgtata   14640
atataatgtt gtgttttcc ccacatgggg agatttgagt tttgtttttg ttttattttt   14700
tcaataaatt cttcattccc cgcatttggg tcctcgcctc ctctccatcc accccatac   14760
cctgacatgt agagctgagc attgatggat ttgctcttta gtgtttggac tctcagtggt   14820
gaccaggccc ggattggcta atcgggagga ccgggagaat tcccagtggg ccggtccgtt   14880
ttttggccgc gaggtccggt gtccctagct ccagaatctg ttgctctcag cagtcacact   14940
ttttaaatgt atttatttac ttgaccacag cctttttatt cattatttta ctttaactct   15000
tctgtttttg tctatttaa taatgataaa actcagctgc gcctccttt tgtaatcagc   15060
tgttgtggtc cagcgttag cacttcagtt aaatacgccg ctgatcaggg ttcgatcctc   15120
gatagagcaa tttattgttt tcattttat tgttaagaaa tataatactg ttagggttgt   15180
tgaacatttg aagttctaaa gcagctgttt tctcaaaaaa aaaagacgt gatagtgtca   15240
ttagaaacag atttggaaat gactttattt taatatagtc agttgtgaac tgaggtgggc   15300
cggtctaagg cttgaaactc cagagctgaa aaggtgtccc actccggccc tggtggtgac   15360
tattaaacca cactgaactg agctaaactg aactgaactt aagctgcttt gacacaatct   15420
acattctaaa tgcgcaatac aaatgaaggt gaattgaatt gaattgattt gctgttttgt   15480
ttggtccatg gtaaattttt ttaaatattt ttttcacaga atccaaacaa aatgcttcca   15540
accaaccaaa atgttctccc cgtgttggcg tgggtttcct tcgagtgctc cggtttcccc   15600
aacagcccaa acacatgcgc tacaggtgaa ctgaactaaa ctaaagtggc cgtagtgtat   15660
gagtgtgaat gagtgtgtat ggatgtttcc cagtagtggg ttgccgctgc agggccatcc   15720
```

```
acagtgtaaa gcatatgctg gattagttgg cggttcattc cgtggtggcg acccctgatt    15780
aataaaagga ctaagccaat ggagccaaac ttaataagtg aaccaaataa acaaacaac     15840 aaaaaaagct aaattaactg gaactaaaca aaattaaata aaaaccagac aaaacaaagt    15900
aatcgaaacc actaaaatga ggtggaagaa agccaaactg gattctgtat cattctcttt    15960
tgtgagcagg accaaagtca aaagcaaaca tacctaaatg acagcaacac agacagatct    16020
aaactgaata aacacatata acacatgctt ctgtaaaatag ttgcattaat gagagcatgt    16080
ttataattaa taggcccaca cggaatctgc gcgcagattt ctgcagattt ttagtccatc    16140
attaattctg tttatttact ttttaacttt tattttacta atttattcaa tttttattca    16200
gtaatttatt acttttattt tatatattaa ggttttagtt atgatactcc gctggatact    16260
cccaaaataa ttccgcataa atccacagat ttttaccaaa attctccgca gaaatagcaa    16320
aaaacctccg cagattccat ctggccctac taattaatcc ctaattattt agcaaattaa    16380
gaactatcgt tgttatgaac tgtgtgtagc catttgaatc ttgttcttcg ttataatctg    16440
acgcttccac ttctggattt gctagctctg cgttttgcat gccacataga cttgttgtgg    16500
taaaaactct attttctct ccctgagcta gtacaaggcc aagcgctcgc tcagagaact    16560
atgttgccca agcgctgcc aagttttctg accactccca gagtttaagc agctctcgct    16620
ctgctaataa catactagct gaaaaaaaac tgtgagggac ttgctttaag gagctgtcct    16680
ccttatttaa ttatgtttct ggtgtttgac ctgaaggctt caggtcttgc tgctttgttt    16740
ttttcccata gtccttcaca cacaacacat tgtgtcccac tgagaaatgg aaacgctaaa    16800
agcagcttta aactgctgac aatgatcaac taatcacaca cacacacaca catattaaac    16860
attaaaatat caatgcaagt caaccaactt attttattta tataggactc tactaacttt    16920
aacgtacagt aacatctgag ataaacaata aagtatcatc tccagggacg gattaaggac    16980
atattgggcc ctggggcttt agcaaagagc ctcattatt taatctccta tacttttgc     17040 tattattatt attttgataa ttaaagttat tatctaattt tccaccattt aatttattat    17100
tgattattaa tacataaaaa agtaaagcat acaacaatag tattgattat tccgagtcca    17160
taatagtcca aaaggtgatg ataagcatgg cagtttgccc aggtaaaaaa aaaaaagtgc    17220
actaaaatgc acttttattta aatatacttg gtgcatttt cagtaatgta cgaaaagtgc    17280
tctattttca cacactaatt ttgtacttaa tgtactaaaa gatagtaagt taaacttaat    17340
accatctaag tgtactcaac tgtgctattg agacaccctg aaattgaact aaaatgtgct    17400
tttaacatac tatatctgta ttttaaaaaa tatatttagt tacaactaga aatacacttg    17460
aaccctaatt ttaaacattt ataaatacat ttaagaatag cttaaagcat aatagtaata    17520
tattaaaaga atatacaaaa tgtgaaagca gtgtgctaaa atacacttta agtacactaa    17580
ttatactttt tcagtactgt actaaaagtg ctctatttc acacactaat tttgtaactt    17640
atgtactcaa agatagtatt aagtatatgt taagataaac ttaataccat ctaagtgtac    17700
tcaactgtgc ttttttgaga caccctgaaa ttaaactaaa atgtgctttt aacatattat    17760
atctgtattt taaatatata tatatatatg gctgattcca gcgttatgga tgtgacattt    17820
gcagtaaaaa ttcaaaacat aaattcgcag agaaagtata cgttaacatt atattgaacc    17880
atctgtttat attttccaaa acaactaacc acagagttat gggattaaaa aaattcaatc    17940
tgtgaacatt tttatacttt aaatgaggaa aataaacaag cgttatggat gtgacaaaaa    18000
aagtctgcga gttacagta tacaaacatat ttcgtagaac ttctgtgaat taaactgcac    18060
aacccaaaat aaataatgct caacaaaagc ataagagctg gctctttatt gaacaaaact    18120
```

-continued

```
gattgattt   attttatttt   gacattttg   cattttgag   ggagaagctt   tgttatggat   18180
gtgacacttt  ttcgttatgg   atgtgacgga  tgtgaaattg  tcatttgttt   gactttggta   18240
aatcaaatat  aatagtttga   aaacattgac  agcgacattt  ttaagtattt   ttaaagtact   18300
gtaaaacact  tgcctgcgca   aaaaatgtag  aaacggtttc  gctattttgg   tgaaaacatt   18360
tttcttttca  tggcaaggtt   gacattttca  tggaattgct  catatatata   tatatatata   18420
tatatatata  ttagttacaa   ctagaaatac  acgtttttaa  aatgtcagta   ttgactggta   18480
ctgaattcca  gtatcgtgta   accctagtgg  ccatgaagga  ttcttgtaaa   actctcgatc   18540
atgacaaatc  taaatatcac   ccctagata   aatatcaccc  acatgaacac   gggtatttta   18600
aaaaactatt  tttcctacgt   ggttttgctg  tttgtcaaca  caaaaacagt   gtcaggtgac   18660
taaaaccgta  actttctaaa   aactcaggcc  agggtggaga  ttttcagaaa   ctccgggaac   18720
agcgtggtca  tgtgaacact   acaaccagag  ttttggcctc  atggcatcag   cgtacctgct   18780
gttttatcct  ttctgattgg   ccaacatggc  tgggttgaca  ccaatcgcag   aagatgtgat   18840
tgaggtgatt  ttccagcctg   atctcacgag  gaaacataag  tattttacat   tttgtcagtt   18900
tagtgactaa  tttgtacgaa   ttcgtatgag  tttagtcata  cgaaaatgta   cgattttaaa   18960
aaggaggcgt  gccacctaac   cccacccgtc  actgggtgat  gagcacatcg   tactaaattg   19020
tacgaattag  atcatacaaa   ttaaaacgaa  ttagccacta  aatcaaaaag   ttatgaagtg   19080
ctgcgagatt  gcgttggaat   ttctcacatt  cacaccaaat  gcttcacata   ttcctcgtta   19140
ttcgcatcgc  aggacagtta   tccgtctctg  ttctcacgtt  tgtattgact   tgtatgcagt   19200
gtacaaatac  ttaaatccgt   gtttgcagtg  aacccagcat  gaaagacttt   catcccgct    19260
gttgtttggg  cagtggtgta   gcgcaaaatg  cgggggcccc  cctgcaggga   tcactgacgg   19320
ggtccctga   tgaagggagg   gggggttggt  gggtggagcg  atcacaaact   gagggacgg    19380
ggagagtcgg  tggagcaaca   acgcgaggaa  gcgatcataa  attgaggagc   gggaaagggg   19440
ggcggggtgg  agcgacaaca   cggggtagcg  ttcaaaaaca  actggcgaga   tcgtcaaagt   19500
agccggaagt  cattcatttt   caatgaga                                          19528
```

EXPRESSION OF ZEBRAFISH BONE MORPHOGENETIC PROTEIN 4

BACKGROUND OF THE INVENTION

The bone morphogenetic protein (BMP) family belongs to the transforming growth factor-β (TGF-β) superfamily and includes a group of closely related polypeptides identified initially by their capacity to stimulate ectopic bone formation in vivo. BMPs are synthesized as large precursor proteins before being processed and proteolytically cleaved to form mature carboxyl-terminal dimers. BMP members, such as BMP1 to BMP14, have been known to have different levels of bone morphogenetic activity. For example, BMP2 and BMP4, which are expressed by osteoblasts as they differentiate, have been shown to stimulate osteoblast differentiation and bone nodule formation in vitro. In addition, recombinant BMP2 and BMP4 can induce new bone formation when injected locally into the subcutaneous tissues of rats.

BMPs transduce signals through binding cooperatively to both Type I and Type II receptors, which are trans-membrane serine-threonine kinase receptors. Transphosphorylation of the Type I receptor by the Type II kinase in the cytoplasmic domain triggers a downstream signaling cascade. However, little is known about signal transduction involved in BMP signaling pathways. Effectors (e.g., Mad proteins), which responded downstream to BMP signals, have recently been found in human and *Xenopus* tissues.

Bone morphogenetic protein 4 (BMP4) is a member of the BMP family and, like other BMPs, is a multifunctional regulator during vertebrate development. BMP4 has been shown to play important roles in the establishment of the basic embryonic body plan (e.g., mesoderm formation, left-right asymmetry, dorsal-ventral patterning in vertebrates), in morphogenesis (e.g., skeletal development and limb patterning), and in the development of organs and tissues (e.g., the development of kidney, lung, heart, teeth, gut, and skin, and formation of the central and peripheral nervous system, etc.). In fact, the expression of the bone morphogenetic proteins and their receptors has been identified in a large variety of cells, tissues, and organs, and in specific temporal and spatial patterns.

Mechanisms regulating the expression of bmp genes in vivo are still largely unknown despite the identification of two mouse BMP4 transcripts and cloning of a mouse BMP4 gene. In addition, two human BMP4 transcripts have been identified and two human BMP4 promoter regions have been cloned. The two mouse BMP4 transcripts result from two alternative 5'non-coding exons, 1A and 1B in the BMP4 promoter region. It was found that 1A promoter is primarily utilized in bone cell cultures, and a chicken ovalbumin upstream-Transcription Factor I (coup-TFI) was demonstrated in vitro to negatively regulate murine BMP4 1A promoter in fetal rat calvariae cells. Further, various transcripts resulting from several promoters have been observed for a BMP4 homologue in *Drosophila melanogaster*, decapentaplegic protein (dpp). The use of diverse and separate promoter regions for one BMP4 gene in different cells derived from different tissues suggests a cell-specific or tissue-specific regulation of BMP4 gene expression. Given the unstable half-life of most BMP4 transcripts, expression of bmp genes is largely regulated at the transcriptional level.

Although considerable efforts have been focused on the study of BMP4 function during zebrafish development, the molecular mechanisms regarding the expression of zebrafish BMP4 remain unclear. In contrast to human and murine BMP4, a single transcript has so far been identified for the zebrafish BMP4 gene. The finding and the materials and methods disclosed in the present invention suggest promoter structure, intron/exon organization, and cell-specific and/or tissue-specific regulation of zebrafish BMP4 gene expression are different from human and murine BMP4 despite high level of amino acid sequence homology among BMP4 proteins from humans, mice, and zebrafish.

Therefore, there is a need to understand the regulation of zebrafish BMP4 expression, to provide further insights into molecular mechanisms, regulatory DNA sequences, and transcription factors that regulate development of various BMP4-expressing tissues and organs, and to identify molecular compounds/substances that induce or inhibit the expression of zebrafish BMP4 expression.

Recently, transgenic technology using various reporter genes, e.g., green fluorescent protein (GFP), has provided a powerful means to study gene function and the regulation of gene expression. Thus, there is a need to provide cell lines and transgenic fish to allow real-time imaging of various morphogenetic processes in different cells, organs, tissues, and during embryogenesis.

SUMMARY OF THE INVENTION

The invention generally provides compositions, transgenic fishes, methods, and cell lines involved in the expression of bone morphogenetic protein 4 (BMP4). In one embodiment, the invention provides isolated DNA molecules for a zebrafish bone morphogenetic protein 4 gene (BMP4), its promoter regions, the proximal and distal regulatory regions, and enhancer sequences. The invention provides isolated DNA molecules including nucleic acid sequences of SEQ. ID NO. 1, SEQ. ID NO. 2, SEQ. ID NO. 4, and derivatives and fragments thereof. The amino acid sequences deduced from the sequences of the isolated DNA molecules are included in SEQ. ID NO. 3, SEQ. ID NO. 5, SEQ. ID NO. 6, and derivatives and fragments thereof.

In another embodiment, the invention provides isolated DNA molecules for tissue-specific expression. The isolated DNA molecules are utilized to drive tissue-specific expression of a gene and provide advantageous tools for heterologous gene expression and include nucleic acid sequences of SEQ. ID NO. 1, SEQ. ID NO. 2, SEQ. ID NO. 4, and derivatives and fragments thereof.

In another embodiment, the invention provides recombinant expression vectors containing the DNA sequences of zebrafish bone morphogenetic protein 4 (BMP4) gene, its promoter regions, the proximal and distal regulatory regions, and enhancer sequences, including nucleic acid sequences of SEQ. ID NO. 1, SEQ. ID NO. 2, SEQ. ID NO. 4, and derivatives and fragments thereof. The recombinant expression vectors can further include DNA sequences for heterologous expression products, such as reporter proteins.

Various cell zebrafish embryos and adult fishes containing the DNA sequences for zebrafish bone morphogenetic protein 4 (BMP4) gene, promoter sequences of the zebrafish BMP4 gene, the proximal and distal regulatory regions, and the expression vectors of the present invention are provided for studying the expression of BMP4 gene. The zebrafish embryos and adult fishes of the invention can further include DNA sequences for heterologous expression products.

In another embodiment, the invention provides transgenic fish, such as transgenic zebrafish containing isolated DNA molecules integrated into zebrafish genomic chromosomes, wherein the isolated DNA molecules include zebrafish bone morphogenetic protein 4 (BMP4) gene, promoter sequences of the zebrafish BMP4 gene, the proximal and distal regulatory regions, and derivatives and fragments thereof. The transgenic fish can further include DNA sequences for heterologous expression products.

In yet another embodiment, the invention provides a method for identifying a potential agent, compound, regulator, and/or transcription factor that regulates bone morphogenetic protein-4 expression. The method includes introducing into a cell a recombinant expression vector containing DNA sequences for zebrafish bone morphogenetic protein 4 (BMP4) gene, promoter sequences of the zebrafish BMP4 gene, the proximal and distal regulatory regions, and derivatives and fragments thereof. The method further includes contacting the cell with a candidate compound, and monitoring the expression level of the heterologous expression product to obtain an altered expression level in the presence of the candidate compound and identify the candidate compound as the potential agent.

In yet another embodiment, a method for identifying a potential agent for zebrafish tissue-specific expression includes introducing into a cell a zebrafish tissue-specific expression sequence operatively linked to a nucleotide sequence for a heterologous expression product. The method further includes contacting the cell with a candidate compound and monitoring the expression level of the heterologous expression product in the presence of the candidate compound to identify the candidate compound as the potential agent regulating tissue-specific expression in zebrafish.

In yet another embodiment, a method for screening an effecter (e.g., extracellular stimuli, inhibitors, compounds, or agents, as well as repressors, activators and others) that regulates bone morphogenetic protein-4 expression is provided. An fish embryo or a transgenic fish having a portion of a zebrafish bone morphogenetic protein-4 promoter region and/or the proximal and distal regulatory regions, operatively linked to a heterologous expression product, is constructed. The method includes introducing a foreign DNA from a cDNA library into the embryo or transgenic fish of the invention and monitoring the expression level of the heterologous expression product for a number of the transgenic cell having foreign DNA from the cDNA library. An altered expression level in the presence of the foreign DNA as compared to the absence of the foreign DNA indicates the foreign DNA encodes the effecter.

In yet another embodiment, a method for identifying an expression pattern of a zebrafish BMP4 expression sequence is provided. The method includes providing a zebrafish BMP4 expression sequence and/or the proximal and distal regulatory regions operatively linked to a nucleotide sequence for a heterologous expression product, introducing into a cell the zebrafish expression sequence, and monitoring the expression level of the heterologous expression product, thus identifying the expression pattern (e.g., developmental expression pattern, organ-specific, tissue-specific, or cell type-specific expression patterns) for the expression of BMP4 gene.

BRIEF DESCRIPTION OF THE DRAWINGS

So that the features of the invention can be understood in detail, a more particular description of the invention briefly summarized above may be had by reference to embodiments illustrated in the appended drawings. It is to be noted, however, that the appended drawings illustrate only certain embodiments of this invention should not be considered limiting of its scope, for the invention may admit to other equally effective embodiments.

FIG. 2 is a simplified schematic of the amino acid sequence deduced from the sequence of the cloned zebrafish BMP4 gene and corresponding to SEQ ID No. 3.

FIGS. 6A and 6B are the images of lateral view of prim-8 and long-pec embryos, respectively, examined under fluorescence microscope in DIC mode. FIGS. 6C and 6D are the images showing GFP expression in the heart of prim-8 and long-pec embryos, respectively, which are viewed under fluorescence microscope using FITC filter to localize heart-specific expression as indicated by fluorescence of GFP protein at the arrow. FIGS. 6E and 6F are the microscopic images after immunohistochemistry and cryostat sectioning showing GFP localization in the heart of prim-8 and long-pec embryos, respectively. Arrows indicate GFP localization in the heart. Scale bars represent 100 µm.

FIGS. 7A-7B demonstrate the percentage of GFP expression in a zebrafish embryos population for transient expression analysis of BMP4 promoter activity using various recombinant GFP constructs containing different lengths of the BMP4 promoter and upstream regions. The results of various recombinant GFP deletion constructs are shown in FIG. 7A for heart-specific expression (solid circle) and in FIG. 7B for expression in other regions (solid square), such as skin and muscle of long-pec embryos.

FIGS. 9A, 9B, and 9C illustrate lateral view of $F_1$ embryos examined under DIC or transmitted light mode. FIGS. 9D, 9E, and 9F illustrate lateral view of $F_1$ embryos examined under fluorescence microscope using an FITC filter. FIGS. 9G, 9H, and 9I illustrate combined confocal images of $F_1$ embryos from FITC and bright field modes. FIGS. 9J, 9K, and 9L illustrate the microscopic images after immunohistochemistry and cryostat sectioning showing GFP localization in the heart of $F_1$ embryos, specifically in the myocardium of ventricles (V). Arrows indicate localization of GFP in the heart. A, atrium; B, bulbus arteriosus; V, ventricle. Scale bars represent 100 µm.

DETAILED DESCRIPTION OF THE INVENTION

Unless defined otherwise, all technical and scientific terms used herein have the same meaning as commonly understood by one of ordinary skill in the art to which this invention belongs. All publications mentioned herein are incorporated by reference to disclose and describe the methods and/or materials in connection with the publications cited. In this specification and the appended claims, the singular forms "a," "an," and "the" include plural reference unless the context clearly dictates otherwise.

The invention provides oligonucleotides, an isolated BMP4 gene and its genomic structure, promoter regions, transcriptional regulatory elements, expression vectors, and transgenic fish. The invention provides analysis results for zebrafish BMP4 gene structure and method to study its developmental expression pattern and tissue-specific expression pattern. The invention further provides methods to identify regulatory elements (e.g., enhancers, silencer, and the like), transcriptional regulators (e.g., repressors, activators and the like), and other effectors (e.g. extracellular stimuli, compounds and agents) that contribute to BMP4 gene expression in general and for specific organ-specific, tissue-specific, or cell type-specific expression.

I. BMP4 Gene and Isolation of BMP4 Gene

Figure 1:
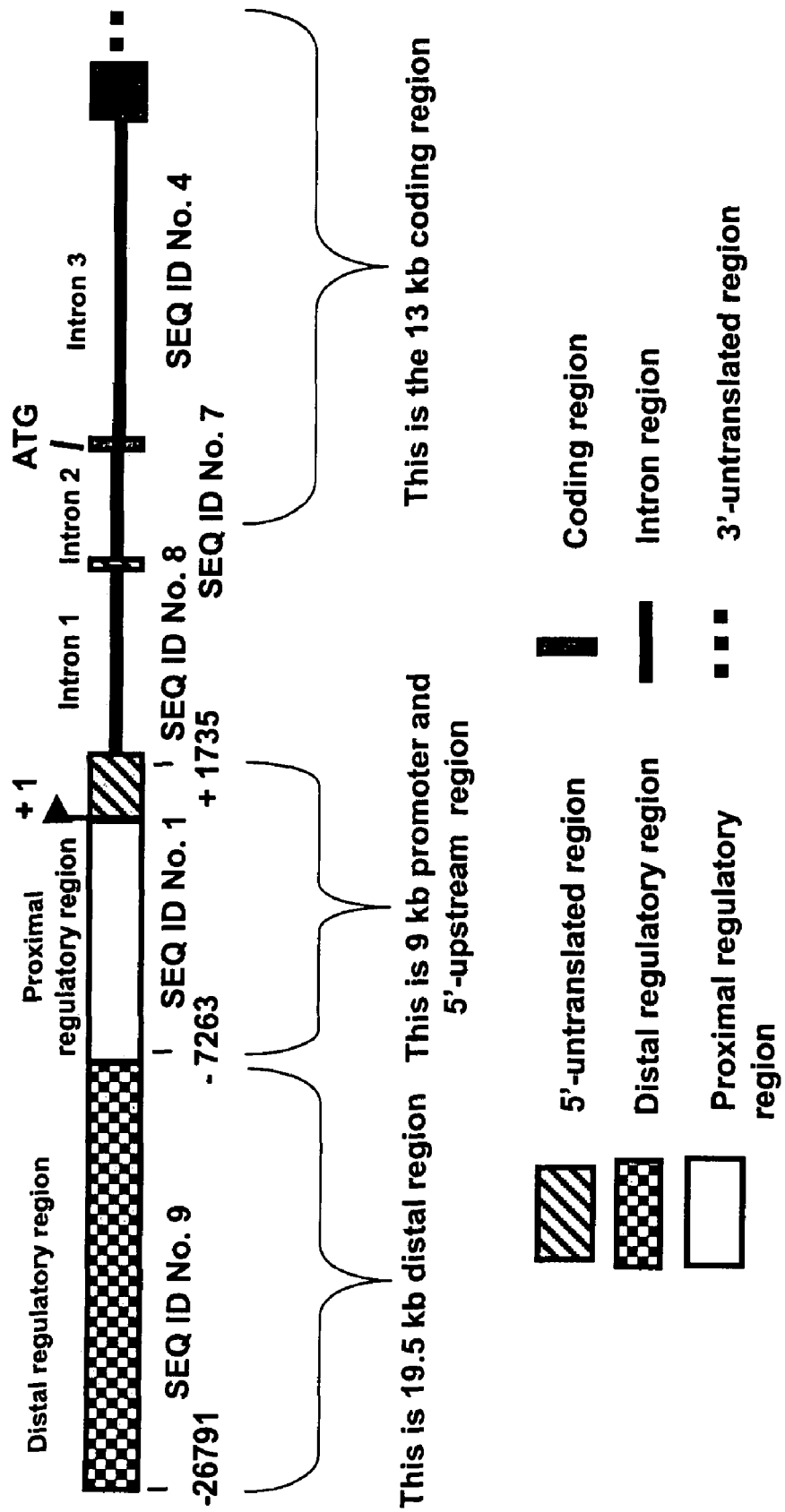
FIG. 1 is a simplified schematic of the structural organization of the zebrafish BMP4 gene containing exons 1, exons 2, exons 3, exons 4, intron 1, intron 2, intron 3, coding regions, 5'-untranslated regions, 3'-untranslated regions, promoter regions, and proximal and distal regulatory sequences.

We have cloned and identified the zebrafish BMP4 gene. The zebrafish BMP4 genomic structure including its 5'-untranslated region (5'UTR), exons 1, exons 2, exons 3, exons 4, intron 1, intron 2, intron 3, coding regions, 3'-untranslated region (3'UTR), promoter regions, and proximal and distal regulatory sequences is shown in FIG. 1. As shown in FIG. 1, the zebrafish BMP4 gene transcription unit contains 4 exons and spans at least approximately 36 kb. There are total of 4 exons (exons 1-4) and 3 introns (intron 1-3) for zebrafish BMP4 gene. As a comparison, human and mouse BMP4 genes contain 5 exons and span approximately 7 kb. The sizes of the introns mainly contribute to the size differences of these BMP4 genes. We have found out that the sizes of the three zebrafish BMP4 introns, about 6 kb, about 3.5 kb, and about 8.9 kb, respectively, are larger than the sizes of four human BMP4 introns (about 1.9 kb, about 1.1 kb, about 1.2 kb, and about 1 kb) and four mouse BMP4 introns (about 2.1 kb, about 0.8 kb, about 1 kb, and about 1 kb).

In FIG. 1, two coding exons, exon 3 and exon 4, corresponding to the coding regions are shown in gray boxes. Two exons, exon 1 and exon 2, corresponding to the 5'-untranslated regions are shown in hatched boxes. Two introns, intron 1 and intron 2, are located in the 5'-untranslated region. The 3'-untranslated region is shown as a dotted line. Also shown are two restriction enzyme sites, Xho I and Age I, located at the +1735 and −7263 positions relative to the transcription start site (designated as +1), respectively. An arrow also denotes the transcription start site. A proximal regulatory region is shown as open box spanning from about +1 to about −7263. A distal regulatory region is also identified and shown as mosaic boxes spanning for a length of about 19,528 bp, shown as the 19.5 kb distal regulatory region in FIG. 1 and located at the position from about −7263 to about −26791.

The invention provides SEQ ID No. 4 having a length of about 13,382 base pairs and including part of intron 2, exon 3, intron 3, and exon 4, shown as the 13 kb coding region in FIG. 1. The nucleic acid sequences of SEQ ID No. 4 described herein have been deposited into GenBank under accession no. AF056336. The nucleic acid sequences of exon 3 and exon 4 include the coding regions corresponding to two DNA fragments located from position 2,637 to position 2,984 and from position 11,948 to position 12,802 of the 13,382 bases DNA sequences of SEQ ID No.4. The deduced amino acid sequences of the two coding regions are listed in SEQ ID No. 5 (N-terminal portion) and SEQ ID No. 6 (C-terminal portion).

The two coding regions are connected by intron 3. Nucleotide sequence comparison of the identified intron 3 with genes in the sequence databank of National Center for Biotechnology Information (NCBI) exhibited a high degree of sequence homology with a DANA retroposon element. The DANA retroposon element of BMP4 gene is located in the first unusually long intron, intron 3. This DANA retroposon element has also be found in various zebrafish genes, such as eIF-4E, ependymin, no tail, and major histocompatibility-II genes (alignment data not shown). The homology extends to regions corresponding to four conserved DANA boxes and flanking directed repeats of 9-nucleotide sequences (GTTT-TAATA). Compared to other DANA elements with four conserved boxes, the sequence of the DANA retroposon element in BMP4 gene contains boxes #1 and #4 that are highly conserved among DANA elements. However, boxes #2 and #3 of the DANA retroposon element in BMP4 gene show lower sequence similarity to the sequences of other DANA elements. The conserved boxes #1 and #4 contain sequences that are similar to the sequences of A box and B box internal control regions of tRNA gene promoter. In addition, we have identified a pair of 9-nucleotide direct repeats (GTTT-TAATA) flanking these four conserved boxes and the results further support that such a DANA-like (Danio retroposon A) SINE (short interspersed elements) element is widely distributed in the zebrafish genome. Furthermore, the DANA-like SINE element may have been captured at a site of DNA breakage as suggested recently by the studies on yeast retrotransposon Ty1 element. The question of why such a large intron is present in lower vertebrates like zebrafish remains to be answered.

We have also isolated a 9.0-kb DNA fragment containing a BMP4 promoter region and adjacent regulatory region, generated by Age I and Xho I restriction digestions at the −7263 and at +1735 positions relative to the transcription start site and is shown as the 9 kb promoter and 5'-upstream region in FIG. 1. Thus, the invention provides SEQ ID No. 1 having a length of about 9,100 base pairs and including part of exon 1, promoter regions, and proximal regulatory DNA sequences. The nucleic acid sequences of SEQ ID No. 1 described herein have been deposited into GenBank under accession no. AY156927.

We have determined the transcription start site of BMP4 gene through 5' Rapid Amplification of cDNA Ends (5' RACE) and found no TATAAT-like core promoter element near the transcription initiation site. Thus, zebrafish BMP4 gene contains a TATA-less promoter to direct the transcription of zebrafish BMP4 gene having a transcript size of about 3,800 bases as revealed by Northern blotting analyses. Similarly, mammalian BMP4 genes are also directed by TATA-less promoters. Also provided herein is the zebrafish BMP4 mRNA sequence having a length of about 1790 bases as shown in SEQ ID No. 2, which can be deduced from the DNA sequences of the BMP4 genomic DNA, e.g., SEQ ID No. 4. The mRNA sequences of SEQ ID No. 2 described herein have been deposited into GenBank under accession no. NM_131342.

The deduced amino acid sequence from the mRNA sequence is shown as SEQ ID No. 3, having the complete 400 amino acid sequences of BMP4 protein. It is observed that the combined sequences of the two amino acid coding sequences, SEQ ID No. 5 (N-terminal portion) and SEQ ID No. 6 (C-terminal portion), deduced from the genomic DNA sequences of SEQ ID No. 4, are identical to the amino acid sequence of SEQ ID No. 3, deduced from the mRNA sequence of SEQ ID No. 2. The deduced amino acid sequence of the coding regions of the zebrafish BMP4 gene is also shown in FIG. 2.

We have found that the zebrafish BMP4 gene encodes a protein of 400 amino acids, about 8 amino acids shorter in size than mammalian BMP4 proteins. Sequence comparison reveals that zebrafish BMP4 protein shares about 73% amino acid sequence similarity with human and mouse BMP4 proteins, whereas it shares only about 63% amino acid sequence similarity with human and mouse BMP2 proteins. Similar to human BMP4 protein, there are 7 conserved cysteine residues present in the carboxyl-terminal domain of zebrafish BMP4 protein. Dibasic amino acids (RAKR) are present in zebrafish BMP4 protein and are located at similar regions in human BMP4 protein. These dibasic amino acids may serve as proteolytic cleavage sites for the generation of mature carboxy-terminal portions. However, only three potential N-linked glycosylation sites are present in the zebrafish BMP4 protein as compared to four glycosylation sites in human BMP4 protein.

Both 5' and 3' intron-exon splice junctions in the coding regions were conserved between zebrafish and mammalian BMP4 genes. However, intron 1 of the zebrafish BMP4 gene is much larger than those found in human and mouse genes. Intron 1 and intron 2 are located in the 5' untranslated region (5'UTR) with sizes of about 6 kb and 3.5 kb, respectively. The invention also provides SEQ ID No. 7 having a length of about 3.5 kb and including the DNA sequences of intron 2, and SEQ ID No. 8 having a length of about 6 kb and including the DNA sequences of intron 1 and 122 bp of exon 2. The DNA sequences of exon is included in the 9 kb DNA fragment containing the BMP4 promoter region and adjacent regulatory region.

Additional screening of genomic clones has led to the identification of other DNA fragments that also contain sequences that may function as BMP4 promoter regions. For example, DNA sequences spanning about 19.5 kb in the 5' upstream regions and being more distal to the 9 kb Age I-Xho I promoter region/proximal regulatory region have been isolated. We have analyzed the function of this 19.5 kb DNA region and found out that it contains additional transcriptional regulatory elements for BMP4 gene expression. Thus, the invention also provides SEQ ID No. 9 having a length of about 19.5 kb that includes distal regulatory DNA sequences.

II. Use of BMP4 Gene

The invention provides nucleic acid compositions for BMP4 gene, homologs and fragments thereof. Furthermore, the invention also provides coding sequences encoding BMP4 polypeptides, homologs and fragments thereof, and methods for producing and purifying recombinant BMP4 protein in vitro through recombinant DNA technology. In addition, nucleic acid compositions for BMP4 gene are useful in controlling expression of BMP genes during development and identifying chemical compounds, factors, agents, or other substances that affect (e.g., stimulate or inhibit) regulation of BMP4 gene expression.

The nucleic acid compositions of the invention may encode all or a part of the polypeptides for the BMP4 gene. Double- or single-stranded fragments of the DNA sequence may be obtained by chemically synthesizing oligonucleotides in accordance with conventional methods, by restriction enzyme digestion, by PCR amplification, etc. For the most part, DNA fragments will be of at least 15 nucleotides, usually at least 18 nucleotides or 25 nucleotides, and may be at least about 50 nucleotides. Small DNA fragments are useful as primers for PCR, hybridization screening probes, etc. Larger DNA fragments, i.e., greater than 100 nt, are useful for production of a protein or polypeptide.

Altered nucleic acid sequences encoding the BMP4 gene may include deletions, insertions, or substitutions of different nucleotides resulting in a polynucleotide that is the same or a functional equivalent of the BMP4 endogenous gene product. Such analysis is useful to study the sequences that are crucial to the expression of BMP4 gene and the function of the BMP4 protein. For example, altered nucleic acid sequences of the BMP4 gene may be used to generate changes in promoter strength or sequences of the encoded proteins. The encoded protein may also contain deletions, insertions, or substitutions of amino acid residues, which, as an example, produce silent changes and result in functionally equivalent BMP4 protein or, as another example, promote a different folding of the encoding proteins or decrease substrate fidelity. Deliberate amino acid substitutions may be made on the basis of similarity in polarity, charge, solubility, hydrophobicity, hydrophilicity, and/or the amphipathic nature of the residues as long as the biological activity of the BMP4 gene is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine. Such alterations to the BMP4 gene may be made to increase expression, allow for purification, or to add cross-linking groups to make the BMP4 protein more reactive and capable of being fused to another heterologous gene product.

A. BMP4 Protein Expression

In order to obtain the BMP4 protein, cloning of the BMP4 coding sequences of the invention into a recombinant expression vector for recombinant protein expression may be necessary. A recombinant expression vector may contain necessary elements for transcription and/or translation of the inserted coding sequences. Recombinant expression vectors and systems known in the art may be employed for producing full length or only portions of the BMP4 polypeptides of the invention.

For long-term, high-yield production of recombinant proteins, stable expression of the DNA construct of BMP4 protein is preferred. For example, cell lines which stably express the BMP4 protein may be transformed using recombinant expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells, which successfully express the introduced sequences. Resistant clones of stably transformed cells may be proliferated using tissue culture techniques appropriate to the cell type. As another example, a host cell strain may be chosen for its ability to modulate the expression of the inserted sequences or to process the expressed proteins or peptides in a desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

Production of the BMP4 protein may be as insoluble inclusion body fusion proteins. For example, expression of BMP4 protein may be toxic to a host cell; thus an expression vector for high level-expression of insoluble protein is chosen to avoid the expression of soluble active BMP4 protein. Alternatively, genomic DNA encoding the mature proteins for BMP4 are produced and isolated without signal peptides in order to express the recombinant proteins inside the host cells without processing through the secretory pathway of the host cells.

In yet another approach, natural, modified, or recombinant nucleic acid sequences encoding the BMP4 protein may be ligated to a heterologous sequence to encode a fusion protein. For example, it may be useful to encode chimeric proteins that can be recognized by commercially available antibodies. A fusion protein may also be engineered to contain a cleavage site located between the encoding sequences for the BMP4 protein, and the heterologous protein sequences, so that the BMP4 protein may be cleaved and purified away from the heterologous moiety.

With the availability of the protein or fragments in large amounts, the recombinant BMP4 protein may be isolated and purified in accordance with conventional methods. Again, see Sambrook, J., et al. (1989) Molecular Cloning, A Laboratory Manual, Cold Spring Harbor Press, Plainview, N.Y., and Ausubel, F. M. et al. (1989) Current Protocols in Molecular Biology, John Wiley & sons, New York, N.Y. A lysate may be prepared of the expression host and the lysate purified using HPLC, exclusion chromatography, gel electrophoresis, affinity chromatography, or other purification techniques. The purified proteins will generally be at least about 80% pure, preferably at least about 90% pure, and may be up to and including 100% pure. Pure is intended to mean free of other proteins, as well as cellular debris.

For the production of antibodies, various hosts including goats, rabbits, rats, mice, humans, and others, may be immunized by injection with the purified BMP4 protein or fusion protein obtained or fragments or oligopeptides thereof that have immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol.

In summary, nucleotide sequences of BMP4 proteins can be engineered using methods generally known in the art. As a result, altered coding sequences, including but not limited to, alterations, which modify the cloning, processing, and/or expression of the gene product, are obtained.

B. BMP4 Gene Expression

The BMP4 gene is isolated and its genomic structure is analyzed using methods of the invention. A genomic sequence of interest, such as the isolated BMP4 genomic sequence, includes nucleic acid sequences present between the initiation codon and the stop codon, containing all of the introns that are normally present in a native chromosome. The genomic sequences of the invention include the 3' and 5' untranslated regions found in the mature mRNA. The sequences also include specific transcriptional and translational regulatory sequences, such as promoters, enhancers, etc., including about 1 kb to 10 kb or more of flanking genomic DNA at either the 5' or 3' end of the transcribed region. Genomic DNA is isolated as a DNA fragment of 100 kb or smaller that is substantially free of flanking chromosomal sequence. Sequences required for proper tissue-specific and stage-specific expression are also cloned from genomic DNA flanking the coding region (either 3' or 5') and internal regulatory sequences, such as in introns.

Of particular interest is the zebrafish BMP4 gene. SEQ ID NO. 4 provides the nucleotide sequences of a genomic DNA clone having a size of about 13882 bp and containing the zebrafish DNA sequence encoding the full-length zebrafish BMP4 protein. The subject BMP4 nucleic acids may be cDNAs or genomic DNAs, as well as fragments thereof. The term "BMP4 gene" shall be intended to mean the open reading frame encoding BMP4 proteins and polypeptides, exons and introns of such genes, promoter regions, its proximal and distal regulatory sequences as well as adjacent 5' and 3' non-coding nucleotide sequences involved in the regulation of expression, up to about 25 kb beyond the coding region, but possibly further in either direction. The gene is then cloned into an appropriate vector, such as a plasmid vector, for extra-chromosomal maintenance or for integration into a host genome. Methods well known to those skilled in the art may be used to construct cloning vectors containing appropriate transcriptional and translational control elements and DNA sequences. Exemplary techniques are described in Sambrook, J. et al. (1989) Molecular Cloning, A Laboratory Manual, Cold Spring Harbor Press, Plainview, N.Y., Ausubel, F. M. et al. (1989) Current Protocols in Molecular Biology, John Wiley & Sons, New York, N.Y., and Green, E. et al. (1997) Genome Analysis, A Laboratory Manual, Cold Spring Harbor Press, Plainview, N.Y.

In order to carry out certain aspects of the invention, primers may be used to amplify the genomic or cDNA sequences of the BMP4 gene. For example, DNA fragments containing all or portions of the BMP4 coding sequences may be used as probes for cloning of other BMP4 genes or additional clones having adjacent 5' and 3' non-coding regulatory sequences using hybridization screening techniques, PCR amplification/cloning techniques, or others. For instance, degenerate primers can be used for cloning of the zebrafish BMP4 gene and amplifying BMP4 genes. In addition, specific primer pairs and portions or fragments of the nucleic acid sequences of the invention can be used to screen and isolate additional BMP4 genomic clones.

Also provided are isolated DNA sequences encoding promoter and/or proximal regulatory regions of BMP4 gene. For example, SEQ ID No. 1 is provided herein as promoter and proximal regulatory regions of BMP4 gene, including genomic DNA fragments of about 9,100 bp.

As an example, the sequences of three large genomic fragments (SEQ ID No. 7, SEQ ID No. 8, and SEQ ID No 9) in the 5' flanking region are also identified and may be modified to effect promoter elements and/or enhancer binding sites, to provide developmental regulation in various cells, tissues, and organs where expression of the BMP4 gene is desired. Thus, the invention provides analyses and methods to identify DNA sequences or DNA regions required for controlling gene expression in a cell-, tissue-, or organ-specific manner.

Such cell type specific controlling expression element is useful for determining the expression pattern of the gene, and for providing promoters that mimic the native expression pattern. Naturally-occurring polymorphisms in the promoter region are useful for determining natural variations in expression, particularly those that may be associated with diseases.

Alternatively, mutations, deletions, insertions, and substitutions may be introduced into various promoter regions to alter the expression of the nucleic acid sequence. In addition, methods for the identification of specific DNA motifs involved in the binding of transcriptional factors are known in the art, e.g., sequence similarity to known binding motifs, gel retardation studies, etc. For examples, see Blackwell et al. (1995) Mol Med 1: 194-205; Mortlock et al. (1996) Genome Res. 6: 327-33; and Joulin and Richard-Foy (1995) Eur J. Biochem 232: 620-626. Regulatory DNA sequences that show function in regulating gene expression may be used to identify cis acting sequences required for transcriptional or translational regulation, such as for the expression of the BMP4 gene, especially in different tissues or stages of development, and to identify trans acting factors and/or effectors, such as activators, repressor, and the like, which regulate or mediate gene expression, as described in detail infra. Such transcription or translational control regions may be operably linked to a heterologous gene, such as a reporter gene, in order to promote expression of wild type or altered BMP4 genes in cultured cells, or in embryonic, fetal, or adult tissues, to generate transgenic fish, and for gene therapy.

Techniques for in vitro mutagenesis of cloned genes are known. Examples of protocols for site-specific mutagenesis may be found in Gustin et al. (1993) Biotechniques 14:22; Barany (1985) Gene 37:111-23; Colicelli et al. (1985) Mol Gen Genet 199:537; and Prentki et al. (1984) Gene 29:303-13. Methods for site specific mutagenesis can be found in Sambrook et al., Molecular Cloning: A Laboratory Manual, CSH Press 1989, pp. 15.3-15.108; Weiner et al., Gene 126: 35-41 (1993); Sayers et al. Biotechniques 13:592-6 (1992); Jones and Winistorfer, Biotechniques 12:528-30 (1992); Barton et al., Nucleic Acids Res 18:7349-55 (1990); Marotti and Tomich, Gene Anal Tech 6:67-70 (1989); and Zhu, Anal Biochem 177:120-4 (1989).

II. Regulation of BMP4 Expression

The nucleic acid compositions of the invention are useful in delineating the regulation of BMP4 expression, such as the expression of zebrafish BMP4 mRNA and BMP4 protein during embryonic development, in order to attenuate BMP4 expression and identify additional factors and compounds involved using screening methods of the invention. For example, a method for identifying an expression pattern of a zebrafish BMP4 expression sequence includes providing a zebrafish BMP4 expression sequence operatively linked to a nucleotide sequence for a heterologous expression product. The zebrafish BMP4 expression sequence includes, but is not limited to, DNA sequences for bone morphogenetic protein 4 (BMP4) gene, such as SEQ ID NO. 1, SEQ ID NO. 4, SEQ ID NO. 7, SEQ ID NO. 8, and SEQ ID NO. 9. The method further includes introducing into a cell the zebrafish expression sequence, and monitoring the expression level of the heterologous expression product, thus identifying the expression pattern for the expression of BMP4 gene.

A. Expression of Zebrafish BMP4 mRNA during Embryonic Development

Expression of zebrafish BMP4 mRNA during zebrafish embryonic development may be determined by Northern blot analysis. A mRNA with an approximate size of about 3.8 kb is detected at the gastrula stage. The amounts of BMP4 mRNA increase to a maximum level at the pharyngula stage and maintain at a slightly lower level throughout the month-long larval stage in the presence of an equal amount of total RNA loaded for each stage. In contrast, the mammalian BMP4 gene has two alternatively spliced mRNAs with much smaller sizes: about 1.5 kb and about 1.7 kb in human, and about 1.8 kb and about 2.1 kb in mouse.

Because Northern blot analysis is less sensitive than RT-PCR, the tissue and organ distribution of zebrafish BMP4 mRNA is also examined by the latter technique. The expression of BMP4 mRNA during embryonic development determined by reverse transcription polymerase chain reaction (RT-PCR) is similar to the mRNA expression pattern from Northern blot analysis, showing BMP4 mRNA expression from gastrula stage up to 1-month-old larvae. In addition, results from RT-PCR analysis suggest that the BMP4 mRNA is also expressed at other developmental stages, e.g., at both the cleavage and blastula stages during embryonic development and also at adult stage, as shown by the presence of the BMP4 specific RT-PCR product of about 400 base pair. We have further confirmed the identity of the amplified RT-PCR DNA through Southern blot analysis using BMP4 DIG-labeled DNA probe. By using the α-chain gene as an internal control, we have shown that the observed developmental profile of BMP4 mRNA does not result from an uneven amount of total RNA used in the RT-PCR reaction.

Therefore, the temporal and spatial mRNA expression patterns of zebrafish BMP4 are thoroughly analyzed. In zebrafish early development, BMP4 mRNA is localized in the ventral part of gastrula embryos. During later embryonic development, BMP4 expression becomes restricted to certain regions within several organ primordia. For example, in pharyngula stage embryos, BMP4 is expressed in the olfactory placode, eyes, otic vesicles, heart, pronephric ducts, anus, gut, and pectoral and caudal fin buds.

B. Expression of Zebrafish BMP4 Protein during Embryonic Development

To examine BMP4 protein expression, as an example, we have first overexpressed a BMP4 fusion protein to be used as an antigen for the production of antibody. A 9-kD fusion protein is over-expressed from E. coli cells transformed with a recombinant plasmid carrying portions of the coding sequences of the cloned BMP4 gene. Upon IPTG induction, the 9-kD fusion protein is purified and used as an antigen to raise polyclonal antibodies using standard techniques. The resulting antisera recognize the 9-kD fusion protein specifically, as represented by a strong band after Western Blot analysis.

The specificity of the antisera is further tested against human TGF-β1 and BMP2 recombinant proteins. The results demonstrate that the antisera recognize with high affinity a human BMP2 recombinant protein of about 17-kD and a protein of about 18-kD from cholate-extractable total protein isolated from 11-day-old zebrafish hatching larvae. The antisera also recognize a protein of about 12.5 kD, indicating weak affinity with the human TGF-β1 recombinant protein.

The expression of BMP4 protein is also examined by Western blot analysis. Trace amounts of a protein of about 18-kD are detected at the pharyngula stage, and increasing level of expression is observed from hatching larval stages to adult fish stage during embryonic development. The size of the BMP4 protein is consistent with the expected value derived from the number of amino acid residues present in the predicted mature protein after cleavage of the predicted signal peptide from the preprotein and the presence of one N-linked glycosylation site. Several high-molecular-weight immunoreactive bands are also observed. They may represent different species of prepropeptides or another member of the BMP family (e.g., BMP2), because the fusion protein encompasses the most conserved carboxy-terminal domain.

Therefore, BMP4 mRNA is abundantly expressed from gastrula stage through adult stage, whereas zebrafish BMP4 protein is actively produced from pharyngula stage to adult stage. One possible explanation of the discrepancy between the expression of the mRNA and the putative mature 18-kD BMP4 protein is that the processing efficiency of BMP4 precursors from cleavage stage to pharyngula stage is low and thus yields a lower level of mature 18-kD BMP4 protein during this period. This could be the cause of the observed time lag because high-molecular-weight bands are observed from cleavage stage to pharynula stage (data not shown).

Prominent developmental events from pharyngula to hatching stage include the development of jaw, gill, and fin and the establishment of many organ rudiments, except for endodermal structures. During the larval period, the development of alimentary tracts, gill filament, jawbone, various skeleton, and fin rays continues. Thus, the appearance of both BMP4 mRNA and protein during this period of zebrafish development implies BMP4 may be required by some of these events. In comparison, mammalian BMP4 has also been shown to play important roles in organogenesis. For example, mouse BMP4 mRNA expression was suggested to be required for the formation of heart, pituitary gland, limb, craniofacial process, and gut.

The presence of BMP4 mRNA in adult fish suggests that the function of BMP4 is not restricted to organogenesis during embryonic development. The expression of BMP4 mRNA was observed in the brain, heart, digestive tracts, testes, and jaw. On the other hand, in adult mice, BMP4 mRNA has been detected with high levels of expression in spleen and lung, low levels of expression in liver, and no expression in brain, heart, and kidney. The level of BMP4 mRNA in these organs also increases with age. These results suggest that BMP4 may help to maintain the function of various organs and tissues in adult phase.

IV. Zebrafish BMP4 Promoter Regions

The invention provides isolated DNA sequences encoding promoter regions and proximal and distal regulatory sequences of BMP4 gene, and a method for identifying and evaluating agents, factors, or compounds important for BMP4 gene expression. The method is provided for identifying a potential extracellular stimulus, inhibitor, agent, compound, substance, regulator, and/or transcription factor (e.g., repressors, activators and others) that regulates bone morphogenetic protein-4 expression. The method includes introducing into a cell a recombinant expression vector containing DNA sequences for zebrafish bone morphogenetic protein 4 (BMP4) gene, promoter sequences of the zebrafish BMP4 gene, proximal and distal regulatory sequences, 5' and 3' non-coding regions, and derivatives and fragments thereof. The method further includes contacting the cell with a candidate compound, and monitoring the expression level of the heterologous expression product to obtain an altered expression level in the presence of the candidate compound and identify the candidate compound as the potential agent, compound, substance, regulator, and/or transcription factor. Examples of the method are also described in FIGS. 4 and 5 as described in section VII and in the Experimental section below.

Further, the activity of the BMP4 promoter and the effect of the proximal and distal regulatory sequences are analyzed in zebrafish embryos via transient and stable transgenic expression analyses. For example, the results of deletion of portions or fragments of the promoter and regulatory sequences provide a basis for understanding the mechanism of BMP4 gene expression in general and, specifically, BMP 4 gene expression patterns during different developmental stages and cell-specific and tissue-specific regulation of BMP4 gene expression. In addition, mixing various portions or fragments of the promoter and regulatory sequences together through reconstitution, ligation, co-transfection of these portions or fragments of the promoter and regulatory sequences is also useful in understanding the function of different promoter region and regulatory DNA sequences.

Significantly, promoter regions and proximal and distal regulatory sequences of BMP4 gene are used in a method of identifying potential agents for zebrafish tissue-specific expression. First of all, a zebrafish tissue-specific expression sequence is identified using methods of the invention, such as deletion analyses and reconstitution (e.g., co-transfection, ligation) of important promoter and regulatory DNA sequences. Secondly, the method includes introducing into a cell the zebrafish tissue-specific expression sequence operatively linked to a nucleotide sequence for a heterologous expression product. The method further includes contacting the cell with a candidate compound and monitoring the expression level of the heterologous expression product in the presence of the candidate compound to identify the candidate compound as the potential agent regulating tissue-specific expression in zebrafish.

A. Identification of BMP4 Promoter Regions

We have isolated genomic DNA containing at least one BMP4 promoter and its upstream proximal and distal regulatory regions to direct BMP4 gene expression in different tissues, cells, and organs. The genomic DNA fragments are isolated after screening a zebrafish genomic DNA library. We have obtained several genomic clones that contain BMP4 promoter and its upstream proximal and distal regulatory regions through screening with BMP4 specific DNA probes having a length of about 250 b.p. and about 300 b.p. which are products of PCR amplification using BMP4 specific primers. Positive clones are then examined by restriction enzyme mapping, subcloning, and sequencing.

The genomic DNA fragments containing putative promoter and the upstream proximal and distal regulatory regions can be introduced into various expression vectors to direct the expression of a DNA sequences for heterologous expression products. The resulting recombinant expression construct includes a genomic DNA fragment containing the promoter and/or its upstream proximal and distal regulatory regions fused to DNA sequences of a heterologous gene, such as a reporter gene for the expression of a reporter protein. For example, genomic DNA fragments of zebrafish bone morphogenetic protein 4 (BMP4) gene containing its promoter, upstream proximal and distal regulatory regions, 5'-non-coding region, introns, and/or enhancer sequences, are identified and provided herein as nucleic acid sequences of SEQ. ID NO. 1, SEQ. ID NO. 4, SEQ. ID NO. 7, SEQ. ID NO. 8, SEQ. ID NO. 9, and derivatives and fragments thereof.

Useful reporter genes are characterized as being easy to transfect into a suitable host cell, easy to detect using an established assay protocol, and genes whose expression can be tightly regulated. Reporter genes contemplated to have utility include, but are not limited to, the luciferase gene, the Green Fluorescent Protein (GFP) gene, the chloramphenicol Acetyl Transferase gene (CAT), human growth hormone, alkaline phosphatase, β-glucuronidase, and β-galactosidase. Additional useful reporter genes are any well characterized genes the expression of which is readily assayed, and examples of such reporter genes can be found in, for example, F. A. Ausubel et al., Eds., Current Protocols in Molecular Biology, John Wiley & Sons, New York, (1989). As will be appreciated by those having ordinary skill in the art, the listed reporter genes are only a few of the possible reporter genes, and it is only for ease of description that all available reporter genes are not listed.

The resulting recombinant expression constructs are generally analyzed through a series of deletion analyses. In order to define regions responsible for constitutive and regulated BMP4 gene expression, the activity of a chimeric GFP reporter gene containing different DNA fragments of the 5' flanking regions is analyzed in various cell lines, embryos, or cell lines derived from the embryos, for example, microinjection into zebrafish embryos at their 1-cell or 2-cell stage. Other cells or cell lines can also be used. It was found that two large DNA fragments of about 9 kb (SEQ. ID NO. 1) and about 28.5 kb (SEQ. ID NO. 1 plus SEQ. ID NO. 9) exhibit a high level of constitutive gene expression as judged by the constitutive reporter gene expression, e.g., constitutive GFP activity, but in the sense orientation only. Endogenous BMP4 expression as represented by the level of GFP expression is constitutively expressed in the heart, hatching gland, caudal fin, and eye, etc. during zebrafish embryonic development. The recombinant expression constructs can also be used to analyze regulated BMP4 expression in the presence of a stimulating or inhibiting agent, compound, or transcription factor (e.g., activator, repressor, and others).

For example, a genomic DNA fragment of about 9 kb (SEQ. ID NO. 1) is cloned into an expression vector, such as an EGFP-ITR vector, as described in the Experimental section, to be fused with DNA sequences of a GFP reporter gene. Different 5'-deleted DNA fragments of BMP4 proximal promoter region and upstream regulatory sequences are generated by suitable restriction enzymes and exo III deletion. The resulting restriction map of at least seven expression constructs containing the heterologous reporter gene generated is shown in FIG. 3.

Figure 3:
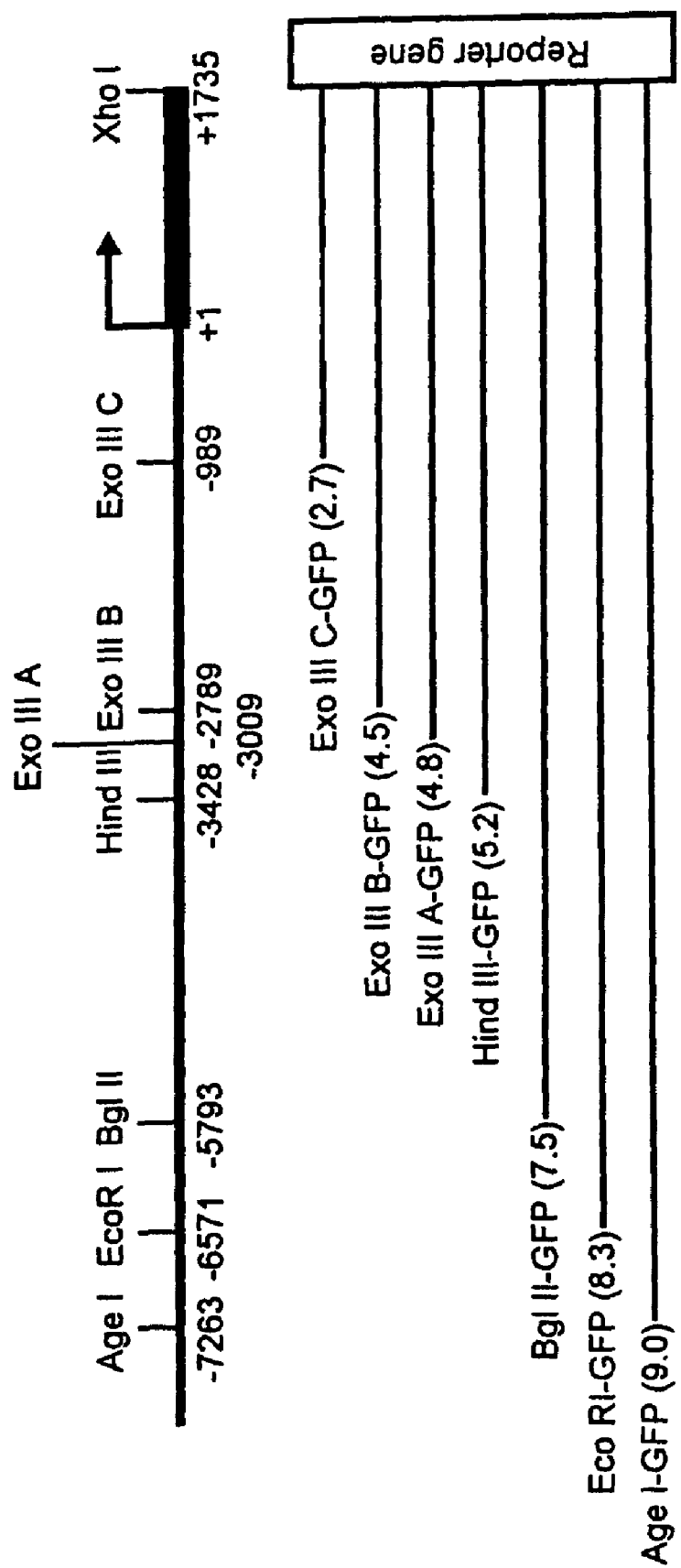
FIG. 3 is a schematic diagram of various 5'-deleted BMP4 promoter-GFP constructs.

In FIG. 3, a 9.0-kb Age I-Xho I DNA fragment contains a BMP4 promoter, a proximal regulatory region, and the 5'-noncoding region is shown on the top and the nucleic acid positions corresponding to the 5'-end of each deletion construct are also shown. The. Seven exemplary deletion constructs fused to a reporter gene are also shown. The lengths of the corresponding BMP4 DNA fragments of the seven expression constructs are estimated to be about 9 kb, about 8.3 kb, about 7.5 kb, about 5.2 kb, about 4.8 kb, about 4.5, and about 2.7 kb for Age I-GFP, EcoR I-GFP, Bgl II-GFP, Hind III-GFP, Exo III A-GFP, Exo III B-GFP, and Exo III C-GFP, respectively, and are shown in parenthesis. Partial exon 1 containing the 5'-untranslated region is shown by the black box. An arrow also denotes the transcription start site, designated as +1. An enhanced green fluorescent protein (GFP) is used as an exemplary reporter gene. In addition, an expression construct containing CMV promoter/enhancer cloned into the GFP expression vector is used as a control. These expression constructs are linearized and microinjected into zebrafish 1-cell zygotes for transient expression analyses and generating stable transgenic fish cell lines.

TABLE 1

Transient expression analysis of BMP4 promoter activity in zebrafish Embryos

| DNA constructs (Number of embryos) | Heart expression (%) | Hatching gland expression (%) | Caudal fin expression (%) | Non-specific expression (%) | No expression (%) |
| --- | --- | --- | --- | --- | --- |
| Age I-GFP (923) | 10.1 | 0.9 | 4.4 | 2.2 | 83.2 |
| EcoR I-GFP (635) | 9.0 | 0.6 | 0 | 0.1 | 90.3 |
| Bgl II-GFP (785) | 19.8 | 1.2 | 0 | 3.9 | 75.2 |
| Hind III-GFP (1094) | 13.8 | 1.5 | 0 | 7.2 | 77.5 |
| Exo III A-GFP (660) | 9.7 | 1.8 | 0 | 6.4 | 82.1 |
| Exo III B-GFP (796) | 6.6 | 1.1 | 0 | 1.1 | 91.3 |
| Exo III C-GFP (1043) | 2.4 | 3.1 | 5.0 | 8.4 | 81.0 |

Figure 6:
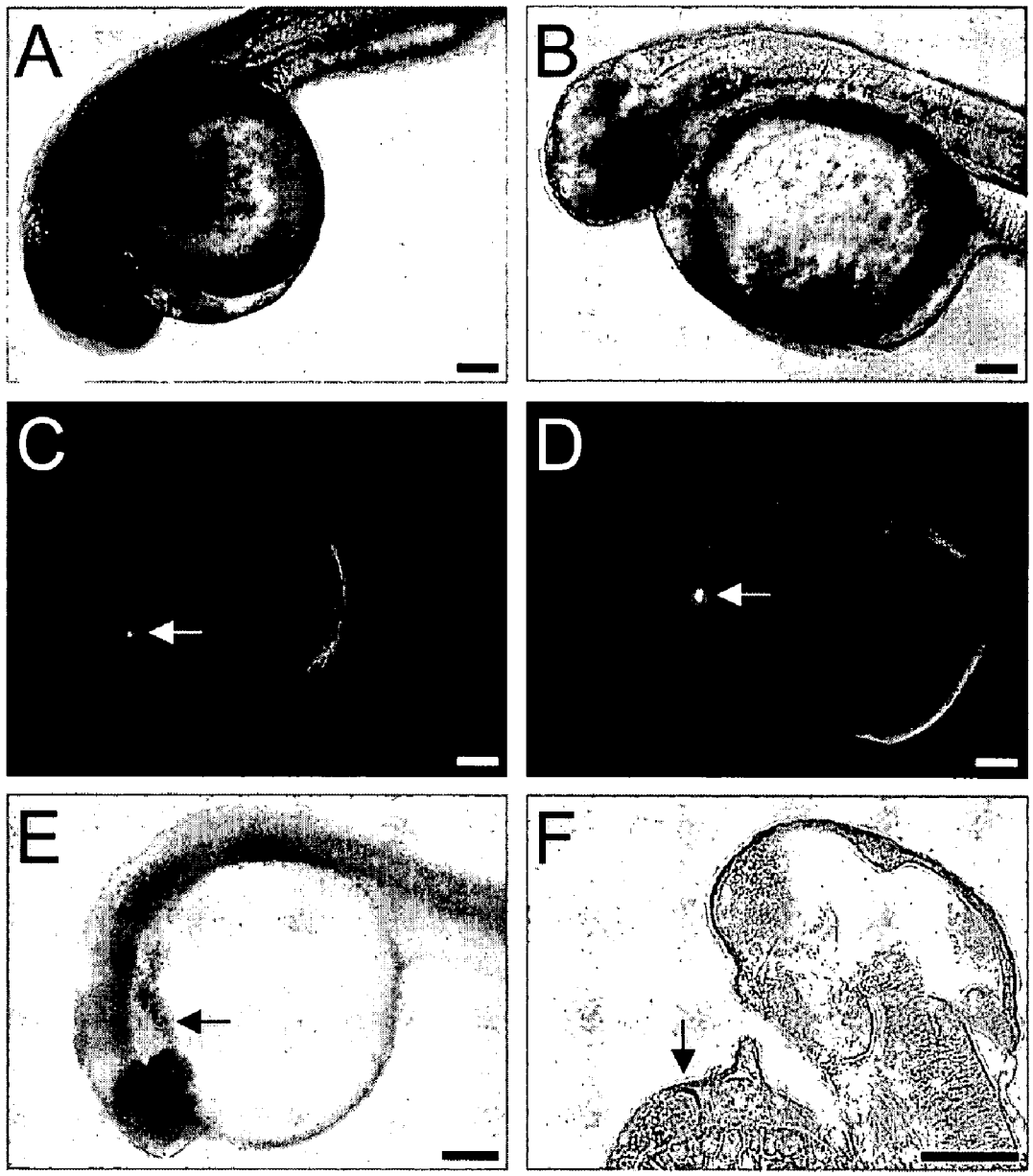
FIGS. 6A-6F demonstrate microscopic images for transient expression analysis of BMP4 promoter activity in zebrafish embryos injected with the Bgl II-GFP construct containing the 7.5-kb BMP4 promoter and regulatory DNA sequences.

Results of transient transgenic analyses and deletion analyses demonstrate the presence of negative and positive cis-acting regulatory DNA sequences and tissue-specific regulatory sequences. As shown in FIGS. 6-7 and Table 1, GFP expression directed by the 9 kb and 7.5 kb BMP4 promoter region in zebrafish embryos is observed mostly in the heart (about 10% to about 20% of the long-pec embryos tested), as well as in the skin and muscle, such as the hatching gland (about 0.6% to about 3.1% of the long-spec embryos tested) and caudal fin (about 4.4% to about 5.0% of the long-spec embryos tested). FIGS. 6A-6F demonstrate microscopic images of zebrafish embryos injected with the Bgl II-GFP construct containing the 7.5-kb BMP4 DNA sequences for transient expression analysis of BMP4 promoter activity and exhibit the tissue-specific expression pattern directed by this 7.5-kb BMP4 DNA sequences.

FIGS. 6A-6F demonstrate microscopic images for transient expression analysis of BMP4 promoter activity in zebrafish embryos injected with the Bgl II-GFP construct containing the 7.5-kb BMP4 promoter and regulatory DNA sequences. FIGS. 6A and 6B are the fluorescence microscopy images (in DIC mode) of lateral view of prim-8 and long-pec embryos, respectively. Prim-8 embryos are from an early developmental stage such as 26 hpf (hour post fertilization), whereas long-pec embryos are at 48 hpf stage and have been hatched out of corion. FIGS. 6C and 6D are the fluorescence microscopy images using FITC filter, showing GFP expression in the heart of prim-8 and long-pec embryos, respectively. The localized heart-specific expression, observed by the fluorescence of GFP protein, is also indicated by an arrow. FIGS. 6E and 6F are the microscopic images after immunohistochemistry and cryostat sectioning, showing GFP localization in the heart of prim-8 and long-pec embryos, respectively. Arrows indicate GFP localization in the heart. Scale bars represent 100 µm. The results demonstrate that the 7.5-kb BMP4 DNA sequences contain a BMP4 promoter and DNA sequences required for tissue-specific expression such as heart-specific expression during early developmental stage, such as in prim-8 embryos, as shown in FIGS. 6A, 6C, and 6E and in long-pec embryos, as shown in FIGS. 6B, 6D, and 6F. The results confirm constitutive tissue-specific expression sequences in the cloned 9 kb BMP4 promoter region (SEQ ID NO. 1). The results also suggest BMP4 expression in other cells or tissues is controlled by other regulatory regions located more distal to the transcription start site outside of this 9 kb BMP4 promoter and regulatory region. Alternatively, there may be a negative regulatory factor or factors in zebrafish embryos during embryo development to inhibit BMP4 expression directed by the 9 kb BMP4 promoter region in tissues other than heart, hatching gland, or caudal fin.

FIGS. 7A-7B demonstrate the percentage of GFP expression in a zebrafish embryos population for transient expression analysis of BMP4 promoter activity. The tissue-specific expression of GFP is analyzed in embryos injected with various recombinant GFP constructs containing different lengths of the BMP4 promoter and upstream regions. Long-pec embryos injected with respective constructs, Age I-GFP (9.0), EcoR I-GFP (8.3), Bgl II-GFP (7.5), Hind III-GFP (5.2), Exo III A-GFP (4.8), Exo III B-GFP (4.5), and Exo III C-GFP (2.7) are examined under a fluorescence microscope using an FITC filter. The results of various recombinant GFP deletion constructs are shown in FIG. 7A for heart-specific expression (solid circle) and in FIG. 7B for expression in other regions (solid square), such as skin and muscle of long-pec embryos. Also shown in gray bar in FIGS. 7A and 7B are GFP tissue-specific expression in long-pec embryos injected with a control construct containing CMV enhancer/promoter-GFP.

In FIG. 7, the highest level of GFP expression is observed in the 7.5 kb Bgl II-GFP expression construct, higher than the full-length 9 kb Age I-GFP construct. The results suggest a negative cis-acting regulatory sequence is located in the deleted DNA fragment from the 9 kb Age I-GFP construct to the 7.5 kb Bgl II-GFP construct, such as about 1.5 kb of the Age I-Bgl II genomic fragment or about 0.8 kb of the EcoR I-Bgl II fragment. However, co-injection experiments in FIG. 8 reveal no significant change in heart-specific expression percentage when the 1.5-kb Age I-Bgl II DNA fragment is added and compared to the 2.7-kb Exo III C-GFP expression construct. These results suggest that a negative effect is difficult to recover and/or the 1.5-kb Age I-Bgl II DNA fragment has to compete with a negative trans-acting transcription factor during co-injection analysis.

Figure 8:
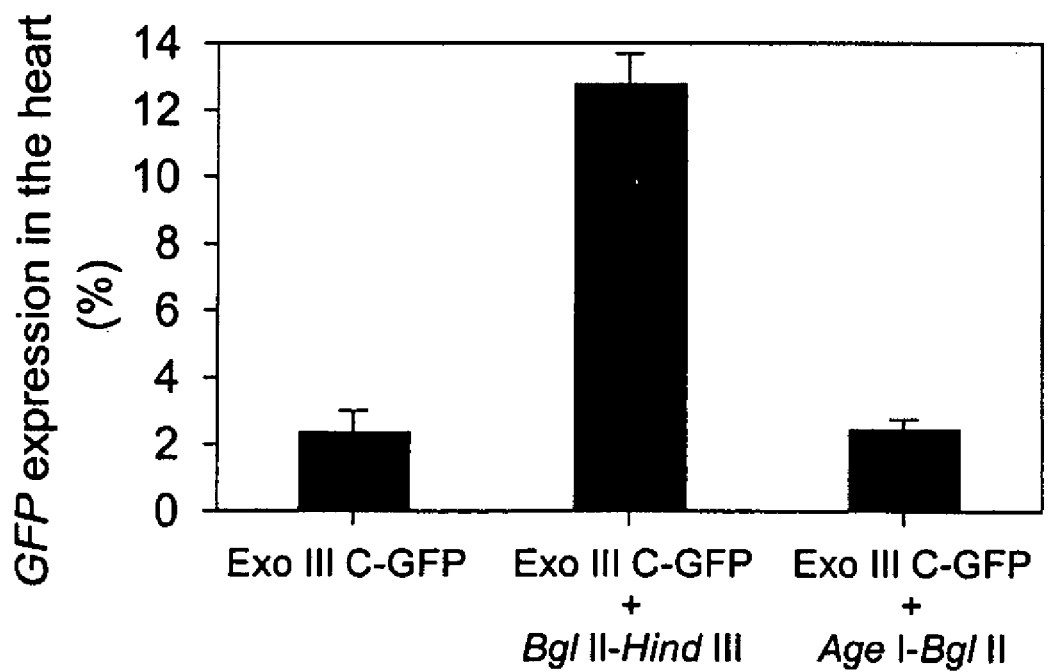
FIG. 8 demonstrates co-injection of different DNA fragments into zebrafish embryos to direct heart-specific expression in zebrafish. The percentages of GFP direct heart-specific expression are compared for long-pec embryos injected with different DNA constructs. The DNA constructs contain either Exo III C-GFP, which has minimum promoter activity, alone, together with a 2.4-kb Bgl II-Hind III DNA fragment, or with a 1.5-kb Age I-Bgl II DNA fragment. The results confirm a positive regulatory region within the 2.4-kb Bgl II-Hind III DNA fragment that controls heart-specific GFP expression.

FIG. 8 demonstrates co-injection of different DNA fragments into zebrafish embryos to direct heart-specific expression in zebrafish. The percentages of GFP direct heart-specific expression are compared in long-pec embryos injected with different DNA expression constructs. The DNA constructs contain either Exo III C-GFP, which has minimal promoter activity, alone, together with a 2.4-kb Bgl II-Hind III DNA fragment, or with a 1.5-kb Age I-Bgl II DNA fragment. The results confirm a positive regulatory region within the 2.4-kb Bgl II-Hind III DNA fragment that controls heart-specific GFP expression. In addition, reconstituting gene expression by ligating a promoter containing DNA fragment with other cis-acting regulatory DNA sequences or by co-transfecting (or co-injecting) a promoter containing DNA fragment and other cis-acting regulatory DNA sequences is also useful to study function and the promoter region and the cis-acting regulatory DNA sequences. For example, it was found that co-injecting the DNA sequences from intron 1 (SEQ ID No. 8) with either the 7.5 kb Bgl II or a 24 kb Asc I-Xho I (described in detail below) expression constructs into zebrafish 1 cell zygote further increases heart-specific GFP expression of the injected embryos by two-fold. The results suggest intron 1 of BMP4 gene includes an enhancer sequence. The existence of transcriptional enhancer sequences outside of the promoter, distal and proximal regulatory regions further indicate the complexity of the transcriptional regulatory mechanism in controlling zebrafish BMP4 gene expression during development and in different tissues.

Referring back to FIG. 7A, decreasing level of GFP expression is observed from Bgl II-GFP (7.5) to Exo III C-GFP (2.7) suggests a positive cis-acting regulatory sequence is located in the deleted DNA fragment from the 7.5 kb EcoR I-GFP construct to the 2.7 kb Exo III C-GFP (2.7), such as about 4.8 kb of the BglII-Exo III C genomic DNA fragment or about 2.4 kb of the Bgl II- Hind III fragment. In addition, co-injection experiments in FIG. 8 further confirm the existence of positive regulatory elements in the 2.4-kb Bgl II-Hind III DNA region. In FIG. 8, addition of the 2.4-kb Bgl II-Hind III DNA fragment increases heart-specific GFP expression of the injected embryos by 5.3-fold.

As another example, a genomic DNA fragment (Asc I-Xho 1) of about 24 kb containing the promoter region plus the proximal and distal regulatory DNA sequences in an expression vector (EGFP-ITR) is also obtained. This expression construct is isolated by ligating (reconstituting) a genomic DNA fragment containing about 19.5 kb of distal regulatory DNA sequences (SEQ ID No. 9) into the 9 kb AgeI-XhoI expression construct. Microinjection of this expression construct alone into zebrafish 1 cell zygote showed GFP expression in the heart (5-16%) and other regions (e.g., notochord, muscle, and skin (10-17%)). However, co-injecting this expression construct with a 6 kb intron 1 DNA fragment (SEQ ID No. 8) results in GFP expression in the heart (19-20%), hatching gland (19-37%), caudal fin (21-38%), and other organs.

V. Tissue-Specific Expression and Gene Expression during Embryonic Development

This invention provides a method for the isolation of transcriptional regulatory elements that contribute to the tissue-specific patterns of zebrafish genes, such as BMP4 genes. Tissue-specific gene expression includes but is not limited to gene expression observed solely or preferably in certain tissues, environmental situations and during certain stages of development. The invention further provides a method for isolation of transcriptional regulatory elements that contribute to tissue-specific gene expression in fish, such as heart-specific BMP4 expression in zebrafish as directed by the 9 kb Age I-Xho I promoter and proximal regulatory region. Transcriptional regulatory elements and expression vectors containing the transcriptional regulatory elements are disclosed. The transcriptional regulatory elements drive tissue-specific gene expression in transgenic zebrafish. The transcriptional regulatory elements are utilized to generate expression constructs using various expression vectors. The expression vectors contain a transcriptional regulatory region that includes a tissue-specific element isolated by the methods of this invention operably linked to a heterologous reporter gene that, upon expression of the protein product of the reporter gene, confers an assayable product for the expression of the transcriptional regulatory elements.

Figure 9:
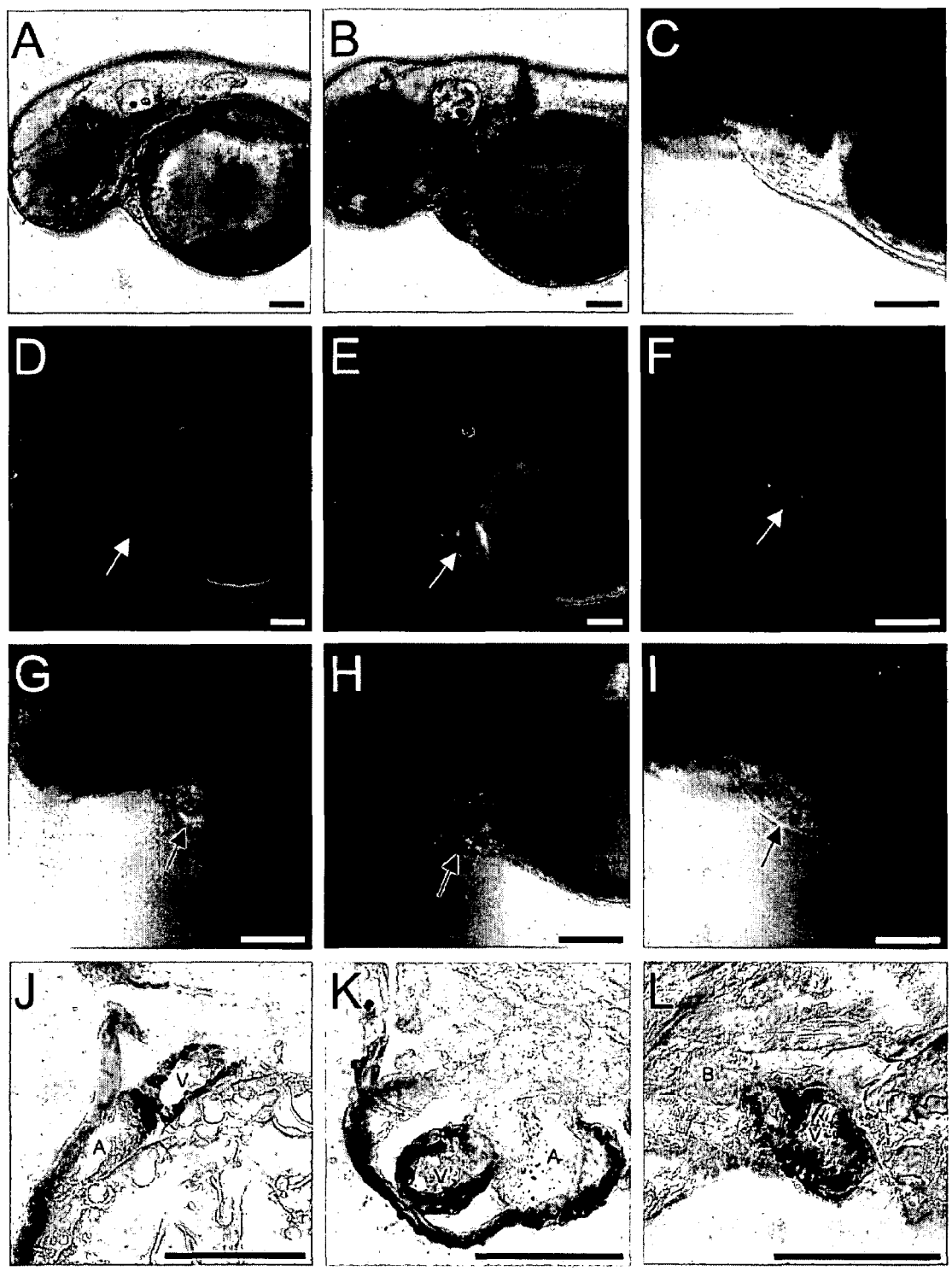
FIGS. 9A-9L demonstrate microscopic images of zebrafish transgenic F1 embryos for stable BMP4 promoter-GFP expression analysis. $F_1$ embryos from a transgenic $F_0$ line (B cell line) containing the Bgl II-GFP construct containing the 7.5-kb BMP4 promoter are used herein. The results confirm that the 7.5-kb BMP4 promoter direct stable heart-specific GFP expression and such stable and tissue-specific transgenic BMP4 expression is obtained from $F_0$ cell line to $F_1$ progeny during zebrafish development. F1 embryos during different stages of zebrafish development are examined. Long-pec F1 embryos are shown in FIGS. 9A, 9D, 9G, and 9J. Protruding-mouth F1 embryos are shown in FIGS. 9B, 9E, 9H, and 9K. 100 hour post fertilization (100-hpf) F1 embryos are shown in FIGS. 9C, 9F, 9I, and 9L.

For example, we have examined the activity of the bone morphogenetic protein 4 (BMP4) promoter in zebrafish embryos via transient and stable transgenic expression analyses in order to obtain a better understanding of the regulation of BMP4 tissue-specific expression. Stable transgenic lines are generally prepared to confirm tissue-specific expression of an identified promoter region, such as the heart-specificity of the 9.0 kb BMP4 promoter region in zebrafish. As an example, stable transgenic zebrafishes containing the 7.5-kb BMP4 promoter-GFP transgene are generated from $F_0$ adult fish of a transgenic embryo cell line containing the 7.5 kb BglII-GFP expression construct. The $F_1$ progeny from $F_0$ adult fish containing fluorescent hearts after crossing with wild type fish is analyzed during embryonic development of the $F_1$ progeny. The results are shown in FIG. 9 and Table 2, demonstrating that the 7.5-kb BMP4 promoter region and the proximal upstream regulatory region drive heart-specific GFP expression, specifically at the myocardium of the ventricles, which are observed in long-pec $F_1$ embryos, protruding-mouth $F_1$ embryos, and 100-hpf (hour post fertilization) transgenic $F_1$ embryos. Long pec embryos are at 48 hpf stage, protruding mouth embryos are at 72 hpf developmental stage, and 100 hpf embryos is at a later developmental stage (typically, embryos older than 72 hpf is at their larval stages). As shown in FIG. 9, GFP expression is localized in the myocardium of developing ventricles of all three types of $F_1$ embryos. In addition, trabeculation of the myocardium is readily observed in 100-hpf $F_1$ embryos.

TABLE 2

Inheritance of BMP4 promoter-GFP (BgI II-GFP construct) in transgenic zebrafish lines

| Transgenic $F_0$ line | $F_0$ sex | $F_1$ positive fish No. | % | GFP location |
|---|---|---|---|---|
| A | male | 238 | 11.3 | ventricle |
| B | male | 360 | 53.1 | ventricle |
| C | male | 195 | 4.1 | ventricle |
| D | male | 285 | 9.8 | ventricle & atrium |
| E | female | 59 | 22.0 | ventricle & atrium |
| F | female | 286 | 19.9 | ventricle & atrium |
| G | male | 158 | 22.8 | ventricle (weak) |
| H | male | 208 | 4.8 | ventricle & atrium |
| K | female | 208 | 15.4 | ventricle & atrium |
| L | female | 218 | 7.3 | ventricle & atrium | a No. in $F_1$ positive fish indicates total examined embryos

Together, these results indicate that the proximal 7.5-kb BMP4 promoter and regulatory DNA sequences contain transcriptional regulatory elements for heart-specific BMP4 expression, while tissue-specific regulatory elements for other endogenous BMP4-expressing tissues may reside in more-distal regions. Specifically, our results indicate that the 7.5-kb BMP4 promoter and its upstream proximal regulatory region contain both positive and negative regulatory elements that control heart-specific GFP expression in zebrafish embryos. In addition, this promoter can direct GFP expression in the myocardium of the ventricles of $F_1$ embryos from $F_0$ fish of a transgenic B line. However, it does not contain the complete regulatory region that modulates expression of the BMP4 gene in other organs, such as the eye, otic vesicle, hatching gland, pronephric duct, anus, pectoral, caudal fin, etc. One such example is the 19.5 kb distal regulatory region (SEQ ID No. 9), which contains DNA elements to direct BMP4 expression in eye, otic vesicle, hatching gland, anus, and caudal fin.

VI. Enhancer Sequences

The invention also provides enhancer sequences for BMP4 expression. For example, DNA sequences from the intron 1 of the zebrafish bone morphogenetic protein 4 (BMP4) gene suggest the presence of an enhancer sequence, as shown in SEQ ID No. 8. About 6 kb of the intron 1 was sequenced. Identification of an enhancer sequence is confirmed by co-injection of this 6 kb DNA segment with either 7.5 kb Bgl II or 24 kb Asc I-Xho I expression constructs into zebrafish 1 cell zygote. GFP expression in the heart is increased by two fold due to the presence of this intron 1-enhancer element. In addition, increased gene expression is also demonstrated in other tissues, such as eye, hatching gland, caudal fin, etc, when this intron 1-enhancer element is present.

VII. Use of Zebrafish BMP4 Gene, Promoter Regions, and Enhancer Sequences

Figure 4:
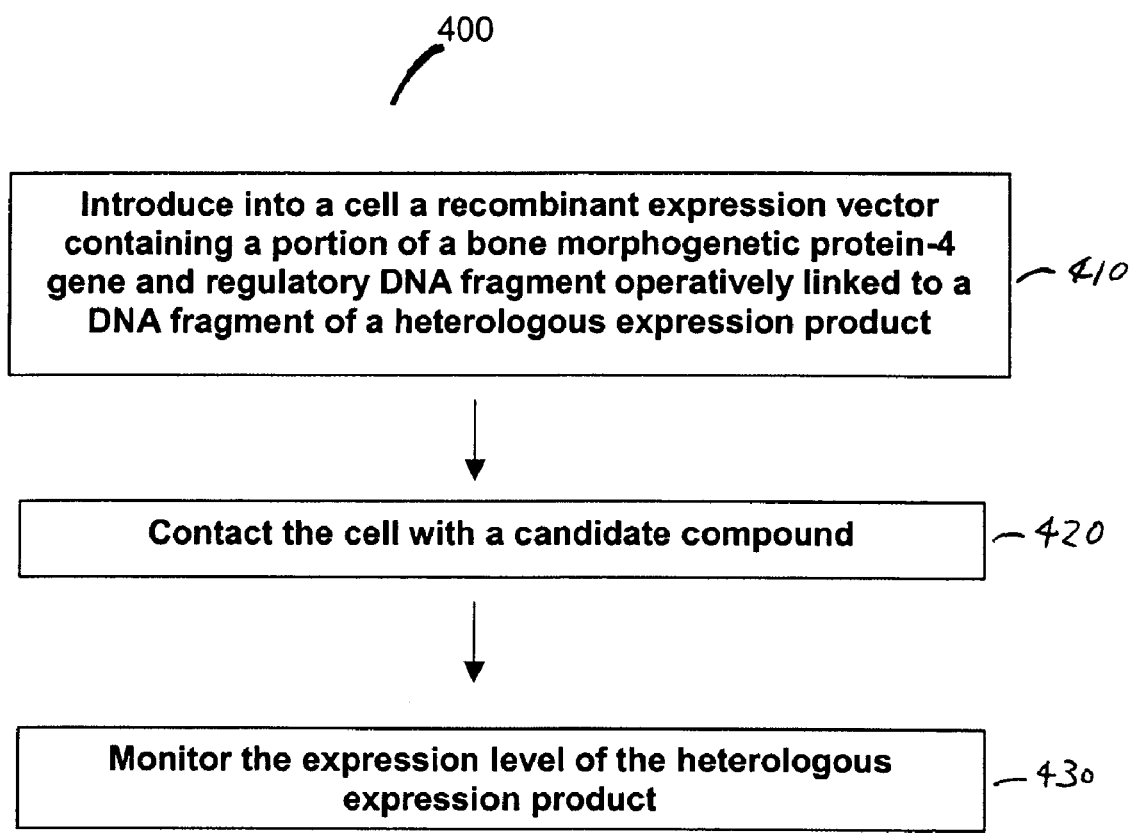
FIG. 4 is a flow diagram illustrating an exemplary method of identifying a potential agent.

In general, the identification of positive and negative cis-acting regulatory sequences, enhancer sequences, and tissue-specific regulatory elements are used in methods of the invention for screening an extracellular or intracellular potential agent, compound, stimulus, inhibitor, regulator, and/or any trans-acting factor that regulates BMP4 expression. In one aspect, FIG. 4 depicts a method 400 of identifying a potential agent, compound, stimulus, inhibitor, regulator, and/or trans-acting factor for BMP4 expression. At step 410, a recombinant expression vector containing DNA sequences for bone morphogenetic protein 4 (BMP4) gene, and one or more regulatory DNA fragments, such as promoter regions, proximal and distal regulatory regions, enhancer sequences, tissue-specific regulatory elements, and derivatives and fragments thereof is introduced into a cell. The recombinant expression vector also contains DNA sequences of a heterologous expression product, including, but not limited to, the luciferase gene, the Green Fluorescent Protein (GFP) gene, the chloramphenicol Acetyl Transferase gene (CAT), human growth hormone, alkaline phosphatase, β-glucuronidase, β-galactosidase, and any of the heterologous expression products whose expression can be assayed. DNA sequences for zebrafish bone morphogenetic protein 4 (BMP4) gene and promoter sequences include, but are not limited to, various introns and exons of the BMP4 gene, 5' flanking regions, positive and negative cis-acting regulatory sequences for BMP4 expression, enhancer sequences for BMP4 gene, any of the proximal and distal BMP4 regulatory regions, tissue-specific regulatory elements, cell-specific regulatory elements, and DNA fragments and derivatives thereof. For example, the BMP4 DNA sequences include any of the sequences described herein, including, but not limited to, SEQ ID No. 1, SEQ ID No. 2, SEQ ID No. 4, SEQ ID No. 7, SEQ ID No. 8, and SEQ ID No. 9, etc. The recombinant expression vector containing BMP4 DNA sequences can be introduced into the cell through any of the techniques for delivering DNA fragments inside a cell, including, but not limited to, microinjection, eletroporation, transfection, transformation, and others. The cell recipient includes any of the cell types, cell lines, or embryos and may preferably be at various stages during development for comparison.

At step 420, the cell is contacted with a candidate compound, generally through a screening method from a panel of suitable compounds, agents, substances, screening library, or a construct containing any of the suitable potential agents, compounds, regulators, stimuli, inhibitors, and any trans-acting factors. At step 430, the expression level of the heterologous expression product is monitored. For example, an altered expression level in the presence of the candidate compound indicates the candidate compound as the potential agent, compound, stimulus, inhibitor, regulator, and/or trans-acting factor for BMP4 expression. Such an altered expression level can be an increased or decreased level of BMP4 expression.

As an example, a method for identifying a potential agent for zebrafish tissue-specific expression includes introducing into a cell a tissue-specific expression sequence operatively linked to a nucleotide sequence for a heterologous expression product. Suitable tissue-specific expression sequence includes, but is not limited to, the 9.0 kb proximal BMP4 promoter region, the 19.5 kb distal regulatory region, various genomic DNA fragments containing BMP4 gene, and portions or derivatives thereof, for example, SEQ ID No. 1, SEQ ID No. 4, SEQ ID No. 7, SEQ ID No. 8, and SEQ ID No. 9, etc.

Figure 5:
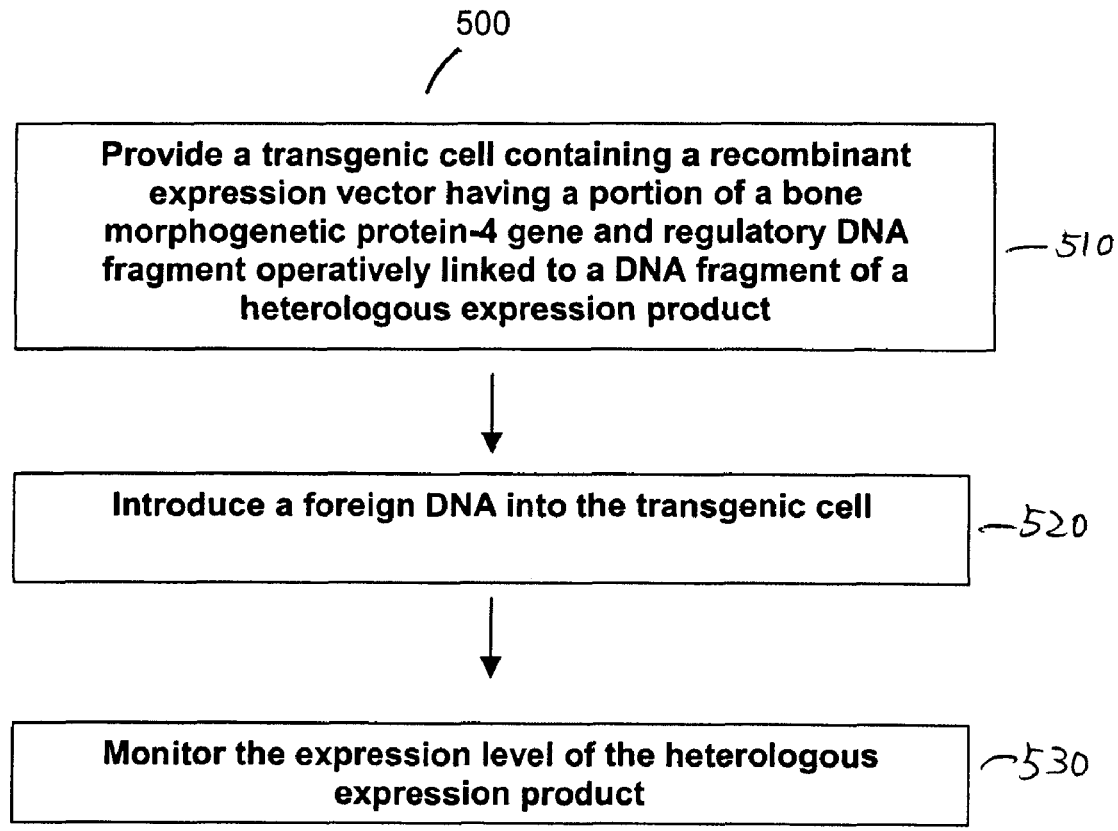
FIG. 5 is a flow diagram illustrating an exemplary method of screening a compound that regulates BMP4 gene expression.

In another aspect, FIG. 5 depicts a method 500 of screening an effecter that regulates bone morphogenetic protein-4 expression. At step 510, a transgenic cell having a portion of a bone morphogenetic protein-4 regulatory DNA fragment operatively linked to a heterologous expression product is constructed. The transgenic fish can be the transient transfected cells and embryos, and cells from transient $F_0$ adults expressing the heterologous expression product, and preferably cells from stable transgenic $F_1$ embryos and adults expressing the heterologous expression product. The regulatory DNA fragment can be any of the 5' flanking regions, enhancer sequences, promoter regions, genomic DNA or cDNA of the BMP4 gene, and derivatives thereof, for example, SEQ ID No. 1, SEQ ID No. 4, SEQ ID No. 7, SEQ ID No. 8, and SEQ ID No. 9, etc.

At step 520, a foreign DNA is introduced into the transgenic cell of the invention. For example, the foreign DNA can be a DNA fragment screened from a cDNA library, genomic DNA library, and any DNA construct containing suitable potential agents, compounds, stimuli, inhibitors, regulators, and trans-acting factors. At step, 530, the expression level of the heterologous expression product for a number of the transgenic cell containing the foreign DNA is monitored. An altered expression level in the presence of the foreign DNA as compared to the absence of the foreign DNA indicates the foreign DNA encodes the effecter.

Recently, several mutations that disrupt cardiac chamber formation have been identified in zebrafish. While, our BMP4 promoter transgenic lines would allow in vivo imaging of cardiac morphogenesis during various stages of heart development, in addition, mutagenesis analyses on these transgenic embryos would identity additional genes that may regulate BMP4 function in cardiac development.

In addition, a method for identifying an expression pattern of a zebrafish BMP4 expression sequence is provided. The method includes providing a zebrafish BMP4 expression sequence which is operatively linked to a nucleotide sequence of a heterologous expression product, introducing into a cell the zebrafish DNA expression sequence, and monitoring the expression level of the heterologous expression product. As a result, the expression pattern for the expression of BMP4 gene by the expression sequence is identified at various stages during embryonic development, during morphogenesis, during organogenesis of a specific organ, or during formation of a specific tissue. For example, GFP expression directed by the 7.5 kb Bgl II-Xho I DNA fragment is useful for in vivo imaging of BMP4 expression pattern during zebrafish heart development and cardiac morphogenesis, such as cardiac chamber formation as described in FIG. 9.

The expression pattern of zebrafish BMP4 expression can also be analyzed by other methods. For example, we have performed whole-mount in situ hybridization to analyze endogenous gene expression at mRNA level using DNA probe prepared from the BMP4 DNA of the invention.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g., amounts, temperature, concentrations, etc.) but some experimental errors and deviations should be allowed for. Unless otherwise indicated, parts are parts by weight, molecular weight is average molecular weight, temperature is in degrees centigrade, and pressure is at or near atmospheric.

EXAMPLE 1

Fish Maintenance

Adult zebrafish (*Danio rerio*) were raised at the zebrafish facility in the Institute of Zoology, Academia Sinica. The fishes were maintained in 20 liter aquariums supplied with filtered fresh water and aeration under a photoperiod of 14 hour light and 10 hour dark as described in The Zebrafish Book (Westerfield, 1995).

Cleavage-stage embryos represented a mixture of embryos between 2-cell and 16-cell. Blastula-stage embryos represented a mixture of embryos at 512-cell or higher stage. Gastrula-stage embryos represented a mixture of embryos between shield and 75% epiboly. Segmentation-stage embryos represented a mixture of embryos between 14-somite and 20-somite. Pharyngula-stage embryos represented a mixture of embryos between prim-5 and prim-25.

EXAMPLE 2

Total RNA Isolation

Total RNA from embryos at different developmental stages was isolated using guanidinium thiocyanate-phenol-chloroform extraction method. Total RNA from different adult organs and tissues was extracted using RNAzol B following the protocol from manufacturer (Tel-Test, Inc.). For the RT-PCR reaction, total RNA was first digested with RNase-free DNase 1 (150 units in a 200-μl reaction volume) in 40 mM Tris-HCl pH 7.5, 6 mM MgCl2, 10 mM NaCl at 37° C. for about 30 min, followed by phenol-chloroform extraction. DNA and RNA concentrations were determined spectrophotometrically (Hitachi U2000).

EXAMPLE 3

RT-PCR

PCR reactions (100 μl) were performed using a mixture containing 10 μg of genomic DNA, 100 pmole primers, 5 mM MgCl2, 0.2, mM dNTP, and 2.5 units of Replitherm DNA polymerase (Eicentre). PCR cycles were set as follows: 1 min at 94° C., 1 min at 50° C., 1 min at 72° C. for 35 cycles, 10 min at 72° C. for 1 cycle and the resulting product was stored at 4° C. DNase-I treated total RNA from embryos at different developmental stages (3 μg) or from different adult organs and tissues (0.5 μg) and components from GeneAmp RNA PCR kit (Perkin Elmer) were used to generate the first-strand cDNA. Twenty microliters of cDNA products were then used in a PCR reaction as described above with a pair of two BMP4-specific primers. The two BMP4-specific primers are: 5'-TGGTCACATTCGGACATGACGGCA-3' and 5'-AGA/GTCTCCGTTTACCGGCAGCCA-3'. PCR conditions were set as follows: 1 min at 94° C. for 1 cycle, 1 min at 94° C., 1 min at 64° C., 1 min at 72° C. for 35 cycles, 10 min at 72° C. for 1 cycle, and the resulting product was stored at 4° C. The control RT-PCR reaction involved α-actin specific primers, which are 5'TCACACCTTCTACAACGAGCTGCG-3' and 5'-GAAGCTGTAGCCTCTCT-CGGTCAG-3' for synthesizing α-actin control transcript.

EXAMPLE 4

Zebrafish Genomic DNA Library Screening

To generate a probe for screening a genomic DNA library, a pair of degenerate oligonucleotides was designed according to conserved regions obtained from amino acid sequence alignment among various mammalian BMP4 genes. The two degenerate primers are 5'-GAT/C TTT/C T/AC/GI GAT/C GTI GGI TGG AA-3' and 5'-CA ICC T/CTC IAC CAT T/CTC T/CTG-3'. Sequence analysis of a 270-bp PCR product obtained using the two conserved degenerate oligonucleotides as primers revealed that its deducted amino acid (corresponding to amino acids 308-396 of the isolated zebrafish BMP4 gene) shared 89% sequence identity with the amino acid sequence of human BMP4. The 270-bp PCR clone containing the BMP4 carboxyl-terminal domain was also used to generate DIG-labeled DNA probe following the manufacturer's protocols (Boehringer Mannheim) and to screen for zebrafish BMP4 gene. In order to obtain zebrafish BMP4 gene and DNA fragments containing the BMP4 promoter and its regulatory regions, a lambda FIX II zebrafish genomic DNA library (kindly provided by Dr. C. Y. Chang from the Institute of Zoology, Academia Sinica) was screened using several fragments of DIG-labeled DNA located in the 5'-untranslated region (UTR) region as probes and according to standard protocols in Sambrook, J. et al. (1989) Molecular Cloning, A Laboratory Manual, Cold Spring Harbor Press, Plainview, N.Y. Lambda DNA purification was conducted as described in Donovan et al. (1993). Accordingly, the zebrafish genomic DNA library was screened using the 270-bp PCR product as a probe and several positive clones were obtained after screening more than $1.4 \times 10^7$ phage colonies. The average size of the isolated DNA fragment was around 14.9 kb. Positive genomic clones were isolated and the inserted DNA fragments were digested with Not I. These genomic fragments were subcloned into a pBluscript II vector and sequences. DNA sequencing was performed using a BigDye terminator cycle sequencing ready reaction kit on an ABI Prism 377 automatic DNA sequencer (Applied Biosystems).

In addition, 5'-RACE (5'- rapid amplification of cDNA ends, Clontech) was conducted in order to verify the transcription start site. Typically, poly(A)+ mRNA or total RNA isolated from embryos were used as templates. Random hexamer or gene specific oligonucleotide (SP1 primer supplied in the kit) was used as primers for a reverse transcription (RT) reaction to generate RNA-cDNA hybrid product. Terminal transferase was then used to add several dATP to the 3'end of $1^{st}$-strand cDNA. First PCR amplification was then conducted using gene specific oligonucleotide (SP2 primer used) and oligo (dT)-anchor primer as a primer pair and the RNA-cDNA hybrid product as template in a first PCR reaction. Nested PCR can be performed using PCR product from the first PCR reaction as template and gene specific oligonucleotide (SP3) and anchor primer as a primer pair in a second nested PCR reaction. The final PCR product from the second nested PCR reaction or even from the first PCR reaction can be cloned into pGEMT vector (Roche) for sequencing and identification of the transcription start site.

EXAMPLE 5

Northern Blot Analysis

About 25 μg of total RNA was ethanol precipitated and loaded on 1.2% agarose gels containing 1.2 M formaldehyde and EB buffer. Gels were transferred to nylon membranes for 4 hour using a downward alkaline transfer method. Membranes were prehybridized for 2 hour in 5× SSC, 50% formamide, 2% blocking solution, 0.1% sodium lauryl sarcosine, and 0.02% NaDodSO4 for 5 min twice at room temperature followed by 0.1× SSC, 0.1% NaDodSO4 wash for 15 min twice at 65° C. CSPD chemiluminescent detection was conducted following protocols from the manufacturer (Boehringer Mannheim), except that 1× phosphate-buffered saline (PBS; 137 mMNaCl, 2.7 mM KCl, 10.1 mM Na2HPO4, 1.8 mM KH2PO4) containing 5% nonfat milk and 0.3% Tween-20 was used in place of blocking solution.

EXAMPLE 6

Southern Blot Analysis

About 10 microliters of RT-PCR products were loaded on 1.5% 0.5× TBE agarose gels and denatured, neutralized, and transferred according to standard methods (Sambrook et al., 1989). Membranes were hybridized in the same pre-hybridization buffer that was used for Northern blot containing 25 ng/ml of 270 bp DIG-labeled DNA probes at 42° C. overnight. After hybridization, membranes were washed with 2× SSC, 0.1% NaDodSO4 for 5 min twice at room temperature followed by 1× SSC, 0.1% NaDodSO4 washed for 15 min twice at 55° C. AMPPD chemiluminescent detection was carried out following instruction from the manufacturer (Boehringer Mannheim) and the same buffer used in the Northern procedure.

EXAMPLE 7

Generation of Fusion Protein and Production of Polyclonal Antibodies

A 1.5-kb Xba I-Eco RI subclone containing most of BMP4 coding region and 3' noncoding region was used to generate in vitro-transcribed DIG-labeled antisense RNA. To prepare zebrafish BMP4 fusion protein, a 270-bp Bam HI-Hind III restriction fragment containing the BMP4 carboxyl-terminal region was inserted into BAM HI and Hind III-digested pQE-30 vector. This fragment encoded amino acids 308-396 of zebrafish BMP4 protein. Purification of His-tagged BMP4 fusion protein was conducted according to protocols of the manufacturer (Qiagen).

Polyclonal antibodies were raised against the purified fusion protein according to standard methods (Harlow and Lane, 1988). Crude antisera were affinity purified using the Olmstead-style strip purification method. To evaluate the specificity of anti-BMP4 antisera, an overnight culture of *Escherichia coli* cells transformed with pQE30 containing the 270-bp BamH I-Hind III fragment of BMP4 gene was diluted 1:10 in fresh LB medium and induced with IPTG following protocols from the manufacturer (Qiagen). *Escherichia coli* total protein were separated by 15% SDS-PAGE and transferred onto nitrocellulose membranes as described in the Western Blot Analysis section, except that 5% nonfat milk in PBST (1× PBS and 0.1% Tween-20) was used as the blocking buffer and a colorimetric detection method involving nitro blue tetrazolium (NBT) and 5-bromo-4-cholro-3-indolyl phosphate (BCIP) was used for visualizing the purified fusion protein from *E. coli* total lysate.

The specificity of anti-BMP4 antisera was further tested against human recombinant proteins. Both human TGF-β1 (GIBCO BRL Life Technologies, Inc.) and BMP2 recombinant proteins (0.3 μg) together with cholate extractable total protein (19 μg) isolated from 11-day-old zebrafish hatching larvae were separated by 10% NaDodSO4-PAGE and Western Blotting was performed.

EXAMPLE 8

Western Blot Analysis

Embryos from various developmental stages were harvested by centrifugation and subjected to homogenization in buffer containing 2% cholic acid, 10 mM Tris-HCl pH 8.0 at 4° C., 10 μl/ml PIC 1 (protease inhibitor cocktail: 1 mg/ml leupeptin, 2 mg/ml antipain, and 10 mg/ml benzamidine dissolved in aprotinin), and 1 mM phenylmethylsulfonyl fluoride (PMSF). Extracts were centrifuged and the supernatants used for Western blot analysis. The protein concentration was measured by Pierce BCA method. Samples of cholate-extractable total protein (25 μg) were separated by 10% SDS-PAGE and electrophoretically transferred to nitrocellulose membranes using a transfer buffer containing 25 mM Tris pH 8.8, 192 mM glycine, and 20% methanol. The nitrocellulose membrane blots were blocked in a blocking buffer containing 5% BSA in PBST at 4° C. overnight.

The blots were incubated with affinity-purified anti-BMP4 antisera, pre-diluted 1:10,000, at room temperature for about one hour. After several washes in the blocking buffer, the blots were incubated with horseradish peroxidase-conjugated goat anti-rabbit IgG secondary antibody (Jackson Immuno Res. Lab., Inc.), pre-diluted 1:10,000) at room temperature for about one hour. After several washes in the blocking buffer and a 15 min wash in PBST containing 0.5 M NaCl, the blots were developed by an enhanced chemiluminescence method following protocols from the manufacturer (ECL method, Amersham) to reveal the presence of protein-antibody complexes.

EXAMPLE 9

DNA Expression Constructs

A 9 kb Age I-Xho I genomic BMP4 DNA fragment was cloned into a modified EGFP-ITR expression vector containing a GFP gene that was flanked by inverted terminal repeats (ITRs) from an adeno-associated virus (AAV, Hsiao et al., 2001). The EGFP-ITR vector (Hsiao et al., 2001) was changed again to incorporate additional restriction enzyme sites by ligating it with annealed complementary oligonucleotides. For example, an Age I-GFP construct was generated by ligation of the 9-kb Age I-Xho I DNA fragment into the modified EGFP-ITR vector digested with Age I and Sal I. Similarly, EcoR I-GFP, Bgl II-GFP, and Hind III-GFP expression constructs were subcloned by ligation of a 8.3-kb EcoR I-Xho I, a 7.5-kb Bgl II-Xho I, and a 5.2-kb Hind III-Xho I DNA fragment into the modified EGFP-ITR vector digested with Sal I and respective restriction enzymes. Exo III deletion was generated using the Erase-a-Base system (Promega). DNA sequencing was conducted to confirm the DNA sequences at the 5' end of various constructs. After restriction enzyme digestion, exo III nuclease deletion, ligation, transformation and confirmation by sequencing, several BMP4 promoter-GFP recombinant expression constructs with different 5'-end BMP4 DNA fragments to direct the expression of the GFP gene were generated. These deletion expression constructs containing different lengths of BMP4 DNA fragments subcloned into the EGFP-ITR expression vector are shown in FIG. 3, illustrating the respective restriction sites on both ends and their lengths.

FIG. 3 illustrates total of 7 DNA expression constructs containing the heterologous reporter gene obtained. These expression constructs include Age I-GFP (9.0), EcoR I-GFP (8.3), Bgl II-GFP (7.5), Hind III-GFP (5.2), Exo III A-GFP (4.8), Exo IIIB-GFP (4.5), and Exo IIIC-GFP (2.7) with the length of the corresponding BMP4 DNA fragments in parenthesis. In addition, a control expression construct containing CMV promoter/enhancer cloned into the GFP expression vector is also obtained. The resultant gene constructs were respectively linearized and microinjected into zebrafish 1-cell zygotes for transient expression analyses and generating stable transgenic fish cell lines.

EXAMPLE 10

Microinjection in Zebrafish Embryos

Various constructs with different 5' ends were linearized at the Sca I site located in the ampicillin-resistant gene of the EGFP-ITR vector. The control vector, CMV-EGFP-ITR, was linearized at the Not I site. Linearized DNA was purified by phenol-chloroform extraction and ethanol precipitation. The DNA pellet was dissolved in water, and approximately 4.6 nanoliters of solution containing about 6.2 fmoles of DNA was microinjected into the cytoplasm of zebrafish embryos at the 1-cell or 2-cell stage. A trace amount of phenol red was also added to aid injection. Microinjection was performed using a Nanoject II automatic injector (Drummond).

EXAMPLE 11

Evaluation of Various BMP4 Promoter-GFP Constructs via Transient Expression Analysis An example of transient expression analysis using the Bgl II-GFP (7.5) expression construct is shown in FIGS. 6 and 7 and in Table 1. Heart-specific GFP expression was observed in the injected prim-8 embryos (FIGS. 6A and 6C) and long-pec embryos (FIGS. 6B and 6D). In addition, immunohistochemistry was performed on prism-5 and long-pec embryos from the transient transgenic analysis to further confirm heart-specific GFP expression directed by the Bgl II-GFP (7.5) expression construct using an anti-GFP antibody following cryostat sectioning, as shown in FIGS. 6E and 6F. In general, approximately 10% of the injected embryos exhibit GFP expression in the heart. For example, FIG. 7A demonstrate about 10% of the zebrafish population exhibiting GFP expression in the heart when injected with either the 9.0-kb Age I-GFP expression construct or the 8.3-kb Eco RI-GFP expression construct.

Interestingly, about a two-fold increase in the percentage of the injected embryos exhibiting heart-specific GFP expression was observed when injected with the 7.5-kb Bgl II-GFP expression construct as compared to other expression constructs. In FIG. 7A, the 7.5-kb Bgl II-GFP expression construct has obtained about 20% of heart-specific GFP expression, which is 4.4-fold higher than the CMV control expression construct. The CMV promoter/enhancer-GFP control expression construct exhibits about 4.5% of heart-specific GFP expression, which represents a random probability of promoter directed GFP expression in the heart.

Conversely, a decreased percentage of about 14% of the injected embryos exhibiting heart-specific GFP expression was observed when injected with the 5.2-kb Hind III-GFP expression construct as compared to the 7.5-kb Bgl II-GFP expression constructs. This result in FIG. 7A suggests that a negative and a positive cis-acting regulatory DNA element are located in the 0.8-kb Eco RI-Bgl II and the 2.4-kb Bgl II-Hind III regions.

Overall, the results in FIG. 7A demonstrated a decreasing percentage of the injected embryos exhibiting heart-specific GFP expression. When the 4.8-kb Exo III A-GFP, the 4.5-kb Exo III B-GFP, and the 2.7-kb Exo III C-GFP expression constructs were respectively injected, about 9.7%, about 6.6%, and about 2.4% of the injected embryos exhibit heart-specific GFP expression. The results are also summarized in Table 1.

GFP expression in other tissues directed by the 9.0-kb Age I-Xho I BMP4 promoter was also examined. As shown in FIG. 7B and in Table 1, low levels of GFP expression of the injected long-pec embryos were observed in skin and muscle. The highest nonspecific GFP expression of about 8.4% in skin or muscle was observed when injecting the 2.7-kb Exo III C-GFP expression construct. Overall, BMP4 directed GFP expression exhibit a much lower expression percentage in the embryo population examined, as compared to the CMV promoter/enhancer-GFP control expression construct. The control shows approximately 88.1% of the injected embryos express GFP in regions such as skin and muscle, as shown as non-specific expression in Table 1.

In addition, low percentages of BMP4 directed GFP expression in the hatching gland of the injected long-pec embryos were observed. The results range from about 0.9% to about 3.1% of BMP4 directed GFP expression in the hatching gland and from about 0% to about 5% of BMP4 directed GFP expression in caudal fin for different expression constructs, as shown in Table 1. In general, the majority of the injected embryos exhibit no GFP expression, ranging from about 75% to about 91% of the embryo population. This is partly due to the mosaicism of transgene distribution and partly due to the presence of the ITR sequence in the vector that enhances tissue-specific expression and thus inhibits nonspecific expression (Fu et al., 1998; Ju et al., 1999; Hsaio et al., 2001).

EXAMPLE 12

Co-injection Transient Expression Analysis of Various BMP4 Promoter-GFP Constructs To further confirm the presence of a negative and a positive regulatory DNA element in the 0.8-kb Eco RI-Bgl II and the 2.4-kb Bgl II-Hind III DNA fragments and clarify heart-specific expression directed by these two regulatory elements, co-injection experiments were performed. Two DNA fragments, a 2.4-kb Bgl II-Hind III DNA fragment and a 1.5-kb Age I-Bgl II DNA fragment containing the 0.8-kb Eco RI-Bgl II region were individually co-injected in equal molar ratio with the 2.7-kb Exo III C-GFP expression construct which contains minimal promoter activity into zebrafish embryos. The results of the co-injection experiments are shown in FIG. 8.

FIG. 8 show that the addition of the 2.4-kb Bgl II-Hind III DNA fragment increase heart-specific GFP expression of the injected embryos by 5.3-fold as compared to the Exo IIIC-GFP (2.7) expression construct. For example, when the Exo III C-GFP (2.7) construct exhibiting minimal promoter activity is co-injected with the 2.4-kb Bgl II-Hind III DNA fragment, about 5.3 fold increase in heart-specific GFP expression is observed; in contrast, heart-specific GFP expression remains the same for embryos injected with the Exo IIIC-GFP construct alone or co-injected with the 1.5-kb Age I-Bgl II DNA fragment. The addition of the 1.5-kb Age I-Bgl II DNA fragment showed no significant change in heart-specific expression percentage when compared to the Exo IIIC-GFP (2.7) expression construct. These results confirm that the 2.4-kb Bgl II-Hind III DNA region contains regulatory elements required for heart-specific GFP expression.

EXAMPLE 13

Zebrafish BMP4 Promoter and Adjacent Upstream Region Contain a Heart-Specific Regulatory DNA Element Results of transient expression analyses in FIG. 7 using various expression constructs containing different lengths of the BMP4 promoter and proximal regulatory DNA sequences demonstrate that the 0.8-kb Eco RI-Bgl II DNA fragment contains negative cis-acting regulatory DNA elements which inhibit heart-specific expression, while the 2.4-kb Bgl II-Hind III DNA fragment contains positive cis-acting regulatory DNA elements which enhance GFP expression in the heart. In addition, the co-injection experiment in FIG. 8 confirms the presence of a positive heart-specific regulatory element in the 2.4-kb Bgl II-Hind III DNA region. However, the fact that we did not observe the inhibitory effect of the 1.5-kb Age I-Bgl II DNA fragment in the co-transfection experiments may be due to the low expression level of Exo IIIC-GFP (2.7) construct containing the minimal promoter itself and/or a significant decrease in expression level was hard to achieve in this case. Studies have shown that microinjected DNA fragments will undergo concatemerization into high molecular weight DNA complexes, which are then amplified in injected Xenopus and zebrafish embryos. The resultant high molecular weight DNA complexes position the regulatory element in close proximity to the promoter that enhances or inhibits expression of the reporter gene.

Previously, for mouse BMP4 gene, the chicken ovalbumin upstream-transcription factor (COUP-TFI) has been shown to inhibit BMP4 promoter activity. Transcription factor motif analysis of the zebrafish BMP4 promoter and its upstream regulatory regions does not reveal the presence of a COUP-TFI binding site in the 1.5-kb Age I-Bgl II DNA fragment. However, binding sites for transcription factors, such as CdxA, SRY, Nkx2.5, and AML-1a, are present in the 2.4-kb Bgl II-Hind III region. The present invention provides methods for screening a potential agent, compound, and/or molecular regulator (e.g., transcription factor, activator, repressor, etc.) which can interact with BMP4 promoter and requlatory DNA sequences and/or direct tissue-specific expression, such as BMP4 gene in the heart, eyes, otic vesicles, hatching gland, anus, caudal fin, and other tissues.

EXAMPLE 14

Different Zebrafish BMP4 Promoter Regions Directing Tissue-Specific BMP4 Gene Expression We have identified the presence of a heart-specific regulatory element in the 9 kb BMP4 promoter and 5'-upstream region, as well as other tissue-specific elements in a distal zebrafish BMP4 regulatory region. A 19.5 kb zebrafish BMP4 regulatory region located distal to the 9 kb Age I-Xho I 5'-upstream region was identified and obtained from genomic DNA screening. The 19.5 kb distal zebrafish BMP4 regulatory region contain DNA fragments required to direct BMP4 gene expression in tissues other than heart, such as eyes, otic vesicles, hatching gland, anus, and caudal fin, as tested in long-pec embryos.

In addition, we have obtained results from whole-mount in situ hybridization which demonstrate that BMP4 mRNA is expressed in a variety of tissues, such as eyes, otic vesicles, heart, pronephric ducts, hatching gland, anus, and pectoral and caudal fin buds at least in prim-5 (24 hpf) embryos. However, the 9 kb Age I expression construct only directed GFP expression in the heart. Thus, the regulation of tissue-specific expression of the BMP4 gene is complex and we contemplate using cloned genomic BMP4 DNA fragments (e.g., SEQ ID No. 1, SEQ ID No. 4, SEQ ID No. 7, SEQ ID No. 8, SEQ ID No. 9, etc.) to perform detailed comparison of more deletion constructs and co-injection analysis, to delineate the complex mechanism regulating BMP4 gene expression, and to identify other factors, compounds, and DNA sequences involved in BMP4 gene expression.

EXAMPLE 15

Production and Inheritance of BMP4 promoter-GFP Transgenic Zebrafish

We raised long-pec embryos, having injected 7.5 kb Bgl II-GFP construct to direct heart-specific GFP expression, to sexual maturity. Crosses between $F_0$ adults and wild type fish of different sex were performed in order to obtain stable transgenic fish cell lines. The identification of transgenic progeny was conducted by examining GFP expression using fluorescence microscopy equipped with a FITC filter (Zeiss, Axioplan 2).

The results are summarized in Table 2. Out of 56 $F_0$ adult fish, 25% (14) of them were found to have transmitted the transgene to the $F_1$ generation. About 10 stable transgenic fish lines were further examined, designated as $F_0$ transgenic fish A-L. The 10 transgenic $F_0$ lines listed in Table 2 comprise 6 male and 4 female adult fishes. The results further confirm that heart-specific GFP expression directed by the 7.5 kb Bgl II-Xho I DNA fragment are inherited from $F_0$ transgenic lines to $F_1$ embryos. As shown in Table 2, transmission rates of the Bgl II-Xho I directed heart-specific GFP expression from $F_0$ transgenic lines to $F_1$ embryos range from about 4.1% to about 53% among different transgenic lines.

EXAMPLE 16

Immunohistochemistry and Cryostat Sectioning

Immunohistochemistry was performed based on Park et al. (2000) with some modifications. In general, long-pec $F_1$ embryos, protruding-mouth $F_1$ embryos, and 100 hour-post-fertilization (hpf) $F_1$ embryos from the transgenic B cell line ($F_0$) were fixed in a buffer containing 4% paraformaldehyde in PBS at about 4° C. overnight. After two rinses with about 1 ml of PBST buffer (1× PBS, 0.1% TritonX-100), embryos were treated with acetone (prechilled at about –20° C.) for 7 min and washed with PBST three times. For 100-hpf $F_1$ embryos, additional steps were performed in order to make the 100-hpf $F_1$ embryos more permeable. For example, treatment with about 100 μg/ml of proteinase K for 30 min and longer paraformaldehyde fixation of about 20 min were performed before the –20° C. acetone treatment.

Embryos were then treated with PBS-DT blocking solution (1× PBST, 1% BSA, 1% DMSO, 0.1% Triton X-100, 2% goat serum) for 1 hour, followed by incubating with pre-absorbed anti-GFP antibody (pre-diluted 1:1000) at about 4° C. overnight. After PBS-DT washes for approximately 4 hour, embryos were incubated in biotin-anti-rabbit IgG (1:500; Vector) diluted with PBS-DT blocking solution at 4° C. overnight. Embryos were washed again with the PBST-DT solution for a total of about 6 hour time period and then incubated with ABC (Vector) reagent at room temperature for 2 hour, followed by several rinses with the PBS-DT solution. Thereafter, embryos were stained in 1 ml of a DAB/nickel solution (Vector) prepared according to manufacturer's protocols for 5-10 min and monitored under a microscope. The chromogenic reaction was terminated by washes with 0.1 M $NaPO_4$ (pH 7.4), followed by 4% paraformaldehyde fixation at about 4° C. overnight.

Cryostat sectioning was conducted according to Westerfield (1995). Embryos were washed with a fix buffer (4% sucrose, 0.15 mM $CaCl_2$, 0.1 M $NaPO_4$, pH 7.4) about three times for 5 min at room temperature, followed by embedding embryos in agar (1.5% agar, 5% sucrose, 0.1 M $NaPO_4$, pH 7.4) into agar blocks. Agar blocks containing different embryos were soaked in 30% sucrose until they sank. Embryos in agar blocks were transferred to an embedding chamber filled with OCT cryostat embedding medium (Tissue Tek), frozen inside a cryostat (Leica CM1900). Cryostat sections at about 16 μm interval were produced according to the manufacturer's procedures.

EXAMPLE 17

Zebrafish BMP4 Promoter and the 5'-Upstream Region Drive GFP Expression in the Myocardium of Ventricles of Transgenic $F_1$ Embryos The results from immunohistochemistry and cryostat sectioning of long-pec $F_1$ embryos, protruding-mouth $F_1$ embryos, and 100 hour-post-fertilization (hpf) $F_1$ embryos demonstrate variation of GFP expression in different parts of heart tissue during embryonic development. As shown in Table 2, $F_1$ progeny from 4 transgenic lines exhibit GFP expression mainly in the ventricle with different intensities, while those embryos from the other 6 transgenic lines contained GFP expression in both the ventricle and atrium. Therefore, $F_1$ embryos from approximately 40% of the transgenic $F_0$ lines direct in vivo GFP expression mainly only in the ventricles, while those from other transgenic $F_0$ lines (about 60%) direct in vivo GFP expression in both the atrium and ventricle. The positional effect of different integration sites in the chromosome may have contributed to this variation. The results support a mechanism of germ cells mosaicism in $F_0$ founder fish. This result is consistent with previous transgenic fish reports.

In general, endogenous BMP4 is expressed in bilateral heart primordia at the 18-somite stage, and BMP4 endogenous expression in long-pec embryos is restricted at the sinus venosus-atrial, atrio-ventricular, and ventriculo-arterial junctions. In our $F_1$ embryos from the transgenic B line, GFP expression is readily observed as an oval-shaped tube at around 30 hour post fertilization, and strong GFP expression is detected in all ventricle regions in long-pec embryos. The difference between GFP expression directed by our heart-specific expression construct and the endogenous BMP4 expression pattern may have been due to lack of DNA elements that controls accurate temporal activation and maintenance of GFP expression in the 7.5 kb Bgl II construct.

$F_1$ embryos from the transgenic B line were chosen for further analysis of GFP expression in the heart during different developmental stages because of the abundant positive $F_1$ progeny. The earliest GFP expression was observed in prim-15 $F_1$ embryos having a conical to elongated shape. As development continued, GFP expression was located in the ventricles in long-pec, protruding-mouth, and 100-hpf embryos via both fluorescence and confocal microscopy, as shown in FIGS. 9A-9I. In addition, GFP expression in the heart of embryos could be observed as long as about 6 days after hatching. These results further confirmed that the 7.5-kb BMP4 promoter and its upstream region participate in heart-specific GFP expression.

FIGS. 9J-9L exemplify the results of $F_1$ embryos of the transgenic B line from immunocytochemistry using the anti-GFP antibody followed by cryostat sectioning. It is clear that GFP expression is localized in the myocardium of the ventricles of the three developmental stages of $F_1$ embryos examined, long-pec (FIG. 9J), protruding-mouth (FIG. 9K), and 100-hpf (FIG. 9L). In summary, GFP expression in $F_1$ embryos of the transgenic B line, localized in the myocardium of the ventricle is readily observed from about 48 hour to about 100 hour post fertilization (hfp).

In addition, the formation of trabeculae in the ventricle could be observed via staining of GFP in 100-hpf embryos, as shown in FIG. 9L. This observation is consistent with a previous study showing the formation of trabeculae in the ventricle occurred at around 72 hours to 120 hours post fertilization. This is consistent with studies for higher vertebrate organisms where bone morphogenetic protein signaling, such as BMP4 signaling, have been shown to play an essential role in the induction of cardiac myogenesis. For example, bone morphogenetic proteins act as paracrine signals to specify cardiac myocyte induction in avian explant studies.

In 9.0 days p.c. mouse embryos, BMP4 mouse transcripts were expressed in the outer myocardial layer of the developing atrioventricular canal. In addition, cardiac myocyte-specific deletion of the mouse type IA BMP receptor, ALK3, suggest that the ALK3 BMP receptor is specifically required for the development of the trabeculae, compact myocardium, interventricular septum, and endocardial cushion. Our GFP localization results coincide with trabeculae formation (FIG. 9L) suggests that expression of zebrafish BMP4, similar to mouse BMP4, acts as an autocrine signal for heart development. However, nucleic acid sequence comparison between the promoter and upstream regions of mouse and zebrafish BMP4 genes revealed no significant homology.

EXAMPLE 18

Establishment of Stable Transgenic Zebrafish Lines Expressing GFP in Their Hearts We further crossed adult $F_1$ transgenic fish from several transgenic lines with wild type fish. The transmission rate from $F_1$ to $F_2$ fall into the standard Mendelian inheritance ratio of 50%, indicating that the transgene (i.e., different BMP4 DNA fragments) in these transgenic lines had been integrated into a single chromosome locus (data not shown).

EXAMPLE 19

Photography and Computer Analysis

Images of embryos from transient expression analysis, from the transgenic B line, as well as from cryostat sectioning were taken using an RT color digital camera (SPOT) on an Olympus BX60 microscope equipped with DIC mode and an FITC filter. Laser confocal microscopic images were obtained using a Leica TCS NT laser-scanning microscope equipped with an FITC filter. Nucleic acid sequences were analyzed using Lasergene software (DNASTAR). Motif (http://motif.genome.ad.jp) was used to predict possible binding sites for transcription factors.

While the foregoing is directed to embodiments of the invention, other and further embodiments of the invention may be devised without departing from the basic scope thereof, and the scope thereof is determined by the claims that follow.

What is claimed is:

1. An isolated DNA molecule comprising a nucleic acid sequence which comprises SEQ. ID NO. 1.

2. The isolated DNA molecule of claim 1, wherein the nucleic acid sequence further comprises SEQ. ID NO. 9.

3. The isolated DNA molecule of claim 1, further comprising a nucleotide sequence encoding a heterologous expression product selected from the group consisting of β-galactosidase, luciferase, chloramphenicol acetyl transferase (CAT), green fluorescent protein (GFP), human growth hormone, alkaline phosphatase, β-glucuronidase, and combinations thereof.

4. The isolated DNA molecule of claim 1, wherein the nucleic acid sequence further comprises SEQ. ID NO. 8.

5. The isolated DNA molecule of claim 1, wherein the nucleic acid sequence further comprises SEQ. ID NO. 7.

6. The isolated DNA molecule of claim 1, wherein the nucleic acid sequence further comprises SEQ. ID NO. 4.

7. A transgenic zebrafish comprising the isolated DNA molecule of claim 1 operatively linked to a heterologous DNA.

8. The transgenic zebrafish of claim 7, wherein the transgenic zebrafish is a zebrafish embryo.

9. The transgenic zebrafish of claim 7, wherein the isolated DNA molecule further comprises SEQ ID NO. 9.

10. The transgenic zebrafish of claim 7, wherein the isolated DNA molecule further comprises SEQ. ID NO. 8.

11. The transgenic zebrafish of claim 7, wherein the isolated DNA molecule further comprises SEQ. ID NO. 7.

12. The transgenic zebrafish of claim 7, wherein the isolated DNA molecule further comprises SEQ. ID NO. 4.

13. The transgenic zebrafish of claim 7, wherein the heterologous DNA encodes a heterologous expression product.

14. The transgenic zebrafish of claim 13, wherein the heterologous expression product is a reporter protein selected from the group consisting of β-galactosidase, luciferase, chloramphenicol acetyl transferase (CAT), green fluorescent protein (GFP), human growth hormone, alkaline phosphatase, β-glucuronidase, and combinations thereof.

15. The transgenic zebrafish of claim 14, wherein the reporter protein is green fluorescent protein.

16. The transgenic zebrafish of claim 13, wherein the expression sequence directs stable expression of the heterologous expression product.

17. The transgenic zebrafish claim 13, wherein the expression of the heterologous expression product is transmitted through a germ line.

18. The transgenic zebrafish of claim 13, wherein the expression sequence and the sequence encoding the heterologous expression product are contained in an exogenous construct.

19. The transgenic zebrafish of claim 13, wherein the exogenous construct is integrated into a genome of the transgenic zebrafish.

20. An isolated DNA molecule obtained from upstream regulatory region of a zebrafish bone morphogenetic protein 4 gene and having a nucleic acid sequence which comprises SEQ. ID NO. 1.

21. The isolated DNA molecule of claim 20, wherein the nucleic acid sequence further comprises SEQ. ID NO. 9.

* * * * *